(12) United States Patent
Zarbis-Papastoitsis et al.

(10) Patent No.: US 10,799,589 B2
(45) Date of Patent: Oct. 13, 2020

(54) CHIMERIC CYTOKINE FORMULATIONS FOR OCULAR DELIVERY

(71) Applicant: BUZZARD PHARMACEUTICALS AB, Solna (SE)

(72) Inventors: Gregory Zarbis-Papastoitsis, Watertown, MA (US); Patricia Lowden, Hudson, MA (US); Byeong Chang, Thousand Oaks, CA (US)

(73) Assignee: BUZZARD PHARMACEUTICALS AB, Solna (SE)

( * ) Notice: Subject to any disclaimer, the term of this patent is extended or adjusted under 35 U.S.C. 154(b) by 0 days.

(21) Appl. No.: 15/670,840

(22) Filed: Aug. 7, 2017

(65) Prior Publication Data

US 2018/0177877 A1    Jun. 28, 2018

Related U.S. Application Data

(63) Continuation of application No. 14/209,605, filed on Mar. 13, 2014, now abandoned.

(60) Provisional application No. 61/779,974, filed on Mar. 13, 2013.

(51) Int. Cl.
| | | |
|---|---|---|
| *A61K 47/10* | (2017.01) | |
| *A61K 38/20* | (2006.01) | |
| *C07K 14/545* | (2006.01) | |
| *C07K 14/715* | (2006.01) | |
| *A61K 47/26* | (2006.01) | |
| *A61K 47/18* | (2017.01) | |
| *A61K 47/02* | (2006.01) | |
| *A61K 47/12* | (2006.01) | |
| *A61K 9/00* | (2006.01) | |
| *A61K 47/38* | (2006.01) | |

(52) U.S. Cl.
CPC ............ *A61K 47/10* (2013.01); *A61K 9/0048* (2013.01); *A61K 38/20* (2013.01); *A61K 38/2006* (2013.01); *A61K 47/02* (2013.01); *A61K 47/12* (2013.01); *A61K 47/26* (2013.01); *C07K 14/545* (2013.01); *C07K 14/7155* (2013.01); *A61K 47/183* (2013.01); *A61K 47/38* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,343,787 A | 8/1982 | Katz | |
| 4,770,781 A | 9/1988 | Schmidt et al. | |
| 4,804,539 A | 2/1989 | Guo et al. | |
| 4,883,658 A | 11/1989 | Holly | |
| 4,898,818 A | 2/1990 | Nakai et al. | |
| 5,075,104 A | 12/1991 | Gressel et al. | |
| 5,075,222 A | 12/1991 | Hannum et al. | |
| 5,122,459 A | 6/1992 | Conlon, III et al. | |
| 5,278,151 A | 1/1994 | Korb et al. | |
| 5,286,847 A | 2/1994 | Gehrke et al. | |
| 5,340,572 A | 8/1994 | Patel et al. | |
| 5,349,051 A | 9/1994 | Veerapandian | |
| 5,453,490 A | 9/1995 | Hageman et al. | |
| 5,484,887 A | 1/1996 | Kronheim et al. | |
| 5,510,462 A | 4/1996 | Auron et al. | |
| 5,530,101 A | 6/1996 | Queen et al. | |
| 5,578,586 A | 11/1996 | Glonek et al. | |
| 5,585,089 A | 12/1996 | Queen et al. | |
| 5,693,489 A | 12/1997 | Studier et al. | |
| 5,693,761 A | 12/1997 | Queen et al. | |
| 5,693,762 A | 12/1997 | Queen et al. | |
| 5,739,277 A | 4/1998 | Presta et al. | |
| 5,770,401 A | 6/1998 | Mullarkey | |
| 5,789,650 A | 8/1998 | Lonberg et al. | |
| 5,861,476 A | 1/1999 | Barrett et al. | |
| 5,922,573 A | 7/1999 | Boraschi et al. | |
| 5,985,657 A | 11/1999 | Auron et al. | |
| 5,998,578 A | 12/1999 | Auron et al. | |
| 6,090,775 A | 7/2000 | Rothwell et al. | |
| 6,096,728 A | 8/2000 | Collins et al. | |
| 6,107,465 A | 8/2000 | Nakai et al. | |
| 6,159,460 A | 12/2000 | Thompson et al. | |
| 6,337,072 B1 | 1/2002 | Ford et al. | |
| 6,407,213 B1 | 6/2002 | Carter et al. | |
| 6,416,753 B1 | 7/2002 | Yuan et al. | |
| 6,419,944 B2 | 7/2002 | Tobinick | |
| 6,471,961 B1 | 10/2002 | Tobinick | |
| 6,599,873 B1 | 7/2003 | Sommer et al. | |
| 6,602,503 B1 | 8/2003 | Lobb et al. | |

(Continued)

FOREIGN PATENT DOCUMENTS

| | | |
|---|---|---|
| CA | 2648223 A1 | 10/2007 |
| CN | 1592629 A | 3/2005 |

(Continued)

OTHER PUBLICATIONS

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25. (Year: 2002).*

Dana et al. "Corneal Antigen Presentation: Molecular Regulation and Functional Implications" The Ocular Surface, 3 (4):S169-S172, Oct. 2005.

Dana et al., "Topical interleukin 1 receptor antagonist promotes corneal transplant survival", Transplantation, 63 (10)1501-1507 (1997).

(Continued)

*Primary Examiner* — Vanessa L. Ford
*Assistant Examiner* — Sandra E Dillahunt
(74) *Attorney, Agent, or Firm* — Lando & Anastasi, LLP

(57) ABSTRACT

Featured herein are vehicle formulations and formulations containing a chimeric cytokine designed for e.g., ocular delivery.

11 Claims, 12 Drawing Sheets

Specification includes a Sequence Listing.

(56) References Cited

U.S. PATENT DOCUMENTS

| | | |
|---|---|---|
| 6,623,736 B2 | 9/2003 | Tobinick |
| 6,858,409 B1 | 2/2005 | Thompson et al. |
| 6,927,044 B2 | 8/2005 | Stahl et al. |
| 6,974,682 B1 | 12/2005 | Bednarik et al. |
| 7,087,224 B2 | 8/2006 | Kay et al. |
| 7,482,323 B2 | 1/2009 | Hasty et al. |
| 7,619,066 B2 | 11/2009 | Raibekas et al. |
| 7,674,464 B2 | 3/2010 | Hasty et al. |
| 7,700,318 B2 | 4/2010 | Hui |
| 7,956,160 B2 | 6/2011 | Krishnan et al. |
| 8,303,945 B2 | 11/2012 | Dahlen et al. |
| 8,414,876 B2 | 4/2013 | Mellis et al. |
| 8,853,150 B2 | 10/2014 | Barnes et al. |
| 9,011,861 B2 | 4/2015 | Dana et al. |
| 2001/0041792 A1 | 11/2001 | Donda et al. |
| 2001/0042304 A1 | 11/2001 | Sato |
| 2003/0004106 A1 | 1/2003 | Saris et al. |
| 2003/0007971 A1 | 1/2003 | Hara et al. |
| 2003/0026806 A1 | 2/2003 | Witte et al. |
| 2003/0070185 A1 | 4/2003 | Jakobovits et al. |
| 2003/0083301 A1 | 5/2003 | Perez-Polo et al. |
| 2003/0104996 A1 | 6/2003 | Li et al. |
| 2003/0166069 A1 | 9/2003 | Welcher et al. |
| 2004/0022718 A1 | 2/2004 | Stupp et al. |
| 2004/0028872 A1 | 2/2004 | Edwards et al. |
| 2004/0044001 A1 | 3/2004 | Bendele et al. |
| 2004/0208872 A1 | 10/2004 | Welcher et al. |
| 2004/0208874 A1 | 10/2004 | Khare |
| 2005/0023872 A1 | 2/2005 | Hetzel et al. |
| 2005/0033694 A1 | 2/2005 | Perrin |
| 2005/0059589 A1 | 3/2005 | Mullarkey |
| 2005/0105830 A1 | 5/2005 | Chung et al. |
| 2005/0123512 A1 | 6/2005 | Calzone et al. |
| 2005/0143333 A1 | 6/2005 | Richards et al. |
| 2005/0171337 A1 | 8/2005 | Bednarik et al. |
| 2005/0271618 A1 | 12/2005 | Raibekas et al. |
| 2006/0088600 A1 | 4/2006 | Thornion et al. |
| 2006/0094663 A1 | 5/2006 | Chemtob et al. |
| 2006/0110429 A1 | 5/2006 | Reiff et al. |
| 2007/0027082 A1 | 2/2007 | Hasty et al. |
| 2007/0098684 A9 | 5/2007 | Raibekas et al. |
| 2007/0248597 A1 | 10/2007 | Henley et al. |
| 2008/0019964 A1 | 1/2008 | Olmarker et al. |
| 2008/0026485 A1 | 1/2008 | Hueber et al. |
| 2008/0199460 A1 | 8/2008 | Cua et al. |
| 2008/0242634 A1 | 10/2008 | Perez-Polo |
| 2009/0011745 A1 | 1/2009 | Cha |
| 2009/0022733 A1 | 1/2009 | Sims et al. |
| 2009/0111745 A1 | 4/2009 | Tomlinson |
| 2009/0136453 A1 | 5/2009 | Watkins |
| 2009/0176217 A1 | 7/2009 | Sella-Tavor et al. |
| 2009/0214619 A1 | 8/2009 | Reiff et al. |
| 2009/0226530 A1* | 9/2009 | Lassner ............. A61K 9/1605 514/1.1 |
| 2010/0028328 A1 | 2/2010 | Reiff et al. |
| 2010/0047204 A1 | 2/2010 | Yoo et al. |
| 2010/0068210 A1* | 3/2010 | Ji .................. A61K 9/0019 514/1.1 |
| 2010/0120684 A1 | 5/2010 | Dahlen et al. |
| 2010/0183587 A1 | 7/2010 | Dana et al. |
| 2010/0203103 A1 | 8/2010 | Dana et al. |
| 2010/0226963 A1 | 9/2010 | Cooper et al. |
| 2011/0104236 A1 | 5/2011 | Dana et al. |
| 2012/0014970 A1 | 1/2012 | Dana et al. |
| 2013/0045927 A1 | 2/2013 | Dana et al. |
| 2013/0195868 A1 | 8/2013 | Adelman |
| 2013/0209396 A1 | 8/2013 | Barnes et al. |
| 2014/0073556 A1 | 3/2014 | Berezin et al. |
| 2015/0246966 A1 | 9/2015 | Dana et al. |

FOREIGN PATENT DOCUMENTS

| | | |
|---|---|---|
| EP | 36776 A2 | 9/1981 |
| EP | 239400 A2 | 9/1987 |
| EP | 0343684 A1 | 11/1989 |
| EP | 362179 A2 | 4/1990 |
| EP | 0541920 A1 | 5/1993 |
| EP | 661992 A1 | 7/1995 |
| EP | 1778723 A2 | 5/2007 |
| JP | 108295622 A | 11/1996 |
| JP | 2005527649 A | 9/2005 |
| RU | 2409591 C2 | 1/2011 |
| WO | 9007861 A1 | 7/1990 |
| WO | 9117184 A1 | 11/1991 |
| WO | 9510298 A1 | 4/1995 |
| WO | 96/09323 A1 | 3/1996 |
| WO | 9634096 A1 | 10/1996 |
| WO | 98/22130 A1 | 5/1998 |
| WO | 9847921 A1 | 10/1998 |
| WO | 199847921 A1 | 10/1998 |
| WO | 9925354 A2 | 5/1999 |
| WO | 00/42072 A2 | 7/2000 |
| WO | 02/060919 A2 | 8/2002 |
| WO | 2002062375 A1 | 8/2002 |
| WO | 03022213 A2 | 3/2003 |
| WO | 2003068920 A2 | 8/2003 |
| WO | 2005086695 A2 | 9/2005 |
| WO | 2005097195 A2 | 10/2005 |
| WO | 2007039903 A2 | 4/2007 |
| WO | 2007/120828 A1 | 10/2007 |
| WO | 2007/145618 A1 | 12/2007 |
| WO | 2008049043 A2 | 4/2008 |
| WO | 08/132485 A2 | 11/2008 |
| WO | 2008/155134 A1 | 12/2008 |
| WO | 2008145664 A1 | 12/2008 |
| WO | 2009/023270 A2 | 2/2009 |
| WO | 09025763 A2 | 2/2009 |
| WO | 2009048961 A1 | 4/2009 |
| WO | 09089036 A2 | 7/2009 |
| WO | 2010052505 A1 | 5/2010 |
| WO | 2010062896 A1 | 6/2010 |
| WO | 2010081091 A2 | 7/2010 |
| WO | 2010089522 A1 | 8/2010 |
| WO | 2010/118888 A1 | 10/2010 |
| WO | 2011/011797 A2 | 1/2011 |
| WO | 2011028344 A2 | 3/2011 |
| WO | 2011/044563 A2 | 4/2011 |
| WO | 2011/063195 A2 | 5/2011 |
| WO | 2011106697 A1 | 9/2011 |
| WO | 2011123813 A2 | 10/2011 |
| WO | 2011163452 A2 | 12/2011 |
| WO | 2012016203 A1 | 2/2012 |
| WO | WO-2012016203 A1 * | 2/2012 ........... C07K 14/545 |
| WO | 2012063237 A2 | 5/2012 |
| WO | 2012103240 A2 | 8/2012 |
| WO | 2012122985 A1 | 9/2012 |
| WO | 2013019652 A1 | 2/2013 |
| WO | WO-2013019652 A1 * | 2/2013 ......... B01D 15/1864 |
| WO | 2014160371 A1 | 10/2014 |

OTHER PUBLICATIONS

Dana et al., "Topical Modulation of interleukin-1 activity in corneal neovascularization", Cornea, 17(4):403-409 (1998) (Abstract).

Dana, "Comparison of topical interleukin-1 vs tumor necrosis factor-alpha blockade with corticosteroid therapy on murine corneal inflammation, neovascularization, and transplant survival (an American Ophthalmological Society thesis)" Trans Am Ophthalmol Soc 105: 330-43, (2007).

Dartt et al. "Dysfunctional Neural Regulation of Lacrimal Gland Secretion and its Role in the Pathogenesis of Dry Eye Syndrome." Ocul. Surf. 2.2(2004):76-91.

Database UniPort [Online] Jul. 23, 2010, anonymous: "IL1RA_MOUSE", retrieved from www.uniport.org, Database accession No. P25085.

Database Uniprot [Online] Jul. 13, 2010, anonymous: "IL1F5_HUMAN", retrieved from www.uniport.org Database accession No. Q9UBH0.

Database UniProt [Online] Jul. 13, 2010, anonymous: "IL1RA_HUMAN" retrieved from www.uniport.org.

Dayer et al., "Anti-interleukin-1 therapy in rheumatic diseases", Curr. Opin. Rheumatol., 13:170-176 (2001).

(56) References Cited

OTHER PUBLICATIONS

De Salamanca et al. "Tear cytokine and chemokine analysis and clinical correlations in evaporative-type dry eye disease" Mol. Vis. 16:862-873, (2010).
DeBoer et al., "The tac promoter: A functional hybrid derived from the trp and lac promoters" Proc. Natl. Acad. Sci. USA, 80:21-25 (1983).
Dekaris et al., Effect of topical interleukin-1 receptor antagonist (IL-1ra) on corneal allograft survival in presensitized hosts, Curr Eye Res 19(5): 456-9, (1999).
DeKosky et al. "Interleukin-1 Receptor Antagonist Suppresses Neurotrophin Response in Injured Rat Brain." Ann. Neural. 39(1996):123-127.
Demircan et al. Determination of vitreous interleukin-1(1L-1) and tumour necrosis factor (TNF) levels in proliferative diabetic retinopathy, Eye 20:1366-1369, (2006).
Dennis et al. "Albumin Binding as a General Strategy for Improving the Pharmacokinetics of Proteins" J. Biol. Chem. 277:35035-35043 (2002).
Deutscher, "Maintaining protein stability." Methods in Enzymology, 182, 83-89 (1990).
Dinarello et al., Current Protocols in Immunology, Ch. 6.2.1-6.2.7, John Wiley and Sons Inc., (2000).
Dinarello, "Immunological and Inflamatory Functions of the Interleukin-I Family", Annual Review of Immunology, vo 1.27, No. 1, Apr. 1, 2009 (Apr. 1, 2009), pp. 519-550.
Dinarello, C.A., "Biologic basis for interleukin", Blood, 87(6):2095-2147 (1996).
Dinarello, C.A., "The role of the interleukin-1-receptor antagonist in blocking inflammation mediated by interleukin-1", N Engl. J Med., 343(10):732-734 (2000).
Doganay et al. Comparison of serum NO, TNF-beta, IL-1beta, sIL-2R, IL-6 and IL-8 levels with grades of retinopathy in patients with diabetes mellitus Eye, 16:163-170, (2006).
Duncan et al., "Repair of myelin disease: strategies and progress in animal models" Molec. Med. Today, 554-561, (1997).
Economides et al., Cytokine traps: multi-component, high-affinity blockers of cytokine action Nature Med., 9:47-52 (2003).
Evans et al., "Mapping receptor binding sites in interleukin (IL)-1 receptor antagonist and IL-1 beta by site-directed mutagenesis. utagenesis. Identification of a single site in IL-1ra and two sites in IL-1 beta" J. Biol. Chem., 270:11477 (1995).
Fabre et al., "Binding sites for human interleukin 1alpha, gamma interferon and tumor necrosis factor on cultures fibroblasts of normal cornea and keratoconus", Curr. Eye. Res., 10:585-592 (1991).
Faour et al., "T-cell-derived interleukin-17 regulates the level and stability of cyclooxygenase-2 (COX-2) mRNA through restricted activation of the p38 mitogen-activated protein kinase cascade: role of distal sequences in the 3'-intranslated region of COX-2 mRNA." J. Biol. Chem., 278, 26897-26907, (2003).
Feldmann et al. "Chronic infantile neurological cutaneous and articular syndrome is caused by mutations in CIAS1, a gene highly expressed in polymorphonuclear cells and chondrocytes", Am J Hum Genet 71:198-203, (2002).
Ferry, et al, "Liver-Directed Gene Transfer Vectors" Hum. Gene Ther. 9:1975-81; (1998).
Fini et al., "Express of Collagenolytic I Gelatinolytic Metalloproteinases by Normal Cornea", Invest. Opthalmol. Vis. Sci., 31:1779-1788 (1990).
Finzel et al. Crystal Structure of Recombinant Human Interleukin-1? at 2-0 A Resolution, J. Mol. Biol. 209: 779-791, (1989).
Fisher et al., "Recombinant human interleukin I receptor antagonist in the treatment of patients with sepsis syndrome: results from a randomized, double-blind, placebo-controlled trial", JAMA., 271(23):1836-1843 (1994).
Fleischmann, et al. "Anakinra, a recombinant human interleukin-1 receptor antagonist (r-metHuIL-1ra), in patients with rheumatoid arthritis: A large, international, multicenter, placebo-controlled trial" Arthritis & Rheumatism 48, 927-34 (2003).

Fossiez et al., "T cell interleukin-17 induces stromal cells to produce proinflammatory and hematopoietic cytokines." J Exp Med.;183(6):2593-603, Jun. 1, 1996.
Foulks et al., "Meibomian gland dysfunction: A clinical scheme for description, diagnosis, classification, and grading", Ocul. Suif., 1(3):107-126 (2003).
Freund et al. Upregulation of Nerve Growth Factor Expression by Human Airway Smooth Muscle Cells in Inflammatory Conditions. Eur. Resp. J. 20(2002):458-463.
Fu, Y.A., "Ocular manifestation of polychlorinated biphenyls intoxication", Am. J Ind. Med., 5: 127-132 (1984).
Fukushima et al., "Ag-specific recognition, activation, and effector function of T cells in the conjunctiva with experimental immune-mediated blepharoconjunctivitis", Invest. Opthalmol. Vis. Sci., 44:4366-4374 (2003).
Furfine, E.S., et al., "EBI-005: An IL-1 Receptor Inhibitor Designed for the Treatment of Dry Eye Syndrome," Retrieved from the Internet: URL:http://www.elevenbio.com/pdf/Eleven_poster_042312_lowres.pdf, pp. 1-1, (May 7, 2012) [Retrieved on Aug. 27, 2012].
Gabay et al., "Mouse IL-I receptor antagonist isoforms: complementary DNA cloning and protein expression of intracellular isoform and tissue distribution of secreted and intracellular IL-I receptor antagonist in vivo", J. Immunol., 159:5905-5913 (1997).
Galea, J., et al., "Intravenous anakinra can achieve experimentally effective concentrations in the central nervous system within a therapeutic time window: results of a dose-ranging study," Journal of Cerebral Blood Flow & Metabolism, 31(2):439-447 (2020) (Abstract).
Genovese et al, "LY2439821, a Humanized Anti-Interleukin-17 Monoclonal Antibody, in the Treatment of Patients with Rheumatoid Arthritis" Arthritis & Rheumatism (2010) 62(4):929-939.
Gerhardt et al, "Structure of IL-17A in complex with a potent, fully human neutralizing antibody." J. Mol. Biol. 394:905-921 (2009).
Ghetie et al., "Multiple roles for the major histocompatibility complex class I-related receptor FcRn." Ann. Rev. Immunol. 18:739-766 (2000)).
Gluzman et al., "SV40-transformed simian cells support the replication of early SV40 mutants." Cell 23:175, (1981).
Glynn et al., "Comparison of alternative regression models for paired binary data", Stat. Med., 13(10):1023-1036 (1994).
Goeddel et al., "Direct expression in *Escherichia coli* of a DNA sequence coding for human growth hormone." Nature, 281:544 (1979).
Goeddel, "Synthesis of human fibroblast interferon by *E. coli.*" Nucleic Acids Res., 8:4057 (1980).
Goto et al., "Impaired functional visual acuity of dry eye patients", Am. J. Opthalmol., 133:181-186 (2002).
Green et al., "Antigen-specific human monoclonal antibodies from mice engineered with human Ig heavy and light chain YACs." Nature Genetics 7:13-21 (1994).
Greenfeder et al., "Insertion of a Structural Domain of Interleukin (IL)-1? Confers Agonist Activity to the IL-1 Receptor Antagonist" J. Biol. Chem., 270:22460-22466 (1995).
Martinsen et al., "Alginate as immobilization material: I. Correlation between chemical and physical properties of alginate gel beads", Biotech. Bioeng., 33:79-89 (1989).
Mattheakis et al. "An in vitro polysome display system for identifying ligands from very large peptide libraries" Proc. Natl. Acad. Sci. USA 91:9022, (1994).
McDevitt et al., "Interleukin-1 genetic association with periodontitis in clinical practice", J. Periodontal. 71: 156-163 (2000).
McIndoe et al., "Localization of non-Mhc collagen-induced arthritis susceptibility loci in DBA/1j mice", Proc. Natl. Acad. Sci. USA, 96:2210-2214; (1999).
McMahan et al. "A novel IL-1 receptor, cloned from B cells by mammalian expression, is expressed in many cell types." EMBO J. 10: 2821, (1991).
Miljanovic et al., "Impact of dry eye syndrome on vision-related quality of life", Am. J. Opthalmol., 143:409-415 (2007).
Muller et al. "Corneal Nerves: Structure, Contents and Function." Exp. Eye Res. 76(2003):521-542.
Muller et al. "Ultrastructural Organization of Human Corneal Nerves." Invest. Opthalmol. Vis. Sci. 37.4(1996):476-488.

(56) References Cited

OTHER PUBLICATIONS

Needleman, et al "A general method applicable to the search for similarities in the amino acid sequence of two proteins" J. Mol. Biol. 48, 443-453, (1970).
Nuki, et al. "Long-term safety and maintenance of clinical improvement following treatment with anakinra (recombinant human interleukin-1 receptor antagonist) in patients with rheumatoid arthritis: Extension phase of a randomized, double-blind, placebo-controlled trial" <http://onlinelibrary.wiley.com/doi/10.1002/art.10578/abstract>Arthritis & Rheumatism 46, 2838-46 (2002).
O'Neill et al., "Signal transduction pathways activated by the IL-I receptor family: ancient signaling machinery in mammals, insects, and plants", J. Leukocyte Biol., 63:650-657 (1998).
Oka, et al. "Recent advances in liver-directed gene therapy: implications for the treatment of dyslipidemia <http://journals.lww.com/co-lipidology/Abstract/2000/04000/Recent_advances_in_liver_directed_gene_therapy_.11.aspx>" Curr. Opin. Lipidol. 11:179-86; (2000).
Okusawa et al., "Interleukin 1 induces a shock-like state in rabbits", J. Clin. Invest., 81: 1162-1172 (1988).
Olson et al. "Intravitreal Anakinra Inhibits Choroidal Neovascular Membrane Growth in a Rat Model" Ocul Immunol Inflamm 17(3):195-200, (2009).
Owyang et al. "XOMA 052, an Anti-IL-1? Monoclonal Antibody, Improves Glucose Control and ?-Cell Function in the Diet-Induced Obesity Mouse Model" Endocrinology, 151(6):2515-27, (2010).
Patel et al. "Interleukin-1 in the Brain." Ann. N.Y. Acad. Sci. 992(2003):39-47.
Pawliuk et al. "Systematic Genetic Analysis with Ordered Arrays of Yeast Deletion Mutants" Science 294:2368, (2001).
Pearson, "Comparison of methods for searching protein sequence databases", Protein Science 4, 1145-1160, (1995).
Pflugfelder et al., "Altered cytokine balance in the tear fluid and conjunctiva of patients with sjogren's yndrome keratoconjunctivitis sicca", Curr. Eye Res., 19:201-211 (1999).
Pflugfelder et al., "Conjuctival cytologic features of primary sjogren's syndrome", Ophthalmol., 97(8):985-991 (1990).
Pincus et al. "Assessment of Patient Satisfaction in Activities of Daily Living Using a Modified Stanford Health Assessment Questionnaire" Arthritis Rheum. 26(11):1346-53, (1983).
Pisella et al., "Flow Cytometric Analysis of Conjunctival Epithelium in Ocular Rosacea and Keratoconjunctivitis Sicca", Opthalmol., 107:1841-1849 (2000).
Quartier et al. "Extended report: A multicentre, randomised, double-blind, placebo-controlled trial with the interleukin-1 receptor antagonist anakinra in patients with systemic-onset juvenile idiopathic arthritis" Ann Rheum Dis. 70(5):747-54, (2011).
Dana et al. Randomized Phase II Trial of safety and efficacy of Topical interleukin-1 receptor antagonist (IL-Ra) for treatment of Meibomian Gland Dysfunction (MGD)—associated ocular surface disease. Abstract publication date: Jun. 24, 2010; Poster publication date Jun. 25, 2012.
Reiff, A., "The use of anakinra in juvenile arthritis", Curr. Rheumatol. Rep., 7:434-440 (2005).
Relton, J.K., et al., "Interleukin-1 Receptor Antagonist Inhibits Ischaemic and Excitotoxic Neuronal Damage in the Rat," Brain Research Bulletin, 29(2):243-246 (1992) (Abstract).
Rice, P. et al., "EMBOSS: The European Molecular Biology Open Software Suite" Trends in Genetics, 16, (6) pp. 276-277, (2000).
Riechmann et al., "Reshaping human antibodies for therapy" Nature 332, 323-327, 1988.
Rosenbaum et al., "Detection of mRNA for the Cytokines, Interleukin-1 alpha and interleukin-8, in corneas from patients with pseudophakic bullous keratopathy", Invest. Opthalmol. Vis. Sci., 36:2151-2155 (1995).
Rosner et al., "Incorporation of clustering effects for the Wilcoxon rank sum test: A Large-Sample Approach", Biometrics, 59(4):1089-1098 (2003).
Rothwell, et al., "Interleukin 1 in the brain: biology, pathology and therapeutic target" TINS 23(12): 618-625, (2000).

Sall et al., "Two multicenter, randomized studies of Efficacy and safety of cyclosporine ophthalmic emulsion in moderate to severe dry eye disease", Ophthalmol., 107:631-639 (2000).
Schaffitzel et al. "Ribosome display: an in vitro method for selection and evolution of antibodies from libraries." (1999).
Schiff, et al. "The safety of anakinra in high-risk patients with active rheumatoid arthritis: six-month observations of patients with comorbid conditions" Arthritis & Rheumatism 50, 1752-60 (2004).
Schiffinan et al., "Reliability and Validity of the Ocular Surface Disease index", Arch. OphthalmoL, 118:615-621 (2000).
Schreuder et al., A new cytokine-receptor binding mode revealed by the crystal structure of the IL-1 receptor with an antagonist Nature 386: 194-200, (1997).
Shields et al., "High resolution mapping of the binding site on human IgG1 for Fc gamma RI, Fc gamma RII, Fc gamma RIII, and FcRn and design of IgG1 variants with improved binding to the Fc gamma R." J. Biol. Chem. 276:6591-6604 (2001).
Shimazaki et al., "Meibomian gland dysfunction in patients with sjogren syndrome", Opthalmol., 105:1485-1488 (1998).
Shiratory, et al. "Strategy of liver-directed gene therapy: present status and future prospects." Liver 19:265-74; (1999).
Siemion, I.Z., et al., "Anti-IL-1 Activity of Peptide Fragments of IL-1 Family Proteins," Peptides, 19(2):373-382 (1998).
Sims , et al., "The IL-1 family: regulators of immunity, Nature Reviews Immunology" Nat Rev Immunol. <http://www.ncbi.nlm.nih.gov/pubmed/20081871> 10(2):89-102, (Feb. 2010).
Sjolander, et al., "Integrated fluid handling system for biomolecular interaction analysis", Anal. Chem. 63:2338-2345, (1991).
Smith "Filamentous fusion phage: novel expression vectors that display cloned antigens on the virion surface." Science 228:1315-1317, (1985).
Smith et al., "Doxycycline-a role in ocular surface repair", Br. J. Ophthalmol., 88:619-625 (2004).
Smith-Arica, et al. "Gene therapy: recombinant adeno-associated virus vectors." Curr. Cardiol. Rep. 3:43-49; (2001).
Solomon et al., "Doxycycline inhibition of interleukin-1 in the corneal epithelium", Invest. Opthalmol. Vis. Sci., 41:2544-2557 (2000).
Solomon et al., "Pro- and Anti-inflammatory forms of interleukin-1 in the tear fluid and conjunctiva of patients with dry-eye disease", Invent. Opthalmol. Vis. Sci., 42:2283-2292 (2001).
Stevenson et al., "Efficacy and safety of cyclosporine a ophthalmic emulsion in the treatment of moderate-to-severe dry eye disease", Opthalmol., 107(5):967-974 (2000).
Szabo et al., "Surface plasmon resonance and its use in biomolecular interaction analysis (BIA).", Curr. Opin. Struct. Biol. 5:699-705, (1995).
Temporin et al. "Interleukin-1 Beta Promotes Sensory Nerve Regeneration after Sciatic Nerve Injury." Neurosci. Lett. 440.2(2008):130-133.
Guenard et al. "Peripheral Nerve Regeneration is Impended by Interleukin-1 Receptor Antagonist Released from a Polymeric Guidance Channel." J. Neurosci. Res. 29(1991):396-400.
Hanes et al. "Picomolar affinity antibodies from a fully synthetic naive library selected and evolved by ribosome display" Nat Biotechnol. 18:1287-92, (2000).
Hanes et al. "Selecting and evolving functional proteins in vitro by ribosome display" Methods Enzymol. 328:404-30; (2000).
Hassan et al. "Increased Susceptibility to Dextran Sulfate Sodium Induced Colitis in the T Cell Protein Tyrosine Phosphatase Heterozygous Mouse" PLoS One.;5(1):e8868 (Jan. 25, 2010).
He et al. "High throughput thermostability screening of monoclonal antibody formulations" J. Pharm. Sciences, 99 1707-1720, (2010).
Heidary et al, "Long Range Coupling between Separate Docking Sites in Interleukin-1Beta", Journal of Molecular Biology, Academic Press, United Kingdom, vol. 353, No. 5, Nov. 11, 2005.
Hess et al., "Cooperation of glycolytic enzymes" J. Adv. Enzyme Reg., 7:149 (1968).
Higgins et al., "Using CLUSTAL for multiple sequence alignments", Methods Enzymol. 266, 383-402, (1996).
Hinton, "Engineered Human IgG Antibodies with Longer Serum Half-lives in Primates" J. Biol. Chem. 279:6213-6216 (2004).

(56) References Cited

OTHER PUBLICATIONS

Hirano et al., "Usefulness of CD4+CD45RBhigh CD25– Cell-Transferred SCID Mice for Preclinical Evaluation of Drugs for Inflammatory Bowel Disease" J Pharmacol Sci.;110(2):169-81, (Jun. 2009).
Hitzeman et al., "Isolation and characterization of the yeast 3-phosphoglycerokinase gene (PGK) by an immunological screening technique." J. Biol. Chem., 255:2073 (1980).
Hoffman et al. "Mutation of a new gene encoding a putative pyran-like protein causes familial cold autoinflammatory syndrome and Muckle-Wells syndrome" Nature 29:301-305 (2001).
Hoffman et al: "Efficacy and safety of rilonacept (interleukin-I trap) in patients with cryopyrin-associated periodic syndromes: Results from two sequential placebo-controlled studies", Arthritis & Rheumatism, vol. 58, No. 8, Jul. 30, 2008 (Jul. 30, 2008), pp. 2443-2452.
Holland et al, "Isolation and identification of yeast messenger ribonucleic acids coding for enolase, glyceraldehyde-3-phosphate dehydrogenase, and phosphoglycerate kinase <http://pubs.acs.org/doi/abs/10.1021/bi00616a007>" Biochemistry, 17:4900 (1978).
Holliger et al. ""Diabodies": small bivalent and bispecific antibody fragments." Proc Natl Acad Sci USA 90:6444-6448 (1993).
Hosse et al., "A new generation of protein display scaffolds for molecular recognition." Protein Science, 15:14-27 (2006).
Hou, et al., "Design of a superior cytokine antagonist for topical ophthalmic use" Eleven Biotheraputics,Inc., PNAS, vol. 110, No. 10, p. 3913-3918, Mar. 5, 2013.
Hynninen et al., "Interleukin 1 receptor antagonist and E-selectin concentrations: A comparison in patients with severe acute pancreatitis and severe sepsis", J. Crit Care., 14(2):63-68 (1999).
Ill et al, "Design and construction of a hybrid immunoglobulin domain with properties of both heavy and light chain variable regions" Protein Engineering (1997)10(8):949-957.
Imren et al. "Permanent and panerythroid correction of murine Beta thalassemia by multiple lentiviral integration in hematopoietic stem cells" PNAS 99:14380, (2002).
Inaba et al., "Expression of the antimicrobial peptide alpha-defensin/cryptdins in intestinal crypts decreases at the initial phase of intestinal inflammation in a model of inflammatory bowel disease, IL-10-deficient mice." Inflamm Bowel Dis., 16(9):1488-95 (Sep. 2010).
International Preliminary Report on Patentability and Written Opinion for PCT/US2012/022583 dated Jul. 30, 2013.
International Preliminary Report on Patentability and Written Opinion for PCT/US2012/048631 dated Feb. 4, 2014.
International Preliminary Report on Patentability and Written Opinion, International Application No. PCT/US2011/041588, dated Dec. 28, 2012.
International Preliminary Report on Patentability and Written Opinion, International Application No. PCT/US2011/045995, dated Jan. 29, 2013.
International Preliminary Report on Patentability and Written Opinion, International Application No. PCT/US2012/048631, dated Feb. 4, 2014.
International Search Report and Written Opinion for PCTUS2014026416 dated Jul. 17, 2014.
International Search Report for PCT/US08/09776, dated Feb. 26, 2009.
International Search Report for PCT/US2011/045995 dated Dec. 23, 2011.
International Search Report for PCT/US2012/022583 dated Jun. 9, 2012.
International Search Report for PCT/US2012/048631 dated Jan. 23, 2013.
International Search Report, International Application No. PCT/US2010/020646, dated Oct. 8, 2010.
International Search Report, International Application No. PCT/US2012/048631, dated Jan. 23, 2013.
Issekutz, et al., "Treatment of established adjuvant arthritis in rats with monoclonal antibody to CD18 and very late activation antigen-4 integrins suppresses neutrophil and T-lymphocyte migration to the joints and improves clinical disease" Immunology 88:569 (1996).
Janssens et al, "Generation of heavy-chain-only antibodies in mice" PNAS (2006) 103(41):15130-15135.
Jie et al. "Interleukin-1 Receptor Antagonist Eye Drops Promoting High-Risk Corneal Allografts Survival in Rats." Ch. Med. J. 117. 5(2004):711-716.
Jones et al., "Sjogren's syndrome: Cytokine and Epstein-Barr viral gene expression within the Conjunctival Epithelium", Invest. Ophtalmo/. Vis. Sci., 35(9):3493-3503 (1994).
Karlin et al., "Applications and statistics for multiple high-scoring segments in molecular sequences", PNAS USA 90, 5873-5787, (1993).
Kay, "Adenoviral Vectors for Hepatic Gene Transfer in Animals" Chest 111(6 Supp.):138S-142S, (1997).
Keane-Myers et al. "Prevention of Allergic Eye Disease by Treatment with IL-1 Receptor Antagonist" Invest Ophthalmol Vis Sci, 40(12): 3041-6, (1999).
Kluczyk A., et al., "Immunodulatory Activity of Oligopeptides Related to Interleukin 1 Receptor Antagonist Sequence," Arch. Immunol. Ther. Exp., 45(5-6):427-433 (1997).
Kluczyk, A., et al., "The two-headed peptide inhibitors of interleukin-1 action," Peptides, 21(9):1411-1420 (2000) (Abstract).
Kocak-Altintas et al., "Impression cytology and ocular characteristics in ocular rosacea", Eur. J. Opthalmol., 13:351-359 (2003).
Krelin et al. "Interleukin-1b-Driven Inflammation Promotes the Development and Invasiveness of Chemical Carcinogen-Induced Tumors" Cancer Res. 67:1062-1071, (2007).
Larsen, et al. "Interleukin-1-Receptor Antagonist in Type 2 Diabetes Mellitus" NEJM 356:1517-26, (2007).
Larsen, et al. "Sustained Effects of Interleukin-1 Receptor Antagonist Treatment in Type 2 Diabetes" Diabetes Care 32:1663-8, (2009).
Lee, et al. "Remission in models of type 1 diabetes by gene therapy using a single-chain insulin analogue." Nature 408:483-8 (2000).
Lust et al. "Induction of a Chronic Disease State in Patients With Smoldering or Indolent Multiple Myeloma by Targeting Interleukin 1Beta-Induced Interleukin 6 Production and the Myeloma Proliferative Component" Mayo Clin Proc 84(2)114-122, (2009).
Macsai. "The Role of Omega-3 Dietary Supplementation in Blephartitis and Meibomian Gland Dysfunction (an AOS Thesis)." Transactions of the American Ophthalmological Society. 106(2008):336-356.
Martin et al. "The affinity-selection of a minibody polypeptide inhibitor of human interleukin-6." EMBO J 13:5303-9 (1994).
Teoh et al., "Tailoring biological treatment: anakinra treatment of posterior uveitis associated with the CINCA syndrome", Br. J. Opthalmol., 91:263-264 (2007).
Thompson et al., "DbCustal: Rapid and reliable global multiple alignments of protein sequences detected by database searches", Nucl. Acids Res. 28, 2910-2926, (2000).
Thule, P. M. and Liu, J. M. "Regulated hepatic insulin gene therapy of STZ-diabetic rats." Gene Ther. 7:1744-52; (2000).
Tinubu et al., "Humanized antibody directed to the IL-2 receptor beta-chain prolongs primate cardiac allograft survival.", J. Immunol., 4330-4338, (1994).
Tomlinson et al. "Reshaping human antibodies for therapy" J. Mol. Biol. 227:776-798, (1992).
Tomlinson et al. "The structural repertoire of the human V kappa domain." EMBO J. 14(18):4628-38, (1995).
Traunecker et al. "Bispecific single chain molecules (Janusins) target cytotoxic lymphocytes on HIV infected cells." EMBO J 10:3655-3659 (1991).
Trittibach,et al. "Lentiviral-vector-mediated expression of murine IL-1 receptor antagonist or IL-10 reduces the severity of endotoxin-induced uveitis." Gene Ther. 15(22): 1478-88. (2008).
Tsai et al. "Suppression of experimental uveitis by a recombinant adeno-associated virus vector encoding interleukin-1 receptor antagonist." Mol Vis 15:1542-1552, (2009).
Urlaub et al., "Efficient cloning of single-copy genes using specialized cosmid vectors: Isolation of mutant dihydrofolate reductase genes" Proc. Natl. Acad. Sci. USA, 77:4216 (1980).

(56) References Cited

OTHER PUBLICATIONS

Urlinger, et al. "Exploring the sequence space for tetracyclinedependent transcriptional activators: Novel mutations yield expanded range and sensitivity" Proc. Natl. Acad. Sci. USA 97(14):7963-7968, (2000).
Vigers et al. "Crystal structure of the type-I interleukin-1 receptor complexed with interleukin-1 J3" Nature 386: 190-194, (1997).
Viti et al., "Design and use of phage display libraries for the selection of antibodies and enzymes", Methods Enzymol.; 326:480-505; 2000.
Voronov et al. "IL-1 is required for tumor invasiveness and angiogenesis" PNAS 100:2645-2650 (2003).
Wagner et al., "Nucleotide sequence of the thymidine kinase gene of herpes simplex virus type 1", Proc. Natl. Acad. Sci. US.A., 78(3):1441-1445 (1980).
Ware et al., Arthritis Impact Measurement Scales or Arthritis Impact Measurement Scales 2, Med. Care. 37(5 Suppl): MS40-50, AIMS or AIMS2, (1999).
Watari et al. "Role of macrophages in inflammatory lymphangiogenesis: Enhanced production of vascular endothelial growth factor C and D through NF-kappaB activation" Biochem Biophys Res Commun (2008) vol. 377 No. 3 pp. 826-831.
Wells et al., "Cassette mutagenesis: an effkient method for generation of multiple mutations at defined sites" Gene, 34:315, (1985).
Wieczorek, Z., et al., "A Hexapeptide VTKFYF from C-terminal Part of Interleukin-1 Receptor Antagonist, an Inhibitor of IL-1—IL-1 Receptor Interaction," Polish Journal of Pharmacology, 49:107-117 (1997).
Wieczorek, Z., et al., "The Search for Inhibitors of Interleukin-1 Based on the Sequence of Interleukin-1 Receptor Antagonist," Biomed Pept. Proteins Nucleic Acids, 2(4):123-129 (1996-1997) (Abstract).
Wingren: "Fusion of a Signal Sequence to the Interleukin-1beta Gene Directs the Protein from Cytoplasmic Accumulation to Extracellular Release", Cellular Immunology, Vo 1. 169, No. 2, May 1, 1996 (May 1, 1996), p. 226-237.
Xu et al. "Decrease in the Corneal Sensitivity and Change in Tear Function in Dry Eye" Cornea.15.3(1996):235-239 (Abstract).
Yamada et al. "Interleukin 1 Receptor Antagonist Suppresses Allosensitization in Corneal Transplantation." Arch. Ophthlmol. 116(1998):1351-1357.
Yamada et al., "Interleukin-1 receptor antagonist therapy and induction of anterior chamber-associated immune deviation-type tolerance after corneal transplantation", Invest. Opthalmol. Vis. Sci., 41 :4203-4208 (2000).
Yamada et al., "Local suppression of IL-I by receptor antagonist in the rat model of corneal alkali injury", Exp. Eye Res., 76:161-167 (2003).
Yamasaki et al., "Interleukin-1 as a pathogenetic mediator of ischemic brain damage in rats", Stroke, 26:676-681 (1995).
Yang, "Gene Transfer into Mammalian Somatic Cells in Vivo" Crit. Rev. Biotechnol. 12:335-56, (1992).
Zoller et al., "Oligonucleotide-directed mutagenesis using M13-derived vectors: an efficient and general procedure for the production of point mutations in any fragment of DNA" Nucl. Acids Res., 10:6487, (1987).
Özcura, "Ocular Surface Disease Index for the Diagnosis of Dry Eye Syndrome" Ocul Immunol Inflamm.15(5):389-93 ,(Sep.-Oct. 2007).
Aksentijevich et al. "De novo CIAS1 mutations, cytokine activation, and evidence for genetic heterogeneity in patients with neonatal-onset multisystem inflammatory disease (NOMID): a new member of the expanding family of pyrin-associated autoinflammatory diseases" Arthritis Rheum 46:3340-3348, (2002).
Akuzawa et al. "Interleukin-1 Receptor Antagonist Attenuates the Severity of Spinal Cord Ischemic Injury in Rabbits." J. Vascular Surg. 48.3(2008):694-700.
Alt et al., "Liver-directed gene therapy: molecular tools and current preclinical and clinical studies" J. Hepatol. 23:746-58; (1995).

Altschul et al., "Basic local alignment search tool" J. Mol. Biol. 215, 403-410, (1990).
Altschul et al., "Local alignment statistics", Methods in Enzymology 266, 460-480, (1996).
Ansel et al., Pharmaceutical Dosage Forms and Drug Delivery Systems, 7th Ed.., Lippincott Williams & Wilkins Publishers (1999).
Antin et al., "Recombinant human interleukin-1 receptor antagonist in the treatment of steroid-resistant graftversus-host disease", Blood, 84:1342-1348 (1994).
Arend, W.P., "Interleukin-1 Receptor Antagonist", Adv. Immunol., 54:167-223 (1993).
Arnold et al., "The impact of glycosylation on the biological function and structure of human immunoglobulins." Ann. Rev. Immunol. 25: 21-50 (2007).
Baker et al., "Protein structure prediction and structural genomics" Science 294(5540):93-6, 2001).
Barbino et al., "The Controlled-Environment Chamber: A New Mouse Model of Dry Eye" Invest. Ophthal. Vis. Sci., 46: 2766-2711 (2005).
Bardwell et al., Rheumatoid Arthritis Severity Scale: a brief, physician-completed scale not confounded by patient self-report of psychological functioning Rheumatology 41(1):38-45, (2002).
Barton et al., "Inflammatory cytokines in the tears of patients with ocular rosacea", Opthalmol., 104:1868-1874 (1997).
Battat et al. "Effects of Laser in Situ Keratomileusis on Tear Production, Clearance, and the Ocular Surface" Ophthalmol. 108(2001):1230-1235.
Benoist et al., "In vivo sequence requirements of the sv40 early promoter region", Nature, 290:304-310 (1981).
Berge, et al. "Pharmaceutical salts." J. Pharm. Sci. 66:1-19, (1977).
Beyer et al., "Crystal structures of the pro-inflammatory cytokine interleukin-23 and its complex with a high-affinity neutralizing antibody." J. Mol. Biol. (2008).
Biswas et al. "Counteracting Corneal Immunoinflammatory Lesion with Interleukin-1 Receptor Antagonist Protein." J. Leukocyte Bioi. 76(2004):868-875.
Boder et al., "Yeast surface display for directed evolution of protein expression, affinity, and stability." Methods Enzymol.;328:430-44, (2000).
Bolton, "Recent advances in the pharmacological control of experimental allergic encephalomyelitis (EAE) and the implications for multiple sclerosis treatment", Multiple Sclerosis, 143, (1995).
Boraschi et al. "Structure-function relationship in the IL-1 family" Frontiers in Bioscience: A Journal and Virtual Library 1, d270-308, (1996).
Boraschi, "Mapping of receptor binding sites on IL-1 beta by reconstruction of IL-1ra-like domains" J. Immunol., 155 (10):4719-25 (1995).
Bresnihan et al., "Interleukin-1 receptor antagonist", Rheum. Dis. Clin. North Am,., 24(3):615-628 (1998).
Brignole et al., "Flow cytobetric analysis of inflammatory markers in conjunctival epithelial cells of patients with dry eyes", Invest. Ophtalmol. Vis. Sci., 41(6):1356-1362 (2000).
Brinster et al., "Regulation of metallothionein-thymidine kinase fusion plasmids injected into mouse eggs", Nature, 296:39-42 (1982).
Brody, et al. "Adenovirus-mediated in vivo gene transfer" Ann. N.Y. Acad. Sci. 716:90-101; (1994).
Bron et al., "The Contribution of Meibomian Disease to Dry Eye", Ocul. Surf., 2:149-165 (2004).
Caron et al., "Chondroprotective effect of intraarticular injections of interleukin-1 receptor antagonist in experimental osteoarthritis", Arthritis Rheum., 39:1535-1544 (1996).
Carter et al., "Improved oligonucleotide site-directed mutagenesis using M13 vectors" Nucl. Acids Res.,13:4331, (1986).
Case et al. "The Amber biomolecular simulation programs." J. Computat. Chem. 26, 1668-1688, (2005).
Case et al., AMBER 11, University of California, San Francisco, CA USA, (2010).
Cavanagh et al. "The Molecular Basis of Neurotrophic Keratitis." Acta Ophthamol.67.S19i(1989):115-134.
Chang et al., "Phenotypic expression in *E. coli* of a DNA sequence coding for mouse dihydrofolate reductase" Nature, 275:615 (1978).

(56) References Cited

OTHER PUBLICATIONS

Chang et al: Dual Biological Functions of an Interleukin-1 Receptor Antagonist-Interleukin-10 Fusion Protein and Its Suppressive Effects on Joint Inflamation, Immunology, vol. 1. 112, No. 4, Aug. 1, 2004 (Aug. 1, 2004), p. 643-650.
Chao et al. "Isolating and engineering human antibodies using yeast surface display" Nat Protoc.1(2):755-68, (2006).
Chothia et al. "Canonical structures for the hypervariable regions of immunoglobulins." J. Mol. Biol. 196:901-917, (1987).
Chothia et al., "Structural repertoire of the human VH segments.", J. Mol. Biol. 227:799-817, (1992).
Chothia, "The nature of the accessible and buried surfaces in proteins" J. Mol. Biol., 150:1 1-12, (1976).
Cohen, et al. "Treatment of rheumatoid arthritis with anakinra, a recombinant human interleukin-1 receptor antagonist, in combination with methotrexate: results of a twenty-four-week, multicenter, randomized, double-blind, placebo-controlled trial" Arthritis & Rheumatism 46, 614-24 (2002).
Colby et al. "Engineering antibody affinity by yeast surface display" Methods Enzymol., 388:348-58, (2004).
Current Protocols in Immunology, Unit 15.1; John Wiley & Sons, Inc. (2009).
Current Protocols in Immunology, Unit 15.2; John Wiley & Sons, Inc. (2009).
Current Protocols in Immunology, Unit 15.5; John Wiley & Sons, Inc. (2009).
Current Protocols in Immunology, Unit 4.4; John Wiley & Sons, Inc, (1995).
Current Protocols in Molecular Biology, Greene Publishing Associates, Sections 9.10, (1989).
Current Protocols in Molecular Biology, Greene Publishing Associates, Sections 9.11, (1989).
Current Protocols in Molecular Biology, Greene Publishing Associates, Sections 9.12, (1989).
Current Protocols in Molecular Biology, Greene Publishing Associates, Sections 9.13, (1989).
Current Protocols in Molecular Biology, Greene Publishing Associates, Sections 9.14, (1989).
Current Protocols in Molecular Biology, John Wiley & Sons, N. Y., 6.3.1-6.3.6, (1989).

* cited by examiner

```
                          SEQUENCE LISTING

<160> NUMBER OF SEQ ID NOS: 23

<210> SEQ ID NO 1
   <211> LENGTH: 153
   <212> TYPE: PRT
   <213> ORGANISM: Artificial Sequence
   <220> FEATURE:
   <223> OTHER INFORMATION: Description of Artificial Sequence: Synthetic
         polypeptide

<400> SEQUENCE: 1

Ala Pro Val Arg Ser Leu Ala Phe Arg Ile Trp Asp Val Asn Gln Lys
   1               5                   10                  15

Thr Phe Tyr Leu Arg Asn Asn Gln Leu Val Ala Gly Tyr Leu Gln Gly
                   20                  25                  30

Pro Asn Val Asn Leu Glu Glu Lys Ile Asp Val Ser Phe Val Gln Gly
               35                  40                  45

Glu Glu Ser Asn Asp Lys Ile Pro Val Ala Leu Gly Ile His Gly Gly
           50                  55                  60

Lys Met Cys Leu Ser Cys Val Lys Ser Gly Asp Glu Thr Arg Leu Gln
   65                  70                  75                  80

Leu Glu Ala Val Asp Pro Lys Asn Tyr Pro Lys Lys Met Asp Lys
                       85                  90                  95

Arg Phe Ala Phe Ile Arg Ser Asp Ser Gly Pro Thr Thr Ser Phe Glu
                   100                 105                 110

Ser Ala Ala Cys Pro Gly Trp Phe Leu Cys Thr Ala Met Glu Ala Asp
               115                 120                 125

Gln Pro Val Ser Leu Thr Asn Met Pro Asp Glu Gly Val Met Val Thr
           130                 135                 140

Lys Phe Tyr Met Gln Phe Val Ser Ser
   145                 150

<210> SEQ ID NO 2
   <211> LENGTH: 153
   <212> TYPE: PRT
   <213> ORGANISM: Artificial Sequence
   <220> FEATURE:
   <223> OTHER INFORMATION: Description of Artificial Sequence: Synthetic
         polypeptide

<400> SEQUENCE: 2

Ala Pro Val Arg Ser Leu Ala Phe Arg Ile Trp Asp Val Asn Gln Lys
   1               5                   10                  15

Thr Phe Tyr Leu Arg Asn Asn Gln Leu Val Ala Gly Tyr Leu Gln Gly
```

```
            20                  25                  30
Pro Asn Val Asn Leu Glu Glu Lys Ile Asp Val Ser Phe Val Gln Gly
            35                  40                  45
Glu Glu Ser Asn Asp Lys Ile Pro Val Ala Leu Gly Ile His Gly Gly
        50                  55                  60
Lys Met Cys Leu Ser Cys Val Lys Ser Gly Asp Glu Thr Arg Leu Gln
65                  70                  75                  80
Leu Glu Ala Val Asp Pro Lys Asn Tyr Pro Lys Lys Met Glu Lys
                85                  90                  95
Arg Phe Val Phe Asn Lys Ile Glu Ile Asn Asn Lys Leu Ser Phe Glu
                    100                 105                 110
Ser Ala Ala Cys Pro Gly Trp Phe Leu Cys Thr Ala Met Glu Ala Asp
            115                 120                 125
Gln Pro Val Ser Leu Thr Asn Met Pro Asp Glu Gly Val Met Val Thr
        130                 135                 140
Lys Phe Tyr Met Gln Phe Val Ser Ser
145                 150
```

<210> SEQ ID NO 3
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Ala Pro Val Arg Ser Leu Ala Phe Arg Ile Trp Asp Val Asn Gln Lys
1               5                   10                  15
Thr Phe Tyr Leu Arg Asn Asn Gln Leu Val Ala Gly Tyr Leu Gln Gly
                20                  25                  30
Pro Asn Val Asn Leu Glu Glu Lys Phe Ser Met Ser Phe Val Gln Gly
            35                  40                  45
Glu Glu Ser Asn Asp Lys Ile Pro Val Ala Leu Gly Leu Lys Glu Lys
        50                  55                  60
Asn Leu Tyr Leu Ser Cys Val Leu Lys Asp Asp Lys Pro Thr Leu Gln
65                  70                  75                  80
Leu Glu Ser Val Asp Pro Lys Asn Tyr Pro Lys Lys Met Glu Lys
                85                  90                  95
Arg Phe Val Phe Ile Arg Ser Asp Ser Gly Pro Thr Thr Ser Phe Glu
                    100                 105                 110
Ser Ala Ala Cys Pro Gly Trp Phe Leu Cys Thr Ala Met Glu Ala Asp
            115                 120                 125
Gln Pro Val Ser Leu Thr Asn Met Pro Asp Glu Gly Val Met Val Thr
        130                 135                 140
Lys Phe Thr Met Gln Phe Val Ser Ser
145                 150
```

<210> SEQ ID NO 4
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ala Pro Val Arg Ser Leu Ala Phe Arg Ile Trp Asp Val Asn Gln Lys
```

```
            1               5                  10                 15
Thr Phe Tyr Leu Arg Asn Asn Gln Leu Val Ala Gly Tyr Leu Gln Gly
            20                 25                 30

Pro Asn Val Asn Leu Glu Glu Lys Phe Ser Met Ser Phe Val Gln Gly
            35                 40                 45

Glu Glu Ser Asn Asp Lys Ile Pro Val Ala Leu Gly Leu Lys Glu Lys
        50                 55                 60

Asn Leu Tyr Leu Ser Cys Val Leu Lys Asp Asp Lys Pro Thr Leu Gln
65                  70                 75                  80

Leu Glu Ser Val Asp Pro Lys Asn Tyr Pro Lys Lys Met Glu Lys
                85                 90                 95

Arg Phe Val Phe Asn Lys Ile Glu Ile Asn Asn Lys Leu Glu Phe Glu
            100                105                110

Ser Ala Ala Cys Pro Gly Trp Phe Leu Cys Thr Ala Met Glu Ala Asp
            115                120                125

Gln Pro Val Ser Leu Thr Asn Met Pro Asp Glu Gly Val Met Val Thr
            130                135                140

Lys Phe Thr Met Gln Phe Val Ser Ser
145                 150
```

<210> SEQ ID NO 5
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Ala Pro Val Arg Ser Leu Asn Cys Arg Ile Trp Asp Val Asn Gln Lys
1               5                  10                 15

Thr Phe Tyr Leu Arg Asn Asn Gln Leu Val Ala Gly Tyr Leu Gln Gly
            20                 25                 30

Pro Asn Val Asn Leu Glu Glu Lys Phe Ser Met Ser Phe Val Gln Gly
            35                 40                 45

Glu Glu Ser Asn Asp Lys Ile Pro Val Ala Leu Gly Leu Lys Glu Lys
        50                 55                 60

Asn Leu Tyr Leu Ser Cys Val Leu Lys Asp Asp Lys Pro Thr Leu Gln
65                  70                 75                  80

Leu Glu Ser Val Asp Pro Lys Asn Tyr Pro Lys Lys Met Glu Lys
                85                 90                 95

Arg Phe Val Phe Asn Lys Ile Glu Ile Asn Asn Lys Leu Glu Phe Glu
            100                105                110

Ser Ala Gln Phe Pro Asn Trp Phe Leu Cys Thr Ala Met Glu Ala Asp
            115                120                125

Gln Pro Val Ser Leu Thr Asn Met Pro Asp Glu Gly Val Met Val Thr
            130                135                140

Lys Phe Tyr Met Gln Phe Val Ser Ser
145                 150
```

<210> SEQ ID NO 6
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Ala Pro Val Arg Ser Leu Asn Cys Thr Leu Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Glu Gln Gln Val Phe Ser Met Ser Phe Val Gln Gly
        35                  40                  45

Glu Glu Ser Asn Asp Lys Ile Pro Val Ala Leu Gly Leu Lys Glu Lys
50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Tyr Ile Ser Thr Ser Met Glu Ala Asp
            115                 120                 125

Gln Pro Val Phe Leu Gly Gly Thr Lys Gly Gly Gln Asp Ile Thr Asp
        130                 135                 140

Phe Thr Met Gln Phe Val Ser Ser
145                 150
```

<210> SEQ ID NO 7
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
            115                 120                 125

Gln Pro Val Ser Leu Thr Asn Met Pro Asp Glu Gly Gln Asp Ile Thr
        130                 135                 140

Asp Phe Thr Met Gln Phe Val Ser Ser
145                 150
```

<210> SEQ ID NO 8
<211> LENGTH: 459
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 8

```
gcacctgtac gatcactggc cttcagaatc tgggatgtta accagaagac cttctatctg    60
aggaacaacc aactagttgc tggatacttg caaggaccaa atgtcaattt agaagaaaag   120
atagatgtgt cctttgtaca aggagaagaa agtaatgaca aaatacctgt ggccttgggc   180
atccatggag ggaagatgtg cctgtcctgt gtcaagtctg gtgatgagac cagactccag   240
ctggaggcag ttgatcccaa aaattaccca agaagaagaa tggacaagcg cttcgccttc   300
atccgctcag acagcggccc caccaccagt tttgagtctg ccgcctgccc cggttggttc   360
ctctgcacag cgatggaagc tgaccagccc gtcagcctca ccaatatgcc tgacgaaggc   420
gtcatggtca ccaaaattcta catgcaattt gtgtcttcc                         459
```

<210> SEQ ID NO 9
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gcacctgtac gatcactggc cttcagaatc tgggatgtta accagaagac cttctatctg    60
aggaacaacc aactagttgc tggatacttg caaggaccaa atgtcaattt agaagaaaag   120
atagatgtgt cctttgtaca aggagaagaa agtaatgaca aaatacctgt ggccttgggc   180
atccatggag ggaagatgtg cctgtcctgt gtcaagtctg gtgatgagac cagactccag   240
ctggaggcag ttgatcccaa aaattaccca agaagaagaa tggaaaagcg atttgtcttc   300
aacaagatag aaatcaataa caagctgagt tttgagtctg ccgcctgccc cggttggttc   360
ctctgcacag cgatggaagc tgaccagccc gtcagcctca ccaatatgcc tgacgaaggc   420
gtcatggtca ccaaaattcta catgcaattt gtgtcttcc                         459
```

<210> SEQ ID NO 10
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gcacctgtac gatcactggc cttcagaatc tgggatgtta accagaagac cttctatctg    60
aggaacaacc aactagttgc tggatacttg caaggaccaa atgtcaattt agaagaaaag   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaagaa tggaaaagcg atttgtcttc   300
atccgctcag acagcggccc caccaccagt tttgagtctg ccgcctgccc cggttggttc   360
ctctgcacag cgatggaagc tgaccagccc gtcagcctca ccaatatgcc tgacgaaggc   420
gtcatggtca ccaaaattcac catgcaattt gtgtcttcc                         459
```

<210> SEQ ID NO 11
<211> LENGTH: 459
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 11
gcacctgtac gatcactggc cttcagaatc tgggatgtta accagaagac cttctatctg    60
aggaacaacc aactagttgc tggatacttg caaggaccaa atgtcaattt agaagaaaag   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaagaa tggaaaagcg atttgtcttc   300
aacaagatag aaatcaataa caagctggaa tttgagtctg ccgcctgccc cggttggttc   360
ctctgcacag cgatggaagc tgaccagccc gtcagcctca ccaatatgcc tgacgaaggc   420
gtcatggtca ccaaattcac catgcaattt gtgtcttcc                          459

<210> SEQ ID NO 12
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gcacctgtac gatcactgaa ctgcagaatc tgggatgtta accagaagac cttctatctg    60
aggaacaacc aactagttgc tggatacttg caaggaccaa atgtcaattt agaagaaaag   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaagaa tggaaaagcg atttgtcttc   300
aacaagatag aaatcaataa caagctggaa tttgagtctg cccagttccc caactggttc   360
ctctgcacag cgatggaagc tgaccagccc gtcagcctca ccaatatgcc tgacgaaggc   420
gtcatggtca ccaaattcta catgcaattt gtgtcttcc                          459

<210> SEQ ID NO 13
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gcacctgtac gatcactgaa ctgcacgctc tgggatgtta accagaagac cttctatctg    60
aggaacaacc aactagttgc tggatacttg caaggaccaa atgtcgagca acaagtggtg   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaagaa tggaaaagcg atttgtcttc   300
aacaagatag aaatcaataa caagctggaa tttgagtctg cccagttccc caactggtac   360
atcagcacct ctatggaagc tgaccagccc gtcttcctgg gagggaccaa aggcggccag   420
gatataactg acttcaccat gcaatttgtg tcttcc                             456

<210> SEQ ID NO 14
```

<211> LENGTH: 459
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
gcacctgtac gatcactgaa ctgcagaatc tgggatgtta accagaagac cttctatctg    60
aggaacaacc aactagttgc tggatacttg caaggaccaa atgtcaattt agaagaaaag   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaagaa tggaaaagcg atttgtcttc   300
aacaagatag aaatcaataa caagctggaa tttgagtctg cccagttccc caactggttc   360
ctctgcacag cgatggaagc tgaccagccc gtcagcctca ccaatatgcc tgacgaaggc   420
caggatataa ctgacttcac catgcaattt gtgtcttcc                          459
```

<210> SEQ ID NO 15
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Ala Pro Val Arg Ser Leu Ala Phe Arg Ile Trp Asp Val Asn Gln Lys
1               5                   10                  15
Thr Phe Tyr Leu Arg Asn Asn Gln Leu Val Ala Gly Tyr Leu Gln Gly
            20                  25                  30
Pro Asn Val Asn Leu Glu Glu Lys Phe Ser Met Ser Phe Val Gln Gly
        35                  40                  45
Glu Glu Ser Asn Asp Lys Ile Pro Val Ala Leu Gly Leu Lys Glu Lys
    50                  55                  60
Asn Leu Tyr Leu Ser Cys Val Leu Lys Asp Asp Lys Pro Thr Leu Gln
65                  70                  75                  80
Leu Glu Ser Val Asp Pro Lys Asn Tyr Pro Lys Lys Met Glu Lys
                85                  90                  95
Arg Phe Val Phe Asn Lys Ile Glu Ile Asn Asn Lys Leu Glu Phe Glu
            100                 105                 110
Ser Ala Gln Phe Pro Asn Trp Phe Leu Cys Thr Ala Met Glu Ala Asp
        115                 120                 125
Gln Pro Val Ser Leu Thr Asn Met Pro Asp Glu Gly Val Met Val Thr
    130                 135                 140
Lys Phe Tyr Met Gln Phe Val Ser Ser
145                 150
```

<210> SEQ ID NO 16
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Ala Pro Val Arg Ser Gln Ala Phe Arg Ile Trp Asp Val Asn Gln Lys
1               5                   10                  15
```

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
                115                 120                 125

Gln Pro Val Ser Leu Thr Asn Met Pro Asp Glu Gly Val Met Val Thr
            130                 135                 140

Lys Phe Tyr Met Gln Phe Val Ser Ser
145                 150

<210> SEQ ID NO 17
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Ile Asp Val Ser Phe Val Gln Gly
        35                  40                  45

Glu Glu Ser Asn Asp Lys Ile Pro Val Ala Leu Gly Leu Lys Glu Lys
50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
                115                 120                 125

Gln Pro Val Ser Leu Thr Asn Met Pro Asp Glu Gly Val Met Val Thr
            130                 135                 140

Lys Phe Tyr Met Gln Phe Val Ser Ser
145                 150

<210> SEQ ID NO 18
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Ile Asp Val Ser Phe Val Gln Gly
            35                  40                  45

Glu Glu Ser Asn Asp Lys Ile Pro Val Ala Leu Gly Leu Lys Glu Lys
        50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
                100                 105                 110

Ser Ala Gln Phe Pro Asn Trp Phe Leu Cys Thr Ala Met Glu Ala Asp
            115                 120                 125

Gln Pro Val Ser Leu Thr Asn Met Pro Asp Glu Gly Val Met Val Thr
            130                 135                 140

Lys Phe Tyr Met Gln Phe Val Ser Ser
145                 150

<210> SEQ ID NO 19
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
            35                  40                  45

Glu Glu Ser Asn Asp Lys Ile Pro Val Ala Leu Gly Leu Lys Glu Lys
        50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Lys Met Glu Lys
                85                  90                  95

Arg Phe Val Phe Asn Lys Ile Glu Ile Asn Asn Lys Leu Glu Phe Glu
                100                 105                 110

Ser Ala Gln Phe Pro Asn Trp Phe Leu Cys Thr Ala Met Glu Ala Asp
            115                 120                 125

Gln Pro Val Ser Leu Thr Asn Met Pro Asp Glu Gly Val Met Val Thr
            130                 135                 140

Lys Phe Thr Met Gln Phe Val Ser Ser
145                 150

<210> SEQ ID NO 20
<211> LENGTH: 151
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 20

Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp
145                 150

<210> SEQ ID NO 21
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp
145                 150

<210> SEQ ID NO 22
<211> LENGTH: 165
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 22

Ser Ala Pro Phe Ser Phe Leu Ser Asn Val Lys Tyr Asn Phe Met Arg
1               5                   10                  15

Ile Ile Lys Tyr Glu Phe Arg Ile Trp Asp Val Asn Gln Lys Thr Phe
            20                  25                  30

Tyr Leu Arg Asn Asn Gln Leu Val Ala Gly Tyr Leu Gln Gly Pro Asn
        35                  40                  45

Val Asn Leu Glu Glu Lys Phe Asp Met Gly Ala Tyr Lys Ser Ser Lys
    50                  55                  60

Asp Asp Ala Lys Ile Thr Val Ile Leu Arg Ile Ser Lys Thr Gln Leu
65                  70                  75                  80

Tyr Val Thr Ala Gln Asp Glu Asp Gln Pro Val Leu Leu Lys Glu Met
                85                  90                  95

Pro Glu Ile Pro Lys Thr Ile Thr Gly Ser Glu Thr Asn Leu Leu Phe
            100                 105                 110

Phe Trp Glu Thr His Gly Thr Lys Asn Tyr Phe Thr Ser Val Ala His
            115                 120                 125

Pro Asn Leu Phe Leu Cys Thr Ala Met Glu Ala Asp Gln Pro Val Ser
        130                 135                 140

Leu Thr Asn Met Pro Asp Glu Gly Val Met Val Thr Lys Phe Tyr Ile
145                 150                 155                 160

Leu Glu Asn Gln Ala
                165

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```

CHIMERIC CYTOKINE FORMULATIONS FOR OCULAR DELIVERY

RELATED APPLICATIONS

This application is a continuation of U.S. patent application Ser. No. 14/209,605, filed Mar. 13, 2014, which claims priority to U.S. Provisional Application No. 61/779,974, filed Mar. 13, 2013, the entire contents of which are hereby incorporated in their entirety.

FIELD OF THE INVENTION

The present invention relates to therapeutic compositions and formulations, e.g., for IL-1 inhibitors.

BACKGROUND

Interleukin-1 alpha (IL-1α) and beta (IL-1β) are members of the IL-1 family of immunoregulatory cytokines. At least eleven human members of the interleukin-1 cytokine family have been identified, nine putative or demonstrated agonists (IL-1α, IL-1β, IL-18, IL-36α (IL-1F6), IL-36β ((IL-1F8), IL-36γ (IL-1F9), IL-33, IL-1F7 and IL-1F10) and two natural antagonists (IL-1Ra and IL36Ra (IL-1F5)).

IL-1a and IL-1β have roles in regulating the immune system, and have been implicated in inflammatory ophthalmic diseases, including significant inflammatory ocular disorders. Thus, there is a need for better methods and materials for ocular administration of IL-1 inhibitory agents.

Anakinra (Kineret®, Amgen, Thousand Oaks, Calif.), a recombinant IL1-Ra molecule, is approved for use in treating rheumatoid arthritis and Cryopyrin-Associated Periodic Syndromes (CAPS) called Neonatal-Onset Multisystem Inflammatory Disease (NOMID). It is supplied as a single use, glass syringe with 27 gauge needles as a sterile, clear, colorless-to-white, preservative-free solution for daily subcutaneous administration. Kineret® is formulated in 0.67 ml solution with pH 6.5, containing 100 mg anakinra, 1.29 mg sodium citrate, 5.48 mg sodium chloride, 0.12 mg disodium EDTA, and 0.70 mg polysorbate 80 in water for injection. Storage at 2-8° C. is advised. Kineret® is not approved for ocular administration.

SUMMARY

Featured herein are stable formulations (e.g., stable aqueous formulations) containing chimeric cytokines (e.g., chimeric cytokines or chimeric cytokine domains as described in WO2012/016203 or in WO 2012/103240) that can be used, inter alia, to modulate cellular signalling responsive to IL-1 family cytokines and their respective receptors, to treat disorders, and to detect and/or bind to cellular receptors, as well as other agents. Described herein is a pharmaceutical formulation that includes 1 mg/ml to 50 mg/ml of an IL-1β/IL-1Ra chimeric cytokine protein. In embodiments, the pharmaceutical formulation comprises 1 mg/ml to 50 mg/ml of an IL-1β/IL-1Ra chimeric cytokine protein; a surfactant; a tonicity agent; and a buffering agent.

In some aspects, the chimeric cytokine protein is P05 or another chimeric cytokine such as, e.g., those described in WO2012/016203 or WO 2012/103240. In embodiments, the formulation is for topical administration. In embodiments, the formulation is for administration to the eye. In embodiments, the formulation is for topical administration to the eye. In some embodiments, the formulation has a pH of 5.5 to 7.5, for example a pH of 6.0 to 7.0.

In embodiments, the formulation does not contain a viscosity agent. Certain embodiments relate to a formulation that also contains a viscosity agent. In embodiments, the viscosity agent is a sodium carboxymethyl cellulose; an hydroxy ethyl cellulose; an hydroxypropyl methylcellulose; a polyvinyl alcohol; and/or a glycerin. In embodiments, sodium carboxymethyl cellulose is included in the formulation at a concentration of 0.1-6% w/v.

The formulation typically has a purity of at least 90%, 93%, 95%, or 98% after storage for at least 60 days at 25° C. In some aspects, the formulation has a purity of at least 90%, 93%, 95%, or 98% after storage for at least four months at 25° C. In other aspects, the formulation has a purity of at least 90% after storage for a period of at least 2 weeks at 40° C. In some cases, the formulation is stable for at least two years when stored at 2° C. to 8° C. In some cases the formulation is stable for at least six months when stored at 25° C. In some cases the formulation is stable for at least eight months when stored at 25° C.

In some embodiments, the surfactant is a non-ionic surfactant, for example, pluronic acid F-68 (poloxamer 188), polysorbate-20, or polysorbate-80. In embodiments, the surfactant is pluronic acid F-68 (poloxamer 188), and the surfactant is present in a concentration of about 0.1% w/v. In some cases, the surfactant is pluronic acid F-68 (poloxamer 188), and the surfactant is present in a concentration of 0.1% w/v.

The tonicity agent in a formulation can be, for example, sodium chloride, sorbitol, mannitol, sucrose, or trehalose. In embodiments, the tonicity agent is sorbitol, and the sorbitol is present in a concentration of about 5% w/v. In certain embodiments, the tonicity agent is sorbitol, and the sorbitol is present in a concentration of 5% w/v.

The buffering agent in the formulation is generally a weak buffering agent. In embodiments, the buffering agent is a phosphate a citrate, an acetate, a borate, and/or a succinate. The buffering agent can be a pharmaceutically acceptable salt of a phosphate, a citrate, an acetate, a borate, or a succinate. In some embodiments, the buffering agent is present in an amount of from about 10 mM to about 50 mM. In embodiments, the buffering agent is present at a concentration of 20 mM or less. In embodiments, the buffering agent, e.g., the sodium citrate and/or sodium phosphate, is present at a total concentration of 5-15 mM. In some embodiments, the buffering agent, e.g., sodium citrate, is present at a concentration of 5-15 mM, 7-13 mM, 8-12 mM, or 9-11 mM.

In some cases, the buffering agent is sodium citrate and is present in the formulation at a concentration of about 10 mM. In some cases, the buffering agent is sodium citrate and is present in the formulation at a concentration of 10 mM.

In certain embodiments, the formulation includes an IL-1β/IL-1Ra chimeric cytokine protein such as P05; 10 mM sodium citrate; 5% w/v sorbitol; and 0.1% w/v poloxamer 188 (poloxamer F-68), and the pH of the formulation is 6.0.

In some embodiments, the formulation further includes an amino acid. For example, the amino acid is arginine, glutamic acid, histidine, or methionine.

In one example, a chimeric cytokine (e.g., a chimeric cytokine polypeptide), e.g., a chimeric cytokine containing sequences derived from an Il-1β and an IL-1Ra, is formulated at concentrations of 5 mg/ml to 20 mg/ml (e.g., at a concentration of 1 mg/ml, 5 mg/ml, or 20 mg/ml) in 10 mM sodium citrate, pH 6.0 containing 5% w/v sorbitol and 0.1% w/v poloxamer, e.g., poloxamer 188 (also referred to as, for example, Lutrol® F-68 (also referred to herein as Lutrol®), Kolliphor® P 188, and poly(ethylene glycol)-block-poly (ethylene glycol)). In embodiments, the chimeric cytokine is selected from one or more of P01, P02, P03, P04, P05, P06, and P07. In embodiments, the chimeric cytokine is P05.

In embodiments, the components of a formulation described herein are present in amounts that may vary around the values provided herein by up to 5%, 10%, 15%, 20%, 25%, 30%, 40%, or 50%. In embodiments, the components of a formulation are present in amounts that vary around the values provided herein by 10%. In embodiments, the formulation comprises 9.5-10.5 mM, 9-11 mM, 8.5-11.5 mM, 8-12 mM, 7.5-12.5 mM, 7-13 mM, 6-14 mM, or 5-15 mM sodium citrate. In embodiments, the formulation comprises 4.75-5.25%, 4.5-5.5%, 4.25-5.75%, 4-6%, 3.75-6.25%, 3.5-6.5%, 3-7%, or 2.5-7.5% w/v sorbitol. In embodiments, the formulation comprises 0.095-0.105%, 0.09-0.11%, 0.085-0.115%, 0.08-0.12%, 0.075-0.125%, 0.07-0.13%, 0.06-0.14%, or 0.05-0.15% w/v poloxamer 188. In embodiments, the concentration of the therapeutic protein (e.g., the chimeric cytokine, e.g., P05) in the formulation is 1-50 mg/ml, 1-25 mg/ml, or 1-20 mg/ml. In embodiments, the concentration of the therapeutic protein is 4.75-5.25 mg/ml, 4.5-5.5 mg/ml, 4.25-5.75 mg/ml, 4-6 mg/ml, 3.75-6.25 mg/ml, 3.5-6.5 mg/ml, 3-7 mg/ml, or 2.5-7.5 mg/ml. In embodiments, the pH of the formulation is 5.5 to 7.5, or 5.5 to 6.5.

In embodiments, the formulation comprises 8-12 mM sodium citrate, 4-6% w/v sorbitol, 0.08-0.12% w/v poloxamer 188, and 4-6 mg/ml P05. In embodiments, the pH of the formulation is 5.5 to 7.5. In embodiments, the pH is 5.5 to 6.5. In embodiments, the pH is 6 to 7.

In embodiments, the formulation comprises 9-11 mM sodium citrate, 4.5-5.5% w/v sorbitol, 0.09-0.11% w/v poloxamer 188, and 4.5-5.5 mg/ml P05. In embodiments, the pH of the formulation is 5.5 to 7.5. In embodiments, the pH is 5.5 to 6.5. In embodiments, the pH is 6 to 7.

In embodiments, an IL-1 inhibitor, e.g., anakinra, is formulated at an appropriate concentration (e.g., at a concentration of 5 mg/ml to 100, e.g., 5 to 50 mg/ml, e.g., 5 to 20 mg/ml) in 10 mM sodium citrate, pH 6.0 containing 5% w/v sorbitol and 0.1% w/v poloxamer, e.g., poloxamer 188. In embodiments, the amounts of the components of the formulation may vary around the values provided herein by up to 5%, 10%, 15%, 20%, 25%, 30%, 40%, or 50%. In embodiments, the pH is 5.5 to 7.5. In embodiments, the pH is 5.5 to 6.5. In embodiments, the pH is 6 to 7.

In embodiments, a formulation described herein further comprises a viscosity agent, e.g., sodium carboxymethyl cellulose (CMC). In embodiments, the formulation comprises CMC, e.g., CMC at a concentration of 0.1-1% w/v, 0.1-0.5% w/v, or 0.2-0.3 w/v %.

Also provided herein is a method for treating a subject having an IL-1-related disorder. The method includes administering to the subject a therapeutically effective amount of a composition comprising a formulation described herein. In embodiments, the method includes identifying a subject having an IL-1-related disorder such as, e.g., a dry eye disorder; and administering to the subject a therapeutically effective amount of a composition comprising a formulation as described herein.

Also described herein is a method of inhibiting IL-1 activity in a subject. The method includes administering to the subject a formulation as described herein. In embodiments, the subject has an IL-1-related disorder, e.g., a dry eye disorder.

In some embodiments, the invention relates to a drug delivery device comprising a formulation as described herein.

Also disclosed herein is the use of a composition as described herein in the manufacture of a medicament for treating or preventing an IL-1-related disorder in a subject, e.g., in the manufacture of a medicament for topical administration to a subject for treating or preventing an IL-1 related disorder in the subject. In embodiments, the medicament is for administration to the eye, e.g., for topical administration to the eye. In some embodiments, the medicament is a vehicle formulation, e.g., an aqueous formulation comprising or consisting of sorbitol, sodium citrate, and poloxamer 188 as described herein. In embodiments, the vehicle formulation is substantially free of (e.g., does not comprise) a therapeutic protein.

In general, the subject treated as described herein is a human or other mammal such as a dog or cat.

In some embodiments, the invention relates to a container or device comprising a formulation as described herein. In embodiments, the container is a blow fill seal container.

Applicants have also discovered a pharmaceutical formulation (e.g., a vehicle formulation) comprising a surfactant, a tonicity agent, and a buffering agent that can be useful for treating dry eye. In some embodiments, the formulation does not contain a protein or peptide, e.g., the formulation does not contain a therapeutic protein or peptide. In some embodiments, the surfactant is Pluronic F68 (poloxamer 188), the buffering agent is citrate, and the tonicity agent is sorbitol. In some embodiments, the formulation comprises a chimeric cytokine protein, e.g., a chimeric cytokine protein as described herein or in WO 2012/103240, e.g., P05. In some embodiments, the pharmaceutical formulation also includes a viscosity agent, e.g., CMC. In some embodiments, the pharmaceutical formulation is suitable for use in the eye (i.e., suitable for ocular delivery), e.g., for treating ocular disease such as signs and/or symptoms of dry eye.

Naturally occurring proteins referenced herein specifically include human forms of such proteins, and as well as forms from other mammalian species.

Embodiments described herein include the following:

EMBODIMENT 1

An aqueous formulation comprising sodium citrate or sodium phosphate at a concentration of 8 to 12 mM; sorbitol at 4% to 6% (w/v); poloxamer 188 at a concentration of 0.08% to 0.12% (w/v); and optionally sodium carboxymethyl cellulose, wherein the formulation has a pH of 5.5 to 7.5 and wherein the formulation is effective for treating an ocular disorder.

EMBODIMENT 2

The formulation of embodiment 1, wherein the formulation has a pH of 5.5 to 6.5.

EMBODIMENT 3

The formulation of embodiment 1 or embodiment 2, wherein the formulation is substantially free of a therapeutic protein.

EMBODIMENT 4

The formulation of any one of embodiments 1 to 3, wherein the formulation comprises sodium citrate at a concentration of 8 toll mM; sorbitol at 4.5 to 5.5% (w/v); and poloxamer 188 at a concentration of 0.09 to 0.11%.

EMBODIMENT 5

The formulation of embodiment 4, wherein the formulation consists of sodium citrate at a concentration of 9 toll mM; sorbitol at 4.5 to 5.5% (w/v); and poloxamer 188 at a concentration of 0.09 to 0.11%.

EMBODIMENT 6

The formulation of embodiment 5, wherein the formulation consists of sodium citrate at a concentration of 9 toll mM; sorbitol at 4.5 to 5.5% (w/v); and poloxamer 188 at a concentration of 0.09 to 0.11%.

EMBODIMENT 7

The formulation of any one of embodiments 1 to 6, comprising sodium carboxymethyl cellulose at a concentration of 0.1-1% (w/v).

EMBODIMENT 8

An aqueous formulation comprising sodium citrate at a concentration of 9-11 mM; sorbitol at 4.5-5.5% (w/v); and poloxamer 188 at a concentration of 0.09-0.11%, wherein the formulation has a pH of 5.7 to 6.3, wherein the formulation is substantially free of therapeutic protein, and wherein the formulation is effective for treating an ocular disorder (e.g., an ocular disorder described herein).

EMBODIMENT 9

The formulation any one of embodiments 1 to 8, wherein the ocular disorder is dry eye disease.

EMBODIMENT 10

The formulation of any one of embodiments 1 to 9, wherein the formulation is effective to reduce eye pain or soreness, OSDI score, and/or corneal fluorescein staining (CFS) score.

EMBODIMENT 11

The formulation of embodiment 10, wherein eye pain or soreness is assessed using a visual analog scale or a question from the OSDI.

EMBODIMENT 12

An aqueous formulation comprising 1-50 mg/ml of an IL-1β/IL-1Ra chimeric cytokine protein (e.g., P01, P02, P03, P04, P05, P06, or P07); a buffering agent selected from sodium citrate and sodium phosphate; sorbitol, e.g., at a concentration of 3.5-6.5% (w/v); poloxamer 188, e.g., at a concentration of 0.07-0.13% (w/v); and optionally sodium carboxymethyl cellulose (CMC), wherein the formulation has a pH of 5.5 to 7.5.

EMBODIMENT 13

The formulation of embodiment 12, wherein the chimeric cytokine protein is P05.

EMBODIMENT 14

The formulation of embodiment 13, wherein the formulation comprises 1-20 mg/ml P05.

EMBODIMENT 15

The formulation of embodiment 13, wherein the formulation comprises 3-7 mg/ml P05.

EMBODIMENT 16

The formulation of embodiment 13, wherein the formulation comprises 4-6 mg/ml P05.

EMBODIMENT 17

The formulation of embodiment 13, comprising sodium citrate and/or sodium phosphate at a total concentration of 5 mM to 15 mM.

EMBODIMENT 18

The formulation of any one of embodiments 12 to 17, wherein sodium citrate is present at a concentration of 5 mM to 15 mM.

EMBODIMENT 19

The formulation of embodiment 18, wherein the sodium citrate is present at a concentration of 8 mM to 12 mM.

EMBODIMENT 20

The formulation of embodiment 18, wherein the sodium citrate is present at a concentration of 9 mM to 11 mM.

EMBODIMENT 21

The formulation of any one of embodiments 12 to 20, wherein the poloxamer 188 is present at a concentration of 0.05% to 0.15% w/v.

EMBODIMENT 22

The formulation of embodiment 20, wherein the poloxamer 188 is present at a concentration of 0.08% to 0.12% w/v.

EMBODIMENT 23

The formulation of embodiment 20, wherein the poloxamer 188 is present at a concentration of 0.09% to 0.11% w/v.

EMBODIMENT 24

The formulation of any one of embodiments 12 to 23, wherein the sorbitol is present at a concentration of 2.5% to 7.5% w/v.

EMBODIMENT 25

The formulation of embodiment 24, wherein the sorbitol is present at a concentration of 4% to 6% w/v.

EMBODIMENT 26

The formulation of embodiment 24, wherein the sorbitol is present at a concentration of 4.5 to 5.5% w/v.

EMBODIMENT 27

An aqueous formulation comprising 1-25 mg/ml P05; sodium citrate or sodium phosphate at a concentration of 8 mM to 12 mM; sorbitol at 4% to 6% (w/v); poloxamer 188 at a concentration of 0.08% to 0.12% (w/v); and, optionally, sodium carboxymethyl cellulose, wherein the formulation has a pH of 5.5 to 7.5.

EMBODIMENT 28

An aqueous formulation comprising or consisting of 1 mg/ml to 25 mg/ml P05; sodium citrate at a concentration of 8-12 mM; sorbitol at 4% to 6% (w/v); and poloxamer 188 at a concentration of 0.08% to 0.12% (w/v), wherein the formulation has a pH of 5.5 to 7.5.

EMBODIMENT 29

An aqueous formulation comprising or consisting of 1 mg/ml to 25 mg/ml P05; sodium citrate at a concentration of 9 mM toll mM; sorbitol at 4.5% to 5.5% (w/v); and poloxamer 188 at a concentration of 0.09% to 0.11% (w/v); wherein the formulation has a pH of 5.7 to 6.3.

EMBODIMENT 30

An aqueous formulation comprising or consisting of 4-6 mg/ml P05; sodium citrate at a concentration of 9-11 mM; sorbitol at 4.5-5.5% (w/v); and poloxamer 188 at a concentration of 0.09-0.11% (w/v); wherein the formulation has a pH of 5.7-6.3.

EMBODIMENT 31

The formulation of any one of embodiments 12 to 30, wherein the formulation has an osmolality of 270-370 mOsm/kg.

EMBODIMENT 32

The formulation of any one of embodiments 1 to 31, wherein the formulation is suitable for administration to the eye.

EMBODIMENT 33

The formulation of embodiment 30, wherein the formulation is suitable for topical administration to the eye.

EMBODIMENT 34

The formulation of any one of embodiments 1 to 4 and 8 to 33, wherein the formulation does not comprise a viscosity agent, e.g., does not comprise CMC.

EMBODIMENT 35

The formulation of any one of embodiments 12 to 34, wherein the formulation further comprises an amino acid, e.g., arginine, glutamic acid, histidine, or methionine.

EMBODIMENT 36

The formulation of any one of embodiments 12 to 34, wherein the formulation further comprises methionine.

EMBODIMENT 37

The formulation of embodiment 36, wherein the methionine is present in the formulation at a concentration of 1 to 20 mM.

EMBODIMENT 38

The formulation of embodiment 36 or 37, wherein the formulation has reduced oxidation, compared to a corresponding formulation that does not comprise methionine, when the formulation is subjected to storage, e.g., for at least 4 weeks at 25° C.).

EMBODIMENT 39

The formulation of embodiment 38, wherein the formulation has reduced oxidation, compared to a corresponding formulation that does not comprise methionine, when the formulation is subjected to storage in a multidose container.

EMBODIMENT 40

The formulation of embodiment 38 or 39, wherein oxidation of the formulation is assessed using RP-HPLC.

EMBODIMENT 41

The formulation of any one of embodiments 12 to 40, wherein the formulation has less than or equal to 50 particles per ml for particles ≥10 μm and less than or equal to 5 particles per ml for particles ≥25 μm, as assessed using a light obscuration particle count test.

EMBODIMENT 42

The formulation of any one of embodiments 12 to 41, wherein the formulation is stable as indicated by the presence of >90% of the monomeric form of the protein relative to aggregated form after vortexing the protein solution for 4 hours at room temperature, e.g., at 25° C.

EMBODIMENT 43

The formulation of embodiment 42, wherein the percentage of the monomeric form of the protein relative to aggregated form is assessed using SEC-HPLC.

EMBODIMENT 44

The formulation of any one of embodiments 12 to 43, wherein the formulation is stable after storage for at least 5 months at 2-8° C. and 60% relative humidity.

EMBODIMENT 45

The formulation of any one of embodiments 12 to 44, wherein the formulation is stable after storage for at least 5 months under ambient conditions, e.g., at room temperature, e.g., at 25° C.

EMBODIMENT 46

The formulation of any one of embodiments 12 to 45, wherein the formulation is stable after storage for at least 4 months at 2-8° C. and 60% relative humidity.

EMBODIMENT 47

The formulation of any one of embodiments 12 to 46, wherein the formulation is stable after storage for at least 4 months under ambient conditions, e.g., at room temperature, e.g., at 25° C.

EMBODIMENT 48

The formulation of any one of embodiments 12 to 47, wherein the formulation is stable after storage for at least 3 months at 2° C. to 8° C. and 60% relative humidity.

EMBODIMENT 49

The formulation of any one of embodiments 12 to 48, wherein the formulation is stable after storage for at least 3 months under ambient conditions, e.g., at room temperature, e.g., at 25° C.

EMBODIMENT 50

The formulation of any one of embodiments 12 to 49, wherein the formulation is stable after storage for at least 2 months at 2-8° C. and 60% relative humidity.

EMBODIMENT 51

The formulation of any one of embodiments 12 to 50, wherein the formulation is stable after storage for at least 2 months under ambient conditions, e.g., at room temperature, e.g., at 25° C.

EMBODIMENT 52

The formulation of any one of embodiments 12 to 51, wherein the formulation is stable after storage for at least 1 month at 2-8° C. and 60% relative humidity.

EMBODIMENT 53

The formulation of any one of embodiments 12 to 52, wherein the formulation is stable after storage for at least 1 month under ambient conditions, e.g., at room temperature, e.g., at 25° C.

EMBODIMENT 54

The formulation of any one of embodiments 12 to 53, wherein the formulation is stable as indicated by the presence of less than or equal to 50 particles per ml for particles ≥10 μm, less than or equal to 5 particles per ml for particles ≥25 μm, and less than or equal to 2 particles per ml for particles ≥50 μm, e.g., as assessed using a microscopic particle count test.

EMBODIMENT 55

The formulation of any one of embodiments 12 to 54, wherein the formulation is stable as indicated by the presence of >90% of the monomeric form of the protein relative to aggregated form as assessed using SEC-HPLC.

EMBODIMENT 56

The formulation of any one of embodiments 12 to 55, wherein the formulation is stable as indicated by conformity of the main band to reference standard in a reduced SDS-PAGE.

EMBODIMENT 57

The formulation of any one of embodiments 12 to 56, wherein the formulation is stable as indicated by conformity of the main band to reference standard in a nonreduced SDS-PAGE.

EMBODIMENT 58

The formulation of any one of embodiments 12 to 57, wherein the formulation is stable as indicated by a main peak of greater than or equal to 85% when the formulation is assessed using weak cation exchange HPLC (WCEX-HPLC).

EMBODIMENT 59

The formulation of embodiment 58, wherein the formulation comprises P05 and is stable as indicated by the presence of less than 10% of the des-Ala form of P05 as assessed using WCEX-HPLC.

EMBODIMENT 60

The formulation of any one of embodiments 12 to 59, wherein the formulation is packaged in a blow fill seal container.

EMBODIMENT 61

The formulation of any one of embodiments 44 to 53, wherein said storage is storage in a blow fill seal container.

EMBODIMENT 62

A method of treatment, the method comprising administering to a subject having an IL-1-related disorder a formulation according to any one of embodiments 1 to 61, thereby treating the IL-1 related disorder.

EMBODIMENT 63

The method of embodiment 62, wherein the IL-1 related disorder is a dry eye disorder.

EMBODIMENT 64

A method of treating an ocular disorder, e.g., a dry eye disorder, the method comprising administering to a subject having the ocular disorder, e.g., the dry eye disorder, an aqueous formulation comprising sodium citrate or sodium phosphate at a concentration of 8 mM to 12 mM; sorbitol at 4% to 6% (w/v); poloxamer 188 at a concentration of 0.08% to 0.12% (w/v); and optionally sodium carboxymethyl cellulose; wherein the formulation has a pH of 5.5 to 7.5 and is substantially free of therapeutic protein, thereby treating the dry eye disorder.

EMBODIMENT 65

The method of embodiment 64, wherein the aqueous formulation comprises sodium citrate at a concentration of 8 mM to 11 mM, sorbitol at 4.5% to –5.5% (w/v) and poloxamer 188 at a concentration of 0.09% to 0.11%.

EMBODIMENT 66

The method of embodiment 64, wherein the aqueous formulation consists of sodium citrate at a concentration of 8-11 mM, sorbitol at 4.5-5.5% (w/v) and poloxamer 188 at a concentration of 0.09-0.11%.

EMBODIMENT 67

A method of treating a dry eye disorder, the method comprising administering to a subject having a dry eye disorder an aqueous formulation comprising 1 to 25 mg/ml P05; sodium citrate or sodium phosphate at a concentration of 8 mM to 12 mM; sorbitol at 4% to 6% (w/v); poloxamer 188 at a concentration of 0.08% to 0.12% (w/v); and optionally sodium carboxymethyl cellulose, wherein the formulation has a pH of 5.5 to 7.5, thereby treating the dry eye disorder.

EMBODIMENT 68

A method of treating a dry eye disorder, the method comprising administering to a subject having a dry eye disorder an aqueous formulation consisting of 1 mg/ml to 25 mg/ml P05; sodium citrate at a concentration of 8 mM to 12 mM; sorbitol at 4% to 6% (w/v); poloxamer 188 at a concentration of 0.08% to 0.12% (w/v), wherein the formulation has a pH of 5.5 to 7.5, thereby treating the dry eye disorder.

EMBODIMENT 69

A method of treating a dry eye disorder, the method comprising administering to a subject having a dry eye disorder an aqueous formulation comprising or consisting of 1 mg/ml to 25 mg/ml P05; sodium citrate at a concentration of 9 mM to 11 mM; sorbitol at 4.5% to 5.5% (w/v); and poloxamer 188 at a concentration of 0.09% to 0.11% (w/v), wherein the formulation has a pH of 5.7 to 6.3, thereby treating the dry eye disorder.

EMBODIMENT 70

The method of any one of embodiments 62 to 69, wherein the method is effective to reduce eye pain or soreness, OSDI score, and/or corneal fluorescein staining (CFS) score.

EMBODIMENT 71

The method of embodiment 70, wherein eye pain or soreness is assessed using a visual analog scale or a question from the OSDI.

EMBODIMENT 72

The method of any one of embodiments 62 to 70, wherein the formulation is administered one to five times per day.

EMBODIMENT 73

The method of any one of embodiments 62 to 72, wherein the formulation is administered topically.

EMBODIMENT 74

The method of embodiment 73, wherein the formulation is administered topically to the eye.

EMBODIMENT 75

The method of any one of embodiments 62 to 74, wherein the formulation is administered three times per day.

EMBODIMENT 76

The method of any one of embodiments 62 to 71 or 73 to 74, wherein the formulation is administered ad libitum.

EMBODIMENT 77

A container or device comprising the formulation of any one of embodiments 1 to 61.

EMBODIMENT 78

The container or device of embodiment 77, wherein the container or device has been stored at 25° C. for at least two weeks, e.g., for at least four weeks, and is substantially free of particulates.

EMBODIMENT 79

A blow fill seal container comprising the formulation of any one of embodiments 1 to 61.

EMBODIMENT 80

A multidose container comprising the formulation of any one of embodiments 1 to 61.

EMBODIMENT 81

A multidose container comprising the formulation of embodiments 35 to 40.

EMBODIMENT 82

A drug delivery device comprising a formulation of any one of embodiments 1 to 61.

EMBODIMENT 83

The drug delivery device of embodiment 82, wherein the drug delivery device is a blow fill seal container.

EMBODIMENT 84

The container or device of any one of embodiments 77 to 83, wherein the container or device is sealed in a pouch, optionally containing an inert gas, e.g., nitrogen or argon.

EMBODIMENT 85

The formulation of any one of embodiments 1 to 61, for use in treating an IL-1 related disorder, e.g., a dry eye disorder.

EMBODIMENT 86

Use of a formulation of any one of embodiments 1 to 61 in the manufacture of a medicament for treating an IL-1-related disorder in a subject.

EMBODIMENT 87

A kit comprising a container or device comprising the formulation of any one of embodiments 1 to 61, and optionally, instructions for use.

The foregoing embodiments are not necessarily separate embodiments. In some cases, they may be combined with each other and/or with other aspects and embodiments disclosed herein.

All patents, published patent applications, and published references cited herein are incorporated by reference for all purposes.

DETAILED DESCRIPTION

Figure 1:
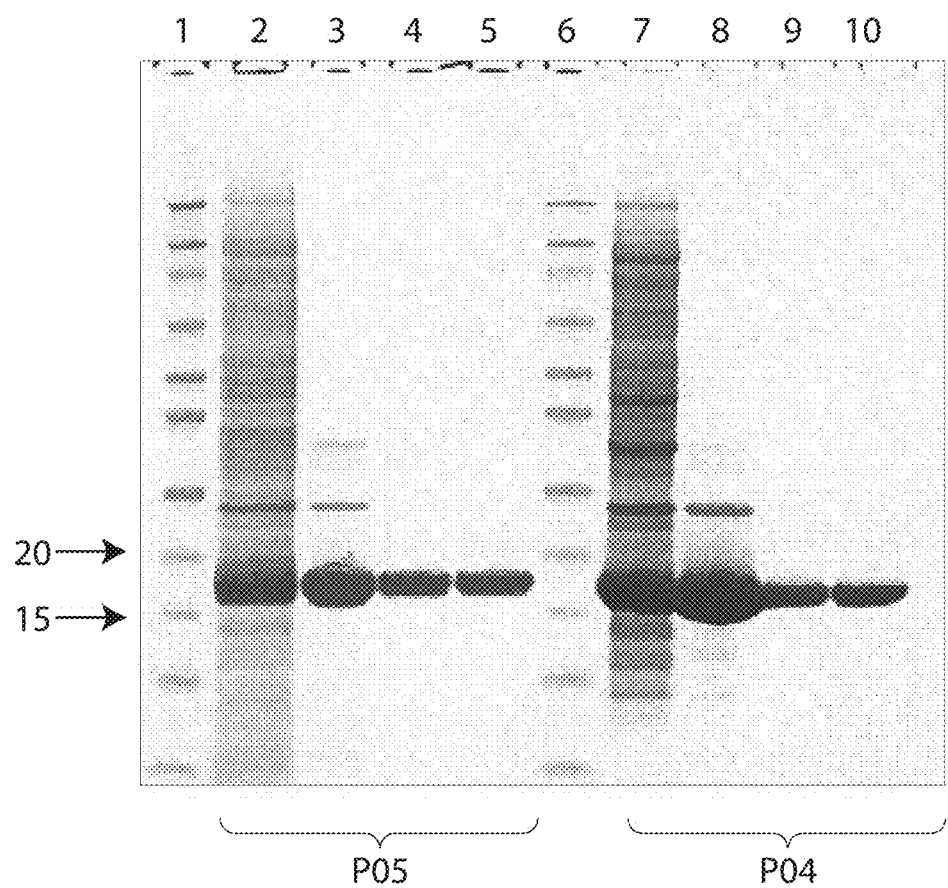
FIG. 1 is a reproduction of an SDS-PAGE gel showing exemplary samples of protein purified from E. coli expressing receptor binding agents. The 15 and 20 kDa molecular weight markers are indicated at left. Lanes are as follows: molecular weight marker (lanes 1 and 6), extract (lanes 2 and 7), material purified by cation exchange chromatography (lanes 3 and 8), material additionally purified by anion exchange chromatography (lanes 4 and 9), and reduced samples of such material (lanes 5 and 10). Lanes 2-5 are of P05 purification, and Lanes 6-10 are of P04 purification. See also Example 2.

Applicants have achieved formulations that are useful for providing a protein, e.g., a chimeric cytokine polypeptide such as an IL-1β/IL-1Ra chimera to a subject in need of treatment with such a formulation. The formulations are generally useful for formulation of protein compositions requiring stability, e.g., proteins that are susceptible to agitation, are susceptible to oxidation, e.g., due to methionine residues, or susceptible to deamindation, e.g., due to asparagine or arginine residues. Also disclosed herein are methods of preparing and administering such formulations.

In some embodiments, a formulation comprises a chimeric cytokine polypeptide, e.g., a chimeric polypeptide containing selected sequences derived from an IL-1β and an IL-1Ra sequence, that are suitable for pharmaceutical use, for example, for ophthalmic use, including effective topical treatment for an IL-1-related disorder. In general, formulations described herein are surprisingly stable, even at relatively high concentrations of the polypeptide, e.g., at concentrations suitable for storage of bulk drug substance as well as at concentrations suitable for for treating a subject. An advantage of this feature is that it is not necessary to remove undesirable agents from the bulk drug substance in order to formulate the drug for patient use.

Notably, Applicants have successfully achieved an effective aqueous formulation of chimeric cytokine polypeptides that is suitable for topical administration, e.g., in the eye, e.g., to the front or corneal surface of the eye. To the best of applicants' knowledge, as of this filing there are no approved biologic drugs (biologics) for topical ophthalmic administration approved by the FDA. Furthermore, applicants were able to formulate such a polypeptide at a pH that is compatible with administration to the eye (e.g., a pH of 4.5 to 7.0, 5.5 to 7.0, 5.5 to 6.5, or 6.0 to 7.0), and contains a components that render the formulation comfortable for subjects being treated with the polypeptide. Patients are more likely to be compliant with treatment if the formulation is comfortable, e.g., does not cause irritation. In embodiments, the formulation does not cause one or more symptoms of irritation such as, e.g., eye redness, tearing, mucous discharge, or subjective discomfort.

Stability

Topical ophthalmic drugs are generally self-administered by patients. Because the patient may be storing a drug for a relatively long period of time, the formulation may be subjected to higher temperatures and greater levels of agitation stress than a formulation that is typically stored only by a physician or pharmacist prior to administration. As is known in the art, proteins are more sensitive to agitation and temperature than small molecules. Agitation stress can lead to precipitation and heat stress can lead to precipitation and to chemical degradation. In addition, during loading of a compound into a delivery device, there can be exposure to heat stress. Applicants have achieved a formulation that successfully provides excellent stability when exposed to agitation stress and heat.

Some manufacturing processes require at least brief exposure of a formulation to relatively high temperature. For example, loading a formulation into a blow fill seal (BFS) container can result in exposure of the formulation to elevated temperatures, in addition to agitation associated with the filling process. Applicants have loaded a formulation into such a device (a BFS container) and demonstrated stability of the formulation immediately following loading and over an extended period of time. In some embodiments, a formulation as provided herein is suitable for use with BFS. In embodiments, a formulation that is suitable for use with BFS shows stability immediately following loading into a BFS container and/or after storage in a BFS container, e.g., after storage for periods of time and under conditions described herein.

In embodiments, a formulation described herein is stable. In embodiments, the formulation exhibits stability under conditions (e.g., storage at particular temperatures, or agitation stress) described herein. In embodiments, stability is assessed using one or more methods described herein (e.g., based on visual appearance, content by spectrophotometry (A280), SDS-PAGE non-reduced, SDS-PAGE reduced; size exclusion HPLC (SE HPLC); reverse phase HPLC (RP-HPLC); weak cation exchange HPLC (WCEX-HPLC); potency; a light obscuration particle count test (e.g., a light obscuration particle count test as described in USP <788>); or a microscopic particle count test (e.g., a microscopic particle count test as described in USP <788>)) and/or methods known in the art.

Stability can be assessed based on visual appearance. In embodiments, a formulation is stable if it is a clear to slightly opalescent colorless solution essentially free from visible particulates.

In embodiments, the formulation is stable at about 25° C. to about 40° C., for example, about 27° C., about 28° C., about 29° C., about 30° C., about 31° C., about 32° C., about 33° C., about 34° C., about 35° C., about 36° C., about 37° C., about 38° C., about 39° C., or about 40° C. for a period of at least two days; three days; five days; one week; ten days, two weeks, three weeks, four weeks, five weeks, six weeks, eight weeks, 16 weeks, 20 weeks, 25 weeks, 30 weeks, 35 weeks, 40 weeks, 45 weeks, one month, two months, three months, four months, five months, six months, seven months, eight months, or more.

In embodiments, the formulations are stable for long periods of time during storage at temperatures of from about 2° C. to about 8° C., such as at about 4° C., about 5° C., about 6° C., from 2° C. to 8° C., at 4° C., at 5° C., or at 6° C. For example, the formulations are stable at such storage temperatures for a period of at least two weeks; four weeks; six weeks; two months; three months; six months, one year, two years, three years, or four years.

Stability of a formulation can be assessed, e.g., after storage for at least 2, 4, 6, 8, 12, or 18 months, e.g., at 2-8° C., or after storage under ambient conditions, e.g., at room temperature (RT), e.g. at about 25° C. for, e.g., at least 2 weeks, 1 month, 2 months, 3 months 5 months, 6 months, 12 months, or 18 months. In embodiments, the formulation is stable after storage at 2-8° C. for at least 8 months. In embodiments, the formulation is stable after exposure to room temperature for at least 5 months. In some such embodiments, the formulation is stable after storage, e.g., for at least 5 months, in a BFS container.

Stability can be assessed, e.g., based on methods and criteria described herein or known in the art. For example, stability can be assessed based on physical purity (e.g., lack of aggregation, e.g., as assessed using size exclusion HPLC, also referred to herein as size exclusion, SE HPLC, or SEC HPLC), chemical purity (e.g., as assessed using weak cation exchange HPLC, reverse phase HPLC, and/or SDS PAGE (e.g., reduced or nonreduced SDS PAGE)), and/or the levels of particulates (e.g., as assessed visually or by particle count using an HIAC liquid particle counter (Beckman Coulter, Brea, Calif.)).

In embodiments, stability is demonstrated based on compliance with guidelines for particulate matter in opthalmic solutions, e.g., as set forth in USP <789> (U.S. Pharmacopeia, Particulate Matter in Opthalmic Solutions).

In embodiments, the formulation has less than or equal to 50 particles per ml for particles ≥10 μm and/or less than or equal to 5 particles per ml for particles ≥25 μm, e.g., as assessed using a light obscuration particle count test (e.g., a light obscuration particle count test as described in USP <788>).

In embodiments, the formulation has less than or equal to 50 particles per ml for particles ≥10 μm, less than or equal to 5 particles per ml for particles ≥25 μm, and/or less than or equal to 2 particles per ml for particles ≥50 μm, e.g., as assessed using a microscopic particle count test (e.g., a microscopic particle count test as described in USP <788>).

In embodiments, stability is demonstrated based on compliance with guidelines for particulate matter in injections, e.g., as set forth in USP <788> (U.S. Pharmacopeia, Particulate Matter in Injections).

In embodiments, the formulation has less than or equal to 6000 particles per container (for containers with a volume of 100 ml or less) for particles ≥10 m, and/or less than or equal to 600 particles per container (for containers with a volume of 100 ml or lower) for particles ≥25 um, e.g., as assessed using a light obscuration particle count test (e.g., a light obscuration particle count test as described in USP <788>).

In embodiments, the formulation has less than or equal to 3000 particles per 5 ml for particles ≥10 m and/or less than or equal to 300 particles per 5 ml for particles ≥25 um, e.g., as assessed using a microscopic particle count test (e.g., a microscopic particle count test as described in USP <788>).

In embodiments, the protein in a formulation is protected from agitation stress as demonstrated, e.g., by lack of aggregation (lack of aggregation may be demonstrated, e.g., if the formulation contains contains >90%, >91%, >92%, >93%, >94%, >95%, >96%, >97%, >98%, or >99% of the monomeric form of the protein relative to aggregated form) after vortexing the protein solution, e.g., for 1-8 hours at room temperature (RT), e.g., for 4 hours at RT. Aggregation can be assessed, e.g., using methods described herein or methods known in the art. For example, aggregation can be assessed using ultracentrifugation, size-exclusion chromatography, gel electrophoresis, dynamic light scattering, and/or turbidity measurements.

In some aspects, stability is assayed by physical or chemical methods known in the art. For example, physical purity or lack of aggregation can be determined using size exclusion HPLC or other methods that determine the relative amount of monomeric polypeptide in a formulation. Typically, a formulation with acceptable stability contains >90% of the monomeric form of therapeutic protein (e.g., the chimeric cytokine, e.g., P05) relative to aggregated forms of the protein. In embodiments, the formulation contains >90% (e.g., >91%, >92%, >93%, >94%, >95%, >96%, >97%, >98%, or >99%) of the monomeric form of the therapeutic protein (e.g., the chimeric cytokine, e.g., P05), relative to aggregated forms of the protein.

Chemical purity can be determined, for example, using weak cation exchange HPLC or reverse phase HPLC. Typically, a formulation with acceptable stability contains >80% of the native molecule, relative to chemically modified forms of the molecule, e.g., as assessed using weak cation exchange HPLC. In embodiments, the formulation contains >80% (e.g., >85%, >87%, >90%, or >95%) of the native molecule, relative to chemically modified forms of the molecule (e.g., oxidized or acetylated forms).

Particulates may be identified visually. In embodiments, the formulation is one that is essentially free of particulates that can be identified visually.

Applicants note that information on anakinra, an IL-1Ra, formulated for delivery by injection states that the product has a shelf life of three years, is to be stored at 3-8° C., and "For the purpose of ambulatory use, Kineret® may be removed from the refrigerator for 12 hours at temperature not above 25° C., without exceeding the expiry date. At the end of this period, the product must not be put back in the refrigerator and must be disposed of." (See: medicines.org.uk/EMC/medicine/23104/SPC/Kineret+100+mg+solution+for+injection+in+a+pre-filled+syringe#SHELF_LIFE). This provides a contrast to the surprising stability of, for example, the P05 formulation provided herein.

Biologic treatments can be problematic to administer because they can have a relatively short shelf life or require special storage conditions that can create obstacles for storage, transport, and patient use as well as assuring a sufficient supply of the biologic. An advantage of certain formulations provided herein is that the formulations are surprisingly stable not only under conditions of refrigeration, but also at temperatures that are in accord with room temperature (e.g., 25° C.) and above (e.g., 40° C.). Accordingly, the cytokine protein or polypeptide formulations (e.g. heterologous cytokine protein or polypeptide formulations), e.g., formulations described herein are, in some embodiments, provided in a liquid form that is stable at RT (e.g., at 25° C.) for a period of at least three days, five days, one week, ten days, two weeks, three weeks, six weeks, eight weeks, 16 weeks, 20 weeks, 25 weeks, 30 weeks, 35 weeks, 40 weeks, 45 weeks, one month, two months, three months, four months, five months, six months, seven months, eight months, twelve months, or more. In embodiments, a month is determined on date to date basis, e.g., from the first of the month to the first of the second month.

In other aspects the formulations are stable at about 25° C. to about 40° C., for example, about 27° C., about 28° C., about 29° C., about 30° C., about 31° C., about 32° C., about 33° C., about 34° C., about 35° C., about 36° C., about 37° C., about 38° C., about 39° C., or about 40° C. for a period of at least two days; three days; five days; one week; ten days, two weeks, three weeks, four weeks, five weeks, six weeks, eight weeks, 16 weeks, 20 weeks, 25 weeks, 30 weeks, 35 weeks, 40 weeks, 45 weeks, one month, two months, three months, four months, five months, six months, seven months, eight months, or more.

In one example, a formulation is stable for one month at 25° C. and 1 week at 40° C. when the protein component of the formulation, e.g., P05, is at a concentration of 20 mg/ml. In another specific embodiment, the formulation, loaded into a blow fill seal vial or blow fill delivery device, is stable at 25° C. for at least three months for a formulation comprising protein, e.g., P05, at a concentration of 1 mg/ml, 5 mg/ml, or 10 mg/ml. In some embodiments, this formulation is stable for at least eight months.

In embodiments, a formulation comprising 4.5-5.5 mg/ml P05, 9-11 mM sodium citrate; 4.5-5.5% w/v sorbitol, and 0.09-0.11% w/v poloxamer 188 is stable for at least five months at 2° C. to 8° C. and/or at room temperature, e.g., at 25° C. In some embodiments, a formulation consisting of 10 mM Na citrate, pH 6.0, 5% sorbitol, 0.1% poloxamer, and 5 mg/ml or 20 mg/ml P05 is stable for at least five months at 2° C. to 8° C. and/or at room temperature, e.g., at 25° C. for at least 5 months.

Concentration

A further problem in administering biologics, is providing a sufficient concentration of the biologic. This is a particular problem in ophthalmic applications in which it is desirable to provide a relatively high concentration of the biologic so as to achieve a therapeutic effect with a minimum number of doses. Applicants have been able to achieve a formulation that can deliver an effective dose of a chimeric cytokine formulation containing a high concentration, or a therapeutically effective concentration, of the polypeptide that does not appreciably aggregate, precipitate, or lose chemical purity when stored under conditions such as those described supra and elsewhere within this specification. Furthermore, applicants have demonstrated stability of a cytokine formulation at protein concentrations of up to 80 mg/ml, e.g., 50 mg/ml in a formulation comprising a tonicity agent, a surfactant, and a buffering agent. Therefore, in one aspect, a formulation featured in the invention contains a chimeric cytokine polypeptide stably present in the formulation in a concentration of from 0.1 mg/ml to 100 mg/ml, 0.1-80 mg/ml, 0.1 to 50 mg/ml, 0.1 mg/ml to 20 mg/ml, 0.1 mg/ml to 5 mg/ml, 0.1 mg/ml to 1 mg/ml, 1 mg/ml to 100 mg/ml; 5 mg/ml to 100 mg/ml; 5 mg/ml to 30 mg/ml; 10 mg/ml to 100 mg/ml; 10 mg/ml to 30 mg/ml; 20 mg/ml to 100 mg/ml; 30 mg/ml to 100 mg/ml; 40 mg/ml to 100 mg/ml; 50 mg/ml to 100 mg/ml; 60 mg/ml to 100 mg/ml; 1 mg/ml to 80 mg/ml; 5 mg/ml to 80 mg/ml; 10 mg/ml to 80 mg/ml; 20 mg/ml to 80 mg/ml; 40 mg/ml to 80 mg/ml; 50 mg/ml to 80 mg/ml; 60 mg/ml to 80 mg/ml; 1 mg/ml to 60 mg/ml; 5 mg/ml to 60 mg/ml; 10 mg/ml to 60 mg/ml; 20 mg/ml to 60 mg/ml; 30 mg/ml to 60 mg/ml; 40 mg/ml to 60 mg/ml; or 50 mg/l to 60 mg/ml. For example, the formulation contains 0.1 mg/ml, 1 mg/ml, 2 mg/ml, 5 mg/ml to 20 mg/ml, e.g., 5 mg/ml or 20 mg/ml.

Viscosity agents are frequently used in formulations, e.g., for ophthalmic use. Such agents are generally included to increase the residence time of an ophthalmic treatment that would otherwise be rapidly cleared by blinking and drainage through the conjunctival sac. However, such agents can have deleterious effects, e.g., allergic symptoms, damage protein components of a formulation, or cause blurry vision. While such agents can be used in certain formulations described herein, in some embodiments Applicants have achieved formulations that do not require a viscosity agent for the active component, i.e., a chimeric cytokine, to be used as an effective therapeutic.

In another aspect the formulations featured in the invention contain one or more surfactants. Although the use of a surfactant can be useful, e.g., for reducing adhesion of a molecule to a container, reducing aggregation of a protein particularly under conditions of agitation, addition of a surfactant can also render a therapeutic agent unusable because of foaming, disruption of natural membranes and other barriers, and unacceptable discomfort caused by treatment. Applicants have succeeded in providing a formulation that includes a surfactant, but does not incur such disadvantages. Typically, the surfactant is a non-ionic surfactant. Surfactants suitable for use in the disclosed formulations can include, but are not limited to: poloxamers, such as poloxamer 188. In some embodiments, a surfactant is a polysorbate, such as polysorbate-20 and polysorbate-80. Other surfactants that can be useful include Cremophor® EL, tyloxapol, octoxynol 40 (Triton® X405, and polyoxyl 40 stearate. In certain embodiments, a formulation contains a surfactant (e.g., poloxamer 188) in a concentration of about 0.05%, 0.06%, 0.1% to 1.0%, 0.1% to 0.5%, 0.2% to 0.5%, or 0.1% to 0.2% w/v, for example, 0.1% w/v poloxamer 188. Suitable surfactants and concentrations of such surfactants can be determined by testing whether the surfactant prevents aggregation in agitation studies. Methods of conducting such studies are known in the art. For example, it can be determined whether surfactant is needed to prevent precipitation from agitation stress. In such experiments, typically, a screen is performed using agitation and analysis. Examples of concentrations used for such studies are 0.01%, 0.02%, 0.06%, and 0.1% w/v surfactant, e.g., poloxamer 188. In embodiments, aggregation and/or precipitation are assessed using analysis by spectrophotometry ($A_{280}$), visual inspection, size exclusion chromatography (SEC), light obscuration (e.g., using a HIAC device), or Micro-Flow Imaging™ (MFI, ProteinSimple, Santa Clara, Calif.). A surfactant is generally selected for use in a formulation that is associated with the least amount of precipitation, e.g., no visible precipitation, or particle count that meets guidelines for particulate matter in injections (see, e.g., USP <788>) or guidelines for particulate matter in ophthalmic solutions (see, e.g., USP<789>).

In another aspect, the formulations featured in the invention contain one or more tonicity agents. Suitable tonicity agents include, but are not limited to: sodium chloride, sorbitol; mannitol, sucrose, trehalose, or other sugars. Without committing to any theory, such agents may contribute to the surprising stability of a chimeric cytokine polypeptide. In embodiments, a tonicity agent, e.g., a sugar such as, e.g., sorbitol, provides or contributes to thermal stability. In certain embodiments, the formulations featured in the invention are isotonic for the eye (e.g., having an osmolality of about 270-330 mOsm per kg). In some embodiments, the formulation has an osmolality of from about 250 to about 450 mOsm per kg, 300 to 400 mOsm per kg, 350 to 400 mOsm per kg, 200 to 375 mOsm per kg, or 350 to 375 mOsm per kg. In embodiments, the formulation has an osmolality of 270-330 mOsm per kg, e.g., about 320 mOsm per kg. Depending upon the tonicity agent, certain embodiments featured in the invention contain from about 1% to about 15% w/v; 2% to 12% w/v; 5% to 12% w/v; or 5% to 10% w/v. For sorbitol or mannitol, an example of a concentration is about 5% w/v, e.g., the concentration is 5% w/v. For sucrose or trehalose, an example of a concentration is about 9% w/v.

Buffering Agents

In another aspect, a formulation featured herein contains one or more buffering agents. Suitable buffering agents include, but are not limited to, phosphates; citrates; acetates; borates; succinates; and TRIS. In some cases a salt of the buffering agents is a sodium salt or a potassium salt. In certain embodiments featured in the invention, the buffering agent is present in an amount of from about 10 mM to about 50 mM, for example from about 20 mM to about 40 mM, to provide a weak buffering effect. This allows the formulation to be quickly neutralized at the administration site, e.g., on the surface of the eye, in the event of stinging or discomfort. In some embodiments, the buffering agent is present in an amount of about 10 mM, about 15 mM, about 20 mM, about 25 mM, about 30 mM, about 35 mM, about 40 mM, about 45 mM or about 50 mM. In some formulations, the buffering agent is a citrate, e.g., sodium citrate. In other formulations, the buffering agent is citrate present at 10 mM. In general, the buffering agent is a weak buffering agent.

In general, a suitable buffer is selected by conducting a stability study in which the polypeptide of interest is exposed to various buffers at various pH's, concentrations, temperatures, and for various times. Buffers can be selected, for example by placing the polypeptide of interest in the buffer and subjecting the samples to elevated temperatures (accelerated stability testing) then test for physical stability (precipitation by visual inspection) or chemical stability, for example, by monitoring deamidation by weak cation exchange chromatography or oxidation by reversed phase chromatography. Additional assays can include monitoring of $A_{280}$, SDS-PAGE, pH, and osmolality. A buffer that provides the best physical and chemical stability is selected.

Amino Acids

In another aspect, a formulation featured in the invention contains one or more amino acids. Suitable amino acids include, but are not limited to: arginine, glutamic acid, histidine, or methionine. The amino acid is typically selected to enhance the stability and/or the solubility of the protein. Methods of identifying such amino acids are known in the art. In some embodiments, a formulation such as a P05 formulation contains histidine or methionine.

In some embodiments a formulation contains an oxygen scavenger, e.g. methionine. In some embodiments, the formulation is in a plastic container. In embodiments, the plastic container is sterilized using a method that generates free radicals, e.g., the container is sterilized using gamma radiation or ethylene oxide. In some such embodiments, the formulation includes methionine, e.g., methionine at a concentration of 1-20 mM. In embodiments, methionine is present at a concentration of 1-5 mM, 5-10 mM, 10-15 mM, 15-20 mM, or 5-15 mM. In embodiments, methionine is present at about 1 mM, 5 mM, 10 mM, 15, mM, or 20 mM. In embodiments, the formulation comprises methionine at a concentration of about 5 mM, e.g., at a concentration of 2.5-7.5 mM, 3-7 mM, or 4-6 mM. In some embodiments a formulation comprising methionine in a sterilized plastic container and the amount of oxidation is less than that of a corresponding formulation that does not contain methionine.

Viscosity Agents

In another aspect, formulations featured in the invention may contain one or more viscosity agents. Suitable viscosity agents include, but are not limited to, methylcelluloses, including sodium carboxymethyl cellulose (also referred to herein as carboxymethyl cellulose or CMC); hydroxy celluloses, including ethyl cellulose; hydroxypropyl methylcellulose (hypromellose); carbomers, such as 934P, 971P and 974P; polyvinyl alcohol; xanthan gum; guar gum; gellan gum; and glycerin.

The formulations featured in the invention may also contain other pharmaceutically acceptable excipients. See e.g., Gennaro (ed.), *Remington: The Science and Practice of Pharmacy*, 20th ed., Lippincott, Williams & Wilkins (2000) (ISBN: 0683306472); Ansel et al., *Pharmaceutical Dosage Forms and Drug Delivery Systems*, 7th Ed., Lippincott Williams & Wilkins Publishers (1999) (ISBN: 0683305727); Kibbe (ed.), *Handbook of Pharmaceutical Excipients*, 3rd ed. (2000) (ISBN: 091733096X); *Protein Formulation and Delivery*, McNally and Hastedt (eds.), Informa Health Care (ISBN: 0849379490) (2007). Among the excipients that can be added are preservatives, penetration enhancers and bioadhesives. Penetration enhancers and bioadhesives may include, for example, chitosan, cytochalasin B, aminated gelatin, poly-ε-caprolectone (carbopol 941P); poly(butylcyanoacrylate); poly-L-arginine; cyclodextrins; gellan; poly(acrylic acid); hyaluronic acid; mucin; alginate; a carbophil, and poloxamers (e.g., see Nagarwal et al., J Controlled Release, 136:2-13 (2009); Ding, PSTT 1:328-35 (1998); and Sahoo et al., Drug Discovery Today, 13:144-51(2008). Other excipients may be useful as stabilizers, and can include, for example, glycerin, potassium chloride, potassium phosphate, propylene glycol, sodium acetate, sodium bisulfite, sodium borate, sodium borate decahydrate, sodium chloride, sodium citrate, sodium phosphate, sodium phosphate (including sodium phosphate monobasic and dibasic); zinc chloride, phenol, benzoate, derivatives of castor oil and ethylene oxides, and Cremophor® (BASF Corp., Germany).

Pharmaceutical compositions featured in the invention can be formulated in a variety of forms. These include, for example, liquid, semi-solid, and solid dosage forms, such as liquid solutions (e.g., injectable and infusible solutions), dispersions or suspensions, including nanoparticles and liposomes. The form will generally depend on the intended mode of administration and therapeutic application. Compositions for the agents described herein are typically in the form of injectable or infusible solutions, or are formulated for topical delivery, e.g., topical ocular delivery.

In some embodiments, a pharmaceutical composition described herein is sterile and stable under the conditions of manufacture and storage. A pharmaceutical composition can also be tested to ensure it meets regulatory and industry standards for administration. The composition can be formulated as a solution, microemulsion, dispersion, liposome, or other ordered structure suitable to high drug (e.g., a biologic) concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, exemplary methods of preparation include vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be engineered by inclusion of an agent that delays absorption, for example, monostearate salts and gelatin. Such an agent may be particularly useful in a low-dose formulation. In embodiment, the formulation comprises ≤1 mg/ml of a therapeutic protein (e.g., a chimeric cytokine, e.g., P05) and gelatin is included in the formulation.

In certain embodiments, a formulation is prepared with a carrier, e.g., to extend the pharmacokinetics (PK) of a chimeric cytokine polypeptide (e.g., as assessed based on its half-life in the body, e.g., in the eye, e.g., on the cornea). In such embodiments, the chimeric cytokine polypeptide can be delivered, for example, as a controlled release formulation, delivered by an implant or a microencapsulated delivery system. Biodegradable, biocompatible polymers can be used, such as ethylene vinyl acetate, polyanhydrides, polyglycolic acid, collagen, polyorthoesters, and polylactic acid. See e.g., *Sustained and Controlled Release Drug Delivery Systems*, J. R. Robinson, ed., Marcel Dekker, Inc., New York, 1978.

A feature of formulations described herein is that they do not contain a preservative. In general, preservatives can affect the chimeric cytokine polypeptide, e.g., causing changes to the structure of the polypeptide. In addition, preservatives can cause in a subject, for example, an inflammatory response, which is antithetical to the desired treatment effect. Formulations are sterile, stored, and filled into their final containers under sterile conditions.

Vehicle Formulations

Applicants have also unexpectedly discovered that a formulation as described herein that does not contain a therapeutic protein (e.g., a vehicle only formulation) is useful for treating one or more signs or symptoms of ocular disease, e.g., dry eye disease, e.g., signs or symptoms of dry eye disease described herein. In some embodiments, a vehicle formulation comprises a surfactant, a tonicity agent, and a buffering agent. In some such embodiments, the formulation is effective to decrease pain (e.g., pain as assessed using the pain question score or a visual analog scale), the OSDI, or a subscale of the OSDI. In some such embodiments, the formulation decreases corneal fluorescein staining (CFS). As used herein, the term "vehicle only formulation" specifically refers to a formulation described herein that is substantially free of protein or peptide components, e.g., does not contain a therapeutic protein. It is to be understood that a vehicle formulation described herein can contain any therapeutic protein, e.g., a therapeutic polypeptide.

In some embodiments, the vehicle formulation, e.g., the vehicle only formulation, substantially comprises a surfactant (e.g., poloxamer 188), a tonicity agent (e.g., sorbitol), and a buffering agent (e.g., sodium citrate). In embodiments, the vehicle formulation is substantially free of protein. In embodiments, the vehicle formulation is substantially free of a therapeutic protein or peptide. In embodiments, the vehicle formulation does not contain a viscosity agent.

Useful surfactants, tonicity agents, and buffering agents include those disclosed herein. In some embodiments, the surfactant is poloxamer 188, the tonicity agent is sorbitol, and the buffering agent is sodium citrate and/or sodium phosphate.

In embodiments, the buffering agent is present at a concentration of 20 mM or less.

In some embodiments, the vehicle formulation comprises about 0.1% w/v poloxamer 188, about 5% w/v sorbitol, and about 10 mM w/v sodium citrate. In embodiments, the components of a vehicle formulation described herein are present in amounts that may vary around the values provided herein by up to 5%, 10%, 15%, 20%, 25%, 30%, 40%, or 50%. In embodiments, the components of a vehicle formulation are present in amounts that vary around the values provided herein by 10%. In some embodiments, the vehicle formulation is an aqueous formulation consisting of 10 mM sodium citrate, pH 6.0, 5% sorbitol (w/v), and 0.1% poloxamer 188.

In embodiments, the vehicle formulation comprises 9.5-10.5 mM, 9-11 mM, 8.5-11.5 mM, 8-12 mM, 7.5-12.5 mM, 7-13 mM, 6-14 mM, or 5-15 mM sodium phosphate or sodium citrate. In embodiments, the vehicle formulation comprises 9.5-10.5 mM, 9-11 mM, 8.5-11.5 mM, 8-12 mM, 7.5-12.5 mM, 7-13 mM, 6-14 mM, or 5-15 mM sodium citrate. In embodiments, the vehicle formulation comprises 4.75-5.25%, 4.5-5.5%, 4.25-5.75%, 4-6%, 3.75-6.25%, 3.5-6.5%, 3-7%, or 2.5-7.5% w/v sorbitol. In embodiments, the vehicle formulation comprises 0.095-0.105%, 0.09-0.11%, 0.085-0.115%, 0.08-0.12%, 0.075-0.125%, 0.07-0.13%, 0.06-0.14%, or 0.05-0.15% w/v poloxamer 188.

In embodiments, the pH of the vehicle formulation is 5.5 to 7.5. In embodiments, the pH is 5.5 to 6.5. In embodiments, the pH is 6 to 7. In embodiments, the formulation comprises 8-12 mM sodium citrate, 4-6% w/v sorbitol, 0.08-0.12% w/v poloxamer 188, and has a pH of 5.5. to 7.5, e.g., a pH of 5.5 to 6.5.

In embodiments, the vehicle formulation comprises 9-11 mM sodium citrate, 4.5-5.5% w/v sorbitol, 0.09-0.11% w/v poloxamer 188, and has a pH of 5.5. to 7.5, e.g., a pH of 5.5 to 6.5. In embodiments, the vehicle formulation comprises 7-13 mM sodium citrate, 3.5-5.5 w/v % sorbitol, 0.07-0.13% w/v poloxamer 188, and has a pH of 5.5. to 7.5, e.g., a pH of 5.5 to 6.5.

In embodiments, the vehicle formulation does not contain a viscosity agent.

In embodiments, the vehicle formulation comprises a viscosity agent, e.g., sodium carboxymethyl cellulose (CMC). In embodiments, the vehicle formulation comprises CMC, e.g., CMC at a concentration of 0.1-1% w/v, 0.1-0.5% w/v, or 0.2-0.3 w/v %.

In some embodiments, the vehicle formulation comprises 0.1% w/v poloxamer 188, 5% w/v sorbitol, 0.25% w/v sodium carboxymethyl cellulose and 10 mM sodium phosphate. In embodiments, the vehicle formulation has a pH of about 6.5. In embodiments, the components of the formulation are present in amounts that may vary around the values provided by up to 5%, 10%, 15%, 20%, 25%, or 30%. In some embodiments, the vehicle formulation consists of 0.1% w/v poloxamer 188, 5% w/v sorbitol, 0.25% w/v sodium carboxymethyl cellulose and 10 mM sodium phosphate.

In embodiments, the formulation comprises 0.08-0.12% w/v poloxamer 188, 4-6% w/v sorbitol, 0.2-0.3% w/v sodium carboxymethyl cellulose and 8-10 mM sodium phosphate. In embodiments, the formulation has a pH of 5.5-7.5, e.g., a pH of 5.5-6.5.

Administration

In some embodiments, a formulation featured herein, e.g., a formulation containing a therapeutic protein such as a chimeric IL-1 inhibitor or a vehicle formulation, is administered topically to a subject, e.g., a human or other mammal such as a dog, cat, or horse, and, for example administered to the eye. In general, a formulation described herein can be administered to a subject, by any suitable method, such as intravenous administration as a bolus or by continuous infusion over a period of time, by intramuscular, intramuscular, intraarterial, intrathecal, intracapsular, intraorbital, intracardiac, intradermal, intraperitoneal, intrasynovial, transtracheal, subcutaneous, subcuticular, intraarticular, subcapsular, subarachnoid, intraspinal, epidural injection, intrasternal injection and infusion. Other suitable modes of administration include topical (e.g., dermal or mucosal) or inhalation (e.g., intranasal or intrapulmonary) routes. For certain applications, the route of administration is one of: intravenous injection or infusion, subcutaneous injection, or intramuscular injection. For administration to the eye, in some embodiments, the mode of administration for a formulation featured herein (e.g., a chimeric cytokine formulation described herein) is topical administration to the eye, e.g., in the form of drops. Examples of devices that may contain the formulation and/or be used for administration of the formulation include simple eye droppers, squeeze bottles with or without metering function, and blow/fill/seal (BFS) devices such as those manufactured by Catalent (Somerset, N.J.), multi-use devices using, for example tip-seal technology, silver/oligodynamic technology, sterile filters, collapsing primary containers, and the like.

Another consideration for a formulation is minimizing sticking to the delivery device or container. For example, the addition of surfactant, e.g., poloxamer 188 can minimize sticking of P05 to a container.

An additional consideration for a container is that it provide an acceptable shelf-life once it is filled, e.g., there is an acceptably low level of evaporation and/or the formulation meets release assay specifications, e.g., specifications as described herein. In embodiments, the container is suitable to provide a shelf-life of at least two years, e.g., at least 3 years, at least 4 years, or at least 5 years, e.g., at 5° C. In embodiments, the container is suitable to provide a shelf-life of at least 3 years at 5° C. In embodiments, the container is suitable to provide a shelf-life of at least 2 months, 3 months, 4 months, 5 months, 6 months, 8 months, 10 months, or 12 months at RT. In embodiments, the the container is suitable to provide a shelf-life of at least 5 months at RT. Various suitable container materials are known in the art, for example certain plastics, for example, low density polyethylene (LDPE), high densidy polyethylene (HDPE), or polypropylene.

The formulation can be prepared for single use application in a container or can be prepared for use in a multiuse container.

A formulation featured herein can be delivered intravitreally, e.g., to treat disorders that are associated with, for example, the posterior segment of the eye. Methods of intravitreal administration are known in the art and include, for example, intraocular injection, implantable devices.

In embodiments, the formulation is administered intravitreally using an implantable device. In embodiments, the formulation comprises a thermal stabilizer, e.g., sorbitol. In embodiments, the sorbitol is present at a concentration of ≥5% w/v.

Implantable devices can be, for example, nonbiodegradable devices such as polyvinyl alcohol-ethylene vinyl acetate polymers and polysulfone capillary fibers, biodegradable devices such as polylactic acid, polyglycolic acid, and polylactic-co-glycolic acid, polycaprolactones, and polyanhydrides. Devices can be delivered in forms such as nanoparticles, liposomes, or microspheres.

A formulation featured in the invention can be administered as a fixed dose, as weight determined dose (e.g., mg/kg), or as an age determined dose. The formulations, e.g., a vehicle formulation or a therapeutic formulation (a formulation that includes a therapeutic such as a therapeutic protein) can be administered, for example, four times a day; three times a day; twice a day; once every day; every other day; every third, fourth or fifth day; every week; every two weeks; every three weeks; every four weeks; every five weeks; monthly; every two months; every three months; every four months; every six months; or as needed (ad libitum).

In embodiments, the formulation is administered once, twice, or three times a day. In some such embodiments, the formulation is administered topically, e.g., to the surface of the eye.

A pharmaceutical composition can include a "therapeutically effective amount" of an agent described herein. A therapeutically effective amount of an agent can vary according to factors such as the disease state, age, sex, and weight of the individual, and the ability of the compound to elicit a desired response in the individual, e.g., amelioration of at least one disorder parameter (e.g., sign), or amelioration of at least one symptom of the disorder (and optionally the effect of any additional agents being administered). A therapeutically effective amount is also one in which any toxic or detrimental effects of the composition are outweighed by the therapeutically beneficial effects. In some embodiments, a "therapeutically effective amount" is determined in a population of individuals and the amount is effective in ameliorating at least one symptom or indication of a cytokine-related disorder, e.g., an IL-1-related disorder in at least 5%, 10%, 25%, 50%, 70%, 75%, 80%, 85%, 90%, 95%, or 100% of an affected population. A formulation is typically administered in a therapeutically effective amount. In some cases, a therapeutically effective formulation is a vehicle formulation. In some cases, a therapeutically effective formulation comprises a therapeutic protein.

In some embodiments, the formulation is administered to a subject having an IL-1-related disorder and the chimeric cytokine polypeptide comprises fragments of IL-1β and Il-1Ra sequences. Such a formulation contains, for example, 5 mg/ml to 20 mg/ml, 5 mg/ml or 20 mg/ml of the polypeptide. In embodiments, the formulation is administered topically to the eye once, twice, three, four, five, or six times per day. Pharmaceutical compositions can be administered using medical devices as described herein and as known in the art, e.g., implants, infusion pumps, hypodermic needles, and needleless hypodermic injection devices. A device can include, e.g., one or more housings for storing pharmaceutical compositions, and can be configured to deliver unit doses of the chimeric cytokine polypeptide, and optionally a second agent. The doses can be fixed doses, i.e., physically discrete units suited as unitary dosages for the subjects to be treated; each unit can contain a predetermined quantity of chimeric cytokine polypeptide calculated to produce the desired therapeutic effect in association with a pharmaceutical carrier and optionally in association with another agent, e.g., Restasis® or artificial tears such as those available as over the counter or prescribed products.

In some embodiments, to treat a disorder described herein such as an Il-1-related disorder, the formulation is administered to a subject having the disorder in an amount and for a time sufficient to induce a sustained improvement in at least one sign or symptom of the disorder. An improvement is considered "sustained" if the subject exhibits the improvement over a prolonged period, e.g., on at least two occasions separated by one to four weeks. The degree of improvement can be determined based on signs or symptoms, and can also employ questionnaires that are administered to the subject, such as quality-of-life questionnaires. In one non-limiting example, the chimeric cytokine polypeptide comprises fragments of an IL-1β and an IL-1Ra and is topically administered at least once per week, e.g., at least once per day, at least twice per day, or at least three times per day.

Improvement can be induced by repeatedly administering a dose of the formulation until the subject manifests an improvement over baseline for selected signs and/or symptoms. In treating chronic conditions, the amount of improvement can be evaluated by repeated administration over a period of at least a month or more, e.g., for one, two, or three months or longer, or indefinitely. In treating an acute condition, the agent can be administered for a period of one to six weeks or even as a single dose.

Although the extent of the disorder after an initial or intermittent treatment can appear improved according to one or more signs or symptoms, treatment can be continued indefinitely at the same level or at a reduced dose or frequency. Treatment can also be discontinued, e.g., upon improvement or disappearance of signs or symptoms. Once treatment has been reduced or discontinued, it may be resumed if symptoms should reappear.

Treatments

Some formulations featured herein comprise a therapeutic protein. In embodiments, the formulations comprise a chimeric receptor binding agent (e.g., a chimeric cytokine) such as one that can bind to an IL-1R and that can antagonize IL-1 signaling, and therefore can be used to treat an "IL-1 related disorder," which includes any disease or medical condition that is (i) caused at least in part by IL-1 agonism, (ii) is associated with elevated levels or activity of an IL-1 signaling component (such as IL-1α, IL-1β, or IL-1RI) or elevated IL-1 signaling, and/or (iii) is ameliorated by decreasing IL-1 activity. IL-1 related disorders include acute and chronic disorders, including autoimmune disorders and inflammatory disorders. IL-1 related disorders include systemic and non-systemic disorders. It is well established that IL-1α and IL-1β are potent pro-inflammatory cytokines implicated in infectious responses as well as in inflammatory disease, including, e.g., rheumatoid arthritis. Increased IL-1 production has been observed in patients with certain autoimmune disorders, ischemia, and various cancers, therefore implicating IL-1 in these and related diseases (for example, see Sims and Smith, Nature Rev Immunol, 10:89-102 (2010)).

As used herein, the term "treat" refers to the administration of an agent described herein to a subject, e.g., a patient, in an amount, manner, and/or mode effective to improve a condition, symptom, or parameter associated with a disorder, e.g., a disorder described herein, or to prevent the onset or progression of a disorder, to either a statistically significant degree or to a degree detectable to one skilled in the art. The treatment can be to cure, heal, alleviate, relieve, alter, remedy, ameliorate, palliate, improve or affect the disorder, the symptoms of the disorder or the predisposition toward the disorder. An effective amount, manner, or mode can vary depending on the subject and may be tailored to the subject. Exemplary subjects include humans, primates, and other non-human mammals. A formulation featured in the invention can also be given prophylactically to reduce the risk of the occurrence of a disorder or symptom or sign thereof.

The IL-1-related disorder can be an autoimmune disorder. Examples of IL-1-related autoimmune disorders include rheumatoid arthritis, ankylosing spondylitis, Behçet's syndrome, inflammatory bowel diseases (including Crohn's disease and ulcerative colitis), asthma, psoriasis, type I diabetes, some forms of acne, and other disorders identified herein. The formulations described herein can be administered to a subject having or at risk for such IL-1 mediated autoimmune disorders. The IL-1 mediated disorder can be an inflammatory disorder such as described below. The formulations described herein can be administered to a subject having or at risk for such IL-1 mediated inflammatory disorders.

The formulations featured in the invention are particularly suited for use in ocular disorders, e.g. ocular disorders in which it is desired to administer the chimeric cytokine receptor directly to the eye, or locally to the area of the eye. Exemplary IL-1-related ocular disorders include Sjögren's syndrome (e.g., keratoconjunctivitis sicca associated with Sjögren's syndrome), dry eye disorders including keratoconjunctivitis sicca (Sjögren's-associated or non-Sjögren's-associated), keratitis sicca, sicca syndrome, xerophthalmia, tear film disorder, decreased tear production, aqueous tear deficiency, dry eye associated with graft-versus-host disease, and Meibomian gland dysfunction. Subjects having a dry eye disorder can exhibit inflammation of the eye, and can experience scratchy, stingy, itchy, burning or pressured sensations, irritation, pain, and redness. Dry eye disorders can be associated with excessive eye watering and insufficient tear production. A formulation featured in the invention can be administered to such a subject to ameliorate or prevent the onset or worsening of one or more such symptoms. A formulation featured in the invention can also be used to mitigate pain, e.g., ocular pain, such as pain due to neuroinflammation, in a subject.

The embodiments described herein include methods of treating animals having IL-1-related disorders, for example, dry eye disorders. Dry eye can be a serious disorder in, for example canines. Non-limiting examples of disorders in dogs associated with dry eye include congenital disorders, infections (e.g., canine distemper virus), drug induction (e.g., by sulfa antibiotics), and removal of the tear gland of the third eyelid ("cherry eye"). Dry eye disorders are also commonly seen in certain dog breeds, for example, Cocker Spaniel, Shih Tzu, Lhasa Apso, Bulldog, Schnauzer, and West Highland White Terrier. Other non-limiting examples of animals that can be treated include cats and horses.

The formulations featured herein can also be used to treat other disorders affecting the surface of the eye, such as the cornea. Such disorders include corneal ocular surface inflammatory conditions, corneal neovascularization, keratitis, including peripheral ulcerative keratitis and microbial keratitis. The formulations can be used to treat a subject undergoing corneal wound healing (e.g., a subject having a corneal wound). The formulation can be administered to a subject who is about to receive, undergoing, or recovering from a procedure involving the eye, e.g., corneal transplantation/keratoplasty, keratoprosthesis surgery, lamellar transplantation, selective endothelial transplantation. See, e.g., Dana (2007) Trans Am Ophthalmol Soc 105: 330-43; Dekaris et al. (1999) Curr Eye Res 19(5): 456-9; and Dana et al. (1997) Transplantation 63:1501-7.

The formulation can be used to treat disorders affecting the conjunctiva, including conjunctival scarring disorders and conjunctivitis, e.g., allergic conjunctivitis, for example, severe allergic conjunctivitis. The formulation can be used to treat still other disorders such as pemphigoid syndrome and Stevens-Johnson syndrome. The formulations featured in the invention can be administered to a subject to modulate neovascularization in or around the eye. See, e.g., Dana (2007) Trans Am Ophthalmol Soc 105: 330-43.

The formulations of the present invention can be administered to a subject having an allergic reaction affecting the eye, e.g., a subject experiencing severe allergic (atopic) eye disease such as, e.g., allergic conjunctivitis. For example, the formulation can be administered topically. See also, e.g., Keane-Myers et al. (1999) Invest Ophthalmol Vis Sci, 40(12): 3041-6.

The formulations featured in the invention can be administered to a subject having an autoimmune disorder affecting the eye. Exemplary autoimmune ocular disorders include sympathetic ophthalmia, Vogt-Koyanagi Harada (VKH) syndrome, birdshot retinochoriodopathy, ocular cicatricial pemphigoid, Fuchs' heterochronic iridocyclitis, and various forms of uveitis. The formulations can be administered to a subject to treat any of the foregoing disorders.

The formulations featured in the invention can be administered to a subject who has or is at risk for diabetic retinopathy. See, e.g., Demircan et al. (2006) Eye 20:1366-1369 and Doganay et al. (2006) Eye, 16:163-170

Uveitis.

Uveitis includes acute and chronic forms and includes inflammation of one or more of the iris, the ciliary body, and the choroid. Chronic forms may be associated with systemic autoimmune disease, e.g., Behçet's syndrome, ankylosing spondylitis, juvenile rheumatoid arthritis, Reiter's syndrome, and inflammatory bowel disease. In anterior uveitis, inflammation is primarily in the iris (also iritis). Anterior uveitis can affect subjects who have systemic autoimmune disease, but also subjects who do not have systemic autoimmune disease. Intermediate uveitis involves inflammation of the anterior vitreous, peripheral retina, and ciliary body, often with little anterior or chorioretinal inflammation. Pan planitis results from inflammation of the pars plana between the iris and the choroid. Posterior uveitis involves the uveal tract and primarily the choroid, and is also referred to as choroiditis. Posterior uveitis can be associated with a systemic infection or an autoimmune disease. It can persist for months and even years. The formulations featured in the invention can be administered to a subject to treat any of the foregoing forms of uveitis. See also e.g., Tsai et al. (2009) Mol Vis 15:1542-1552 and Trittibach et al. (2008) Gene Ther. 15(22): 1478-88.

In some embodiments, the formulations featured in the invention are used to treat a subject having or at risk for age-related macular degeneration (AMD). The formulations can be applied topically to the eye, injected (e.g., intravitreally) or provided systemically. See, e.g., Olson et al. (2009) Ocul Immunol Inflamm 17(3):195-200.

A formulation described herein can be administered by any mode to treat an ocular disease. The agent can be delivered by a parenteral mode. Alternatively or in addition, the formulation can be delivered directly to the eye or in the vicinity of the eye. For example, the formulation can be administered topically or intraocularly, e.g., as described herein.

Formulations and Methods for Ocular Delivery

Ophthalmic formulations featured in the invention can be delivered for topical administration, e.g., for administration as a liquid drop, an ointment, or a gel, or for implantation, e.g., into an anterior chamber of the eye or the conjunctival sac. Drops, such as liquid drops, can be delivered using an eye dropper. Gels and ointments can also be administered using a dropper. When formulated for ocular delivery, an active agent (e.g., the chimeric cytokine protein or receptor binding agent) can be present at 0.0001% to 0.1%, 0.001% to 5%, e.g., 0.005% to 0.5%, 0.05% to 0.5%, 0.01% to 5%, 0.1% to 2% or 1% to 5% concentration. In some embodiments, the concentration is 2%, e.g., of P05. In other embodiments, the concentration is 0.5%, e.g., of P05.

In some embodiments, the receptor binding agent, e.g., P05 is formulated on a mg/ml basis, e.g., as described supra. For example, the active agent, e.g., the receptor binding agent, is an IL-1 inhibitor and is present at a concentration of 1-50 mg/ml, 1-25 mg/ml, 1-20 mg/ml, 1-10 mg/ml, 2-8 mg/ml, 3-7 mg/ml, or 4-6 mg/ml. In embodiments, the active agent is present at a concentration of 1 mg/ml, 2 mg/ml, 3 mg/ml, 4 mg/ml, 5 mg/ml, 8 mg/ml, 10 mg/ml, 15 mg/ml, 20 mg/ml, 25 mg/ml, 30 mg/ml, 40 mg/ml, or 50 mg/ml. In embodiments, the active agent, e.g., the IL-1 inhibitor, is present at a concentration of up to 100 mg/ml.

Typically, the ophthalmic formulation is applied directly to the eye including onto the cornea, the eyelid or instillation into the space (cul-de-sac) between the eyeball and the eyelids. The ophthalmic formulation can be designed to mix readily with the lacrimal fluids and spread over the surfaces of the cornea and conjunctiva. With the usual technique of administration, the major portion of the drug is typically deposited in the lower fornix. Capillarity, diffusional forces, and the blinking reflex drive incorporation of the drug in the precorneal film from which it penetrates into and through the cornea.

Ophthalmic formulations featured in the invention can also include one or more other agents, e.g., an anti-inflammatory steroid such as rimexolone, loteprednol, medrysone and hydrocortisone, or a non-steroidal anti-inflammatory. For example, the steroid can be present at a concentration of 0.001% to 1%. In some embodiments, no steroid is present. For example, the receptor binding agent is the only active agent in the formulation.

The formulation can also include one or more of the following components as described herein: surfactants, tonicity agents, buffers, preservatives, co-solvents and viscosity building agents. Tonicity agents can be used to adjust the tonicity of the composition, e.g., to that of natural tears. Tonicity agents, particularly sugars, may also function as thermal stabilizers. In embodiments, potassium chloride, sodium chloride, magnesium chloride, calcium chloride, dextrose and/or mannitol may be added to achieve an appropriate tonicity, e.g., physiological tonicity. Tonicity agents can be added in an amount sufficient to provide an appropriate osmolality as described herein. In embodiments, a tonicity agent is added to provide an osmolality of about 150 mOsm per kg to 450 mOsm per kg or 250 mOsm per kg to 350 mOsm per kg. In embodiments, a tonicity agent is added to provide an osmolality that is isotonic in the eye. In embodiments, a tonicity agent, e.g., sorbitol, is added to provide an osmolality of 270-330 mOsm per kg.

The formulation can also include buffering suitable for ophthalmic delivery and as described herein. The buffer can include one or more buffering components such as a citrate, phosphate, borate, boric acid, succinate, acetate or a pharmaceutically acceptable salt thereof (e.g., sodium phosphate, sodium acetate, sodium citrate, sodium borate, sodium succinate, or sodium acetate), to changes in pH. The buffering component can be used especially under storage conditions, e.g., when the formulation will be subjected to prolonged storage. For example, the buffer can be selected to provide a target pH within the range of pH 5.5-6.5, pH 5.5-6.0, pH 6.0 to 7.5, or pH 6.5 to 7.5. Typically, the buffering agent is a weak buffering agent, wherein the concentration of the buffering components is below 20 mM. In embodiments, the concentration of the buffering components is between about 5 to 20 mM, e.g., 5 to 15 mM, e.g., 5 to 10 mM.

The formulation comprising a therapeutic protein can include an aqueous or phospholipid carrier. Particularly for treating dry eye disorders, the formulation can include agents to provide short-term relief, e.g., compounds that lubricate the eye and assist in tear formation. For example, phospholipid carriers (which include one or more phospholipids) can be used to provide short-term relief. Examples or artificial tears compositions useful as artificial tears carriers include commercial products such as Tears Naturale® (Alcon Labs, Inc., TX USA). For example, per ml, the formulation can include: 1 mg dextran, 70 and 3 mg hydroxypropyl methylcellulose, and optionally a preservative such POLYQUAD® (polyquaternium-1) 0.001% (m/v). Examples of phospholipid carrier formulations include those disclosed in U.S. Pat. Nos. 4,804,539, 4,883,658, 5,075,104, 5,278,151, and 5,578,586.

The formulation can also include other compounds that act as a lubricant or wetting agent. These include viscosity agents such as: monomeric polyols, such as, glycerol, propylene glycol, ethylene glycol; polymeric polyols, such as polyethylene glycol, various polymers of the cellulose family: hydroxypropylmethyl cellulose ("HPMC"), sodium carboxymethyl cellulose, hydroxy propylcellulose ("HPC"), dextrans, such as dextran 70; water soluble proteins, such as gelatin; and vinyl polymers, such as polyvinyl alcohol, polyvinylpyrrolidone, povidone and carbomers, such as carbomer 934P, carbomer 941; carbomer 940, carbomer 974P. Still additional examples include polysaccharides, such as hyaluronic acid and its salts and chondroitin sulfate and its salts, and acrylic acid polymers. In certain embodiments, the formulation has a viscosity between 1 cP to 400 cP.

The formulation, e.g., a vehicle formulation, can be packaged for single or multi-dose use, e.g., in a bottle with an associated dropper or as a set of single-use droppers.

The formulation can include one or more preservatives, e.g., to prevent microbial and fungal contamination during use, and/or one or more detergents, or surfactants, e.g., to solubilize proteins. Exemplary preservatives include: benzalkonium chloride, chlorobutanol, benzododecinium bromide, methyl paraben, propyl paraben, phenylethyl alcohol, edetate disodium, sorbic acid, and polyquaternium-1, and can be included at a concentration of from 0.001 w/v to 1.0% w/v. Typically, a formulation containing a therapeutic protein as described herein is sterile yet free of preservatives.

Exemplary detergents/surfactants include Pluronics®, such as F-68; Triton® surfactants, such as Triton X-100, polysorbates, such as Tween-20 and Tween-80, Elugent™, and Cremophor® polyethoxylated castor oil, as well as tyloxapol, octoxynol 40 and polyoxyl 40 stearate.

In general, detergents and/or surfactants can be included at a concentration of from 0.001% w/v to 1.0% w/v. In some aspects, the formulation is free of detergents.

Ophthalmic packs may be used to give prolonged contact of an ophthalmic formulation with the eye. A cotton pledget is saturated with the formulation and then inserted into the superior or inferior fornix. The formulation may also be administered by the way of iontophoresis. This procedure keeps the solution in contact with the cornea in an eyecup bearing an electrode. Diffusion of the drug is effected by difference of electrical potential. Iontophoretic systems which have been used include Ocuphor® 1 (Iomed Inc., USA); Eyegate® II Delivery Systeml (EyeGate Pharma, USA); and Visulex®1 (Aciont Inc., USA). See Amo and Urtti, Drug Discovery Today, 13:143 (2008).

Another strategy for sustained ocular delivery is the use of gelifying agents. These materials can be delivered in a liquid form, as an eye drop or intraocular injection. After instillation the polymer undergoes a phase change and forms a semi-solid or solid matrix that releases the drug over prolonged period. The phase transition can be induced by changes in the temperature, ion concentration, or pH.

For topical ocular use, the gel forming solutions, such as Timoptic®-XE1 (Merck and Co. Inc., USA), which contains Gelrite® (purified anionic heteropolysaccharide from gellan gum); Pilogel®1 (Alcon, Inc., Switzerland) eye drops contain poly(acrylic acid); and Azasite®1 (Insite Vision, USA) have been tested clinically. These materials enhance the drug retention relative to the conventional eye drops and lead to increased drug absorption into the eye and reduced dosing frequency. See Amo and Urtti, Drug Discovery Today, 13:135-143 (2008).

A formulation featured in the invention can be delivered by injection, e.g., intravitreal, periocular, or subconjunctival injection. The formulation can be injected underneath the conjunctiva facilitating passage through the sclera and into the eye by simple diffusion. The formulation can also be injected underneath the conjunctiva and the underlying Tenon's capsule in the more posterior portion of the eye to deliver the agent to the ciliary body, choroid, and retina. The formulation may also be administered by retrobulbar injection.

In embodiments, a formulation provided herein is administered intravitreally. In embodiments, the formulation does not comprise CMC.

Evaluation

With respect to dry eye and other surface disorders, subjects can be evaluated using one or more of the approaches known in the art, for example, the Ocular Surface Disease Index (OSDI), corneal and conjunctival staining, and the Schirmer test. When the OSDI is used, a negative change from baseline indicates an improvement in vision-related function and the ocular inflammatory disorders.

For corneal fluorescein staining, saline-moistened fluorescein strips or 1% sodium fluorescein solution are used to stain the tear film. Typically, the entire cornea is then examined using slit-lamp evaluation with a yellow barrier filter (#12 Wratten) and cobalt blue illumination. Staining can be graded, e.g., according to the NEI scale, the Oxford Schema, or a modified Oxford Schema. Typically, staining is graded according to the NEI scale, which is a 15 point scale where the cornea is divided into 5 sections (a central circular section, and 4 quadrants surrounding the central corneal section which are referred to as inferior, superior, nasal and temporal quadrants) each of which is scored from 0-3 for punctate staining to yield a maximum possible score of 15.

Conjunctival staining is likewise a measure of epithelial disease or break in the epithelial barrier of the ocular surface. Conjunctival staining is performed under the slit-lamp using lissamine green. Saline-moistened strip or 1% lissamine green solution is used to stain the tear film, and interpalpebral conjunctival staining is evaluated more than 30 seconds but less than two minutes later. Using white light of moderate intensity, only the interpalpebral region of the nasal and temporal conjunctival staining is graded, e.g., using the Oxford Schema.

The Schirmer test is performed in the presence or in the absence of anesthesia by placing a narrow filter-paper strip (5×3.5 mm strip of Whatman #41 filter paper) in the inferior cul-de-sac. This test is conducted in a dimly lit room. The patient gently closes his/her eyes until five minutes have elapsed and the strips are removed. Because the tear front will continue advancing a few millimeters after it has been removed from the eyes, the tear front is marked with a ball-point pen at precisely five minutes. Aqueous tear production is measured by the length in millimeters that the strip wets during 5 minutes. Results of 10 mm or less for the Schirmer test without anesthesia and 5 mm or less for the Schirmer test with anesthesia are considered abnormal. A positive change from baseline indicates improvement of one or more symptoms of an ocular inflammatory disorder described herein.

Dry Eye Disease Models.

Efficacy of the formulations featured in the invention can be evaluated in a mouse model for dry eye disease. Dry eye can be induced in mice by subcutaneous injection of scopolamine and then placement of the mice in controlled-environment chambers. By way of a specific example, normal healthy 6 to 10 weeks old female C57BL/6 mice can be induced to have dry eye by continuous exposure to dry environment in a controlled environmental chamber. The chamber has low relative humidity of less than 30% (generally about 19%), high airflow (15 liters/minute) and constant temperature (about 22° C.). The mice placed in the chamber are also treated with scopolamine to inhibit tear secretion. Sustained-release transdermal scopolamine patches can be obtained from Novartis (Summit, N.J.). One-fourth of a patch is applied to the depilated mid-tail of mice every 48 hours. The combination of the controlled environmental chamber and scopolamine produces severe dry eye in a relative short period of time (about 2-4 days). The controlled environmental chamber can be prepared as described in Barbino et al. (Invest Ophthal Vis Sci, 46: 2766-2711 (2005)), and enables control of air flow, humidity, and temperature.

Mice can be monitored for signs of dry eye, e.g., by performing: a) cotton thread test to measure aqueous tear production, which is generally decreased in patients with dry eye; b) corneal fluorescein staining which is a marker of corneal surface damage; and general ophthalmic examination.

Cotton Thread Test: Tear production can be measured with cotton thread test, impregnated with phenol red (Zone-Quick, Lacrimedics, Eastsound, Wash.). Under a magnifying fluorescent lamp, the thread is held with jeweler forceps and placed in the lateral cantus of the conjunctival fornix of the right eye for 30 or 60 seconds. The tear distance in mm is read under a microscope using the scale of a hemacytometer.

Corneal Fluorescein Staining: Corneal fluorescein staining can be evaluated by applying 1.0 ml of 5% fluorescein by a micropipette into the inferior conjunctival sac of the eye. The cornea is examined with a slit lamp biomicroscope using cobalt blue light 3 minutes after the fluorescein instillation. Punctuate staining is recorded in a masked fashion using a standardized National Eye Institute (NEI) grading system of 0-3 for each of the five areas in which the corneal surface has been divided.

EQUIVALENTS

All technical features can be individually combined in all possible combinations of such features.

The invention may be embodied in other specific forms without departing from the spirit or essential characteristics thereof. The foregoing embodiments are therefore to be considered in all respects illustrative rather than limiting on the invention described herein.

The entire content of all references cited herein is hereby incorporated in its entirety.

The following non-limiting examples further illustrate embodiments of the inventions described herein.

EXAMPLES

Example 1: Examples of Therapeutic Proteins, e.g., Chimeric Proteins

Nucleic acids encoding the proteins with the amino acid sequences listed in Table 1 (below) were constructed in a pET vector containing a T7 promoter and ampicillin (pET31 series) or kanamycin resistance genes (pET28 series) (EMD Chemicals, Gibbstown, N.J., USA), and expressed. Examples of coding sequences that can be used for expression are provided in Table 2.

TABLE 1

| Exemplary chimeric proteins | SEQ ID NO: |
|---|---|
| P01 APVRSLAFRIWDVNQKTFYLRNNQLVAGYLQGPNVNLEEKIDVSFVQGEESNDK IPVALGIHGGKMCLSCVKSGDETRLQLEAVDPKNYPKKKMDKRFAFIRSDSGPT TSFESAACPGWFLCTAMEADQPVSLTNMPDEGVMVTKFYMQFVSS | 1 |
| P02 APVRSLAFRIWDVNQKTFYLRNNQLVAGYLQGPNVNLEEKIDVSFVQGEESNDK IPVALGIHGGKMCLSCVKSGDETRLQLEAVDPKNYPKKKMEKRFVFNKIEINNK LSFESAACPGWFLCTAMEADQPVSLTNMPDEGVMVTKFYMQFVSS | 2 |
| P03 APVRSLAFRIWDVNQKTFYLRNNQLVAGYLQGPNVNLEEKFSMSFVQGEESNDK IPVALGLKEKNLYLSCVLKDDKPTLQLESVDPKNYPKKKMEKRFVFIRSDSGPT TSFESAACPGWFLCTAMEADQPVSLTNMPDEGVMVTKFTMQFVSS | 3 |
| P04 APVRSLAFRIWDVNQKTFYLRNNQLVAGYLQGPNVNLEEKFSMSFVQGEESNDK IPVALGLKEKNLYLSCVLKDDKPTLQLESVDPKNYPKKKMEKRFVFNKIEINNK LEFESAACPGWFLCTAMEADQPVSLTNMPDEGVMVTKFTMQFVSS | 4 |
| P05 APVRSLNCRIWDVNQKTFYLRNNQLVAGYLQGPNVNLEEKFSMSFVQGEESNDK IPVALGLKEKNLYLSCVLKDDKPTLQLESVDPKNYPKKKMEKRFVFNKIEINNK LEFESAQFPNWFLCTAMEADQPVSLTNMPDEGVMVTKFYMQFVSS | 5 |
| P06 APVRSLNCTLWDVNQKTFYLRNNQLVAGYLQGPNVEQQVVFSMSFVQGEESNDK IPVALGLKEKNLYLSCVLKDDKPTLQLESVDPKNYPKKKMEKRFVFNKIEINNK LEFESAQFPNWYISTSMEADQPVFLGGTKGGQDITDFTMQFVSS | 6 |
| P07 APVRSLNCRIWDVNQKTFYLRNNQLVAGYLQGPNVNLEEKFSMSFVQGEESNDK IPVALGLKEKNLYLSCVLKDDKPTLQLESVDPKNYPKKKMEKRFVFNKIEINNK LEFESAQFPNWFLCTAMEADQPVSLTNMPDEGQDITDFTMQFVSS | 7 |

Exemplary nucleic acid sequences encoding the above proteins are listed in Table 2. In some embodiments, the nucleic acid sequence further includes an ATG prior to the first nucleotide listed below. In some embodiments, the nucleic acid sequence further includes a stop codon (such as TAA, TAG, or TGA) after the last nucleotide listed below.

TABLE 2

| Nucleic acids encoding exemplary chimeric proteins | SEQ ID NO: |
|---|---|
| P01 GCACCTGTACGATCACTGGCCTTCAGAATCTGGGATGTTAACCAGAAGACCTTC TATCTGAGGAACAACCAACTAGTTGCTGGATACTTGCAAGGACCAAATGTCAAT TTAGAAGAAAAGATAGATGTGTCCTTTGTACAAGGAGAAGAAAGTAATGACAAA ATACCTGTGGCCTTGGGCATCCATGGAGGGAAGATGTGCCTGTCCTGTGTCAAG TCTGGTGATGAGACCAGACTCCAGCTGGAGGCAGTTGATCCCAAAAATTACCCA AAGAAGAAGATGGACAAGCGCTTCGCCTTCATCCGCTCAGACAGCGGCCCCACC ACCAGTTTTGAGTCTGCCGCCTGCCCCGGTTGGTTCCTCTGCACAGCGATGGAA GCTGACCAGCCCGTCAGCCTCACCAATATGCCTGACGAAGGCGTCATGGTCACC AAATTCTACATGCAATTTGTGTCTTCC | 8 |
| P02 GCACCTGTACGATCACTGGCCTTCAGAATCTGGGATGTTAACCAGAAGACCTTC TATCTGAGGAACAACCAACTAGTTGCTGGATACTTGCAAGGACCAAATGTCAAT TTAGAAGAAAAGATAGATGTGTCCTTTGTACAAGGAGAAGAAAGTAATGACAAA ATACCTGTGGCCTTGGGCATCCATGGAGGGAAGATGTGCCTGTCCTGTGTCAAG TCTGGTGATGAGACCAGACTCCAGCTGGAGGCAGTTGATCCCAAAAATTACCCA | 9 |

TABLE 2-continued

| Nucleic acids encoding exemplary chimeric proteins | SEQ ID NO: |
|---|---|
| AAGAAGAAGATGGAAAAGCGATTTGTCTTCAACAAGATAGAAATCAATAACAAG<br>CTGAGTTTTGAGTCTGCCGCCTGCCCCGGTTGGTTCCTCTGCACAGCGATGGAA<br>GCTGACCAGCCCGTCAGCCTCACCAATATGCCTGACGAAGGCGTCATGGTCACC<br>AAATTCTACATGCAATTTGTGTCTTCC | |
| P03 GCACCTGTACGATCACTGGCCTTCAGAATCTGGGATGTTAACCAGAAGACCTTC<br>TATCTGAGGAACAACCAACTAGTTGCTGGATACTTGCAAGGACCAAATGTCAAT<br>TTAGAAGAAAAGTTCTCCATGTCCTTTGTACAAGGAGAAGAAAGTAATGACAAA<br>ATACCTGTGGCCTTGGGCCTCAAGGAAAAGAATCTGTACCTGTCCTGCGTGTTG<br>AAAGATGATAAGCCCACTCTACAGCTGGAGAGTGTAGATCCCAAAAATTACCCA<br>AGAAGAAGATGGAAAAGCGATTTGTCTTCATCCGCTCAGACAGCGGCCCCACC<br>ACCAGTTTTGAGTCTGCCGCCTGCCCCGGTTGGTTCCTCTGCACAGCGATGGAA<br>GCTGACCAGCCCGTCAGCCTCACCAATATGCCTGACGAAGGCGTCATGGTCACC<br>AAATTCACCATGCAATTTGTGTCTTCC | 10 |
| P04 GCACCTGTACGATCACTGGCCTTCAGAATCTGGGATGTTAACCAGAAGACCTTC<br>TATCTGAGGAACAACCAACTAGTTGCTGGATACTTGCAAGGACCAAATGTCAAT<br>TTAGAAGAAAAGTTCTCCATGTCCTTTGTACAAGGAGAAGAAAGTAATGACAAA<br>ATACCTGTGGCCTTGGGCCTCAAGGAAAAGAATCTGTACCTGTCCTGCGTGTTG<br>AAAGATGATAAGCCCACTCTACAGCTGGAGAGTGTAGATCCCAAAAATTACCCA<br>AAGAAGAAGATGGAAAAGCGATTTGTCTTCAACAAGATAGAAATCAATAACAAG<br>CTGGAATTTGAGTCTGCCGCCTGCCCCGGTTGGTTCCTCTGCACAGCGATGGAA<br>GCTGACCAGCCCGTCAGCCTCACCAATATGCCTGACGAAGGCGTCATGGTCACC<br>AAATTCACCATGCAATTTGTGTCTTCC | 11 |
| P05 GCACCTGTACGATCACTGAACTGCAGAATCTGGGATGTTAACCAGAAGACCTTC<br>TATCTGAGGAACAACCAACTAGTTGCTGGATACTTGCAAGGACCAAATGTCAAT<br>TTAGAAGAAAAGTTCTCCATGTCCTTTGTACAAGGAGAAGAAAGTAATGACAAA<br>ATACCTGTGGCCTTGGGCCTCAAGGAAAAGAATCTGTACCTGTCCTGCGTGTTG<br>AAAGATGATAAGCCCACTCTACAGCTGGAGAGTGTAGATCCCAAAAATTACCCA<br>AAGAAGAAGATGGAAAAGCGATTTGTCTTCAACAAGATAGAAATCAATAACAAG<br>CTGGAATTTGAGTCTGCCCAGTTCCCCAACTGGTTCCTCTGCACAGCGATGGAA<br>GCTGACCAGCCCGTCAGCCTCACCAATATGCCTGACGAAGGCGTCATGGTCACC<br>AAATTCTACATGCAATTTGTGTCTTCC | 12 |
| P06 GCACCTGTACGATCACTGAACTGCACGCTCTGGGATGTTAACCAGAAGACCTTC<br>TATCTGAGGAACAACCAACTAGTTGCTGGATACTTGCAAGGACCAAATGTCGAG<br>CAACAAGTGGTGTTCTCCATGTCCTTTGTACAAGGAGAAGAAAGTAATGACAAA<br>ATACCTGTGGCCTTGGGCCTCAAGGAAAAGAATCTGTACCTGTCCTGCGTGTTG<br>AAAGATGATAAGCCCACTCTACAGCTGGAGAGTGTAGATCCCAAAAATTACCCA<br>AAGAAGAAGATGGAAAAGCGATTTGTCTTCAACAAGATAGAAATCAATAACAAG<br>CTGGAATTTGAGTCTGCCCAGTTCCCCAACTGGTACATCAGCACCTCTATGAA<br>GCTGACCAGCCCGTCTTCCTGGGAGGGACCAAAGGCGGCCAGGATATAACTGAC<br>TTCACCATGCAATTTGTGTCTTCC | 13 |
| P07 GCACCTGTACGATCACTGAACTGCAGAATCTGGGATGTTAACCAGAAGACCTTC<br>TATCTGAGGAACAACCAACTAGTTGCTGGATACTTGCAAGGACCAAATGTCAAT<br>TTAGAAGAAAAGTTCTCCATGTCCTTTGTACAAGGAGAAGAAAGTAATGACAAA<br>ATACCTGTGGCCTTGGGCCTCAAGGAAAAGAATCTGTACCTGTCCTGCGTGTTG<br>AAAGATGATAAGCCCACTCTACAGCTGGAGAGTGTAGATCCCAAAAATTACCCA<br>AAGAAGAAGATGGAAAAGCGATTTGTCTTCAACAAGATAGAAATCAATAACAAG<br>CTGGAATTTGAGTCTGCCCAGTTCCCCAACTGGTTCCTCTGCACAGCGATGGAA<br>GCTGACCAGCCCGTCAGCCTCACCAATATGCCTGACGAAGGCCAGGATATAACT<br>GACTTCACCATGCAATTTGTGTCTTCC | 14 |

The proteins can include a range of different residues from IL-1β and IL-1Ra as illustrated below. Among the examples P01, P02, P03, P04, and P05, the cytokine domains can have 48-70% residues from IL-1β and 55-78% residues from IL-1Ra. Because a number of amino acid residues are conserved between the two proteins, the sum of the percentage identity to IL-1β and to IL-1Ra can be greater than 100%.

TABLE 6

| | IL-1β residues | IL-1RA residues | Total residues | % IL-1β | % IL-1RA |
|---|---|---|---|---|---|
| P06 | 130 | 62 | 152 | 85.5 | 40.8 |
| P07 | 113 | 80 | 153 | 73.9 | 52.3 |
| P05 | 108 | 85 | 153 | 70.6 | 55.6 |

TABLE 6-continued

| | IL-1β residues | IL-1RA residues | Total residues | % IL-1β | % IL-1RA |
|---|---|---|---|---|---|
| P04 | 104 | 89 | 153 | 68.0 | 58.2 |
| P03 | 94 | 99 | 153 | 61.4 | 64.7 |
| P02 | 85 | 108 | 153 | 55.6 | 70.6 |
| P01 | 74 | 119 | 153 | 48.4 | 77.8 |

Other examples of therapeutic proteins include IL-1Ra (e.g., anakinra), canakinumab, gevokizumab, rilanacept, or an anti-IL-1R antibody (e.g., as produced by Amgen).

Example 2: Expression and Purification of Chimeric Proteins

Proteins that contain a hexa-histidine tag (SEQ ID NO:23) were expressed in *E. coli* cells BL21(DES) strain by induction with 1 mM isopropyl 3-D-1-thiogalactopyranoside (IPTG) at 37° C. for 3 hours in LB broth media. The cells were lysed in 20-50 mM Tris, 0.5 M NaCl, 2.5 mM EDTA, 0.1% Triton X-100, pH 8.0. Lysate was dialyzed against 1.25×PBS containing 0.1% polysorbate 80, then sterile filtered through a 0.8/0.2 µm filter before being subjected to immobilized ion affinity chromatography (IMAC) using a HisTrap HP® pre-packed column (GE Healthcare, Piscataway N.J., USA). The column was equilibrated in 50 mM phosphate, 500 mM NaCl, pH 7.1, loaded, and washed with same buffer. It was pre-eluted with 25 mM imidazole and eluted with 125 mM imidazole in same buffer. Eluted protein was dialyzed extensively against 1.25×PBS, 0.1% polysorbate 80, pH 7.4.

The protein was loaded in 20 mM sodium phosphate, 0.5 M NaCl 10 mM imidazole, pH 7.4 buffer. It was eluted with 200 mM imidazole, 20 mM sodium phosphate, 0.5 M NaCl pH 7.4 buffer. Eluted protein was dialyzed extensively against PBS, 0.1% polysorbate 80, pH 7.4, concentrated using an Amicon Ultra® (10K) filter, and stored at 40 or −80° C.

Proteins lacking a hexa-histidine tag (SEQ ID NO:23) were purified by ion exchange chromatography. P05 protein was purified by ion exchange chromatography. Lysate from expressing cells was applied to a GigaCapS™ column (Tosoh Bioscience LLC, King of Prussia, Pa., USA) at low pH (approximately pH 5.5) in the absence of salt (conductivity approximately 1 mS/cm). The column was then eluted by a pH gradient (Buffer A=10 mM acetic acid, pH 5.5; Buffer B=20 mM Tris pH 8). A 5 ml fraction containing the eluted protein was then diluted with 5 ml of $H_2O$ and 5 ml of 20 mM Tris pH 8) and then applied to Capto™ Q resin (GE Healthcare, Piscataway N.J., USA) and eluted with a 0 mM to 250 mM NaCl gradient in 20 mM Tris pH 8.0. The eluted protein was dialyzed extensively against 1.25×PBS 0.1% TWEEN® 80 or 1.25×PBS lacking TWEEN® and stored. See FIG. 1. P03 and P04 proteins were purified using similar methods.

Cells expressing P05 were also grown in TEKNOVA™ Terrific Broth with animal free soytone (# T7660) supplemented with 10 g/L glucose, 10 mM $MgSO_4$, trace elements (1 mg/ml TEKNOVA™ 1000X Trace Elements, # T1001), and antibiotic in a Sartorius 2L BIOSTAT™ A+ and were induced at OD 35-40 with 1 mM IPTG for about 6 hours. Cells were grown at 37° C. with 30% dissolved oxygen at pH 7.0, and agitation at 200-800 rpm with oxygen sparge at 2 L/min. Cells were fed 9 g glucose/L/hr when glucose was depleted as detected by a pH increase. Feed was reduced to 6 g glucose/L/hr when the pH decreased (about 2.5 hrs after induction).

Cells were collected and lysed in lysis buffer (20 mM Tris, 10 mM EDTA, 0.1% Triton, pH 8.0; 20 mM Tris, 10 mM EDTA, 0.1% Triton, pH 7.0; 50 mM MOPS, 10 mM EDTA, 0.1% Triton, pH 6.5; or 50 mM MOPS, 10 mM EDTA, 0.1% Triton, pH 6.0). Lysate is loaded onto Poros® XS cation ion exchange media (Life Technologies Corp., Carlsbad Calif. USA) at pH 5.3 and 3 mS/cm (35 mg product per ml column resin).

In an exemplary procedure, P05 protein is eluted by a step to pH 7.0 using buffer containing 100 mM MOPS 25 mM NaCl pH 7.0. The first eluting peak was discarded, and the second eluting peak was collected in pools and contained P05 protein. Early pools are enriched for intact P05 protein relative to a des-Ala species. This eluted material is then flowed over Capto®Q anion exchange resin. The flow through, which contains intact P05 protein, is collected.

In another exemplary procedure, the media is washed with 100 mM MOPS 20 mM NaCl pH 6.0. P05 protein is eluted by a step to pH 6.0 using buffer containing 100 mM MOPS 50-58 mM NaCl pH 6.0. The first eluting peak was separated from subsequent peaks and contained intact P05 protein. This eluted material is then flowed over Capto®Q anion exchange resin. The flow through, which contains intact P05 protein, is collected.

Example 3: Cell-Based Assays

The proteins or supernatants containing the proteins were evaluated in a cell-based assay for IL-1 activity. HEK-Blue™ IL-1β responsive cells were used to monitor IL-1β activity (available from InvivoGen Inc., San Diego Calif., USA). These cells include a secreted embryonic alkaline phosphatase (SEAP) reporter gene under the control of the IFN-β minimal promoter fused to five NF-kB and five AP-1 binding sites. IL-1β engagement of IL-1 receptors on the cell surface led to NF-kB activation and SEAP production. The SEAP report can be detected, e.g., using QUANTI-Blue™ (InvivoGen Inc., San Diego Calif., USA) and spectrophotometric analysis. A HEK-Blue IL-1β cell suspension was prepared from cells cultured to 70-80% confluence. The resuspended cells were adjusted to ~330,000 cells/ml in fresh growth medium (DMEM, 4.5 g/11 glucose, 2 mM L-glutamine, 10% (v/v) heat-inactivated fetal bovine serum (30 minutes at 56° C.), 50 U/ml penicillin, 50 mg/ml streptomycin, 100 mg/ml Normocin®T).

Reagents were added to wells of a flat-bottom 96-well cell culture plate: 10 µl of IL-1β at 20 ng/ml, 10 µl of the agent of interest, and 30 µl of cell culture medium to a final volume of 50 µl. Positive and negative control samples were prepared in parallel. Then 150 µl of HEK-Blue IL-1β cell suspension (~50,000 cells) was added to each well and the plate was cultured overnight at 37° C. in 5% $CO_2$ tissue culture incubator. Generally, the final IL-1β concentration (in the 200 µl final volume) was 0.1 ng/ml. IL-1β activity was evaluated the next day (12-15 hours later). Prior to quantitation, the QUANTI-Blue™ reagent was prepared according to the manufacturer's instructions. A flat bottomed 96-well assay plate was prepared in which 150 µl of QUANTI-Blue™ solution was added to each well. 50 µl of conditioned media from the wells of the 96 well tissue culture plate was added to each well of the assay plate. The plate was incubated at 37° C. for approximately 15-20 minutes. SEAP levels were then measured using a spectrophotometer at 620-655 nm.

Results.

Figure 2A:
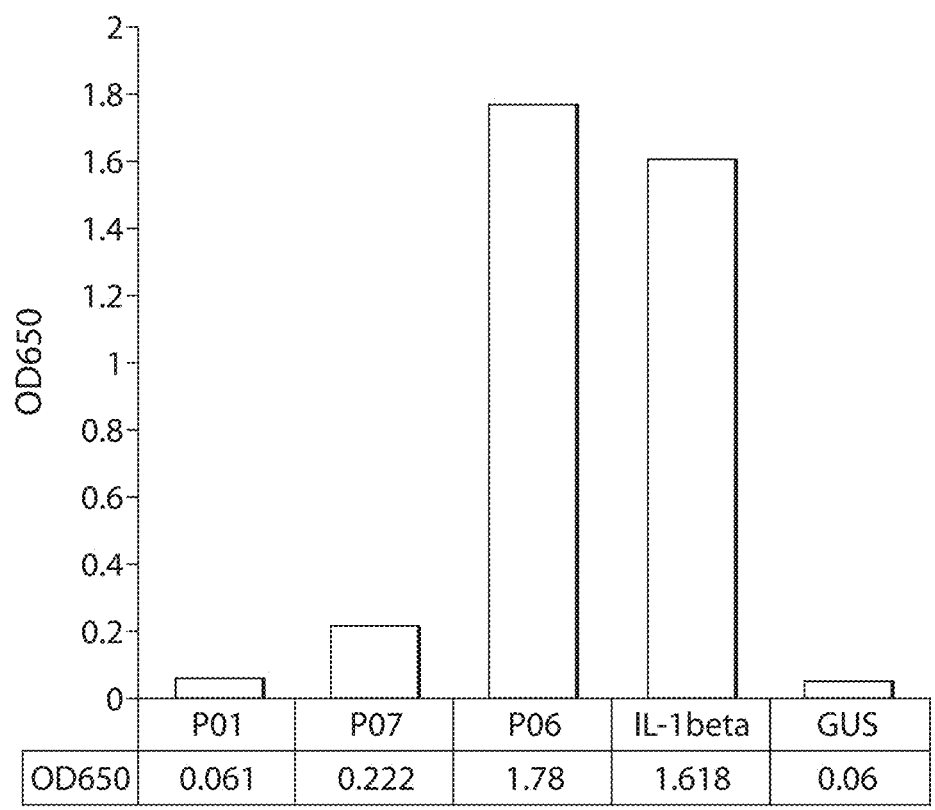
FIG. 2A is a table and accompanying bar graph illustrating the results of an experiment testing the ability of the P06, P07, and P01 proteins to agonize signaling relative to IL-1β and a negative control, β-glucuronidase (GUS) protein.
Figure 2B:
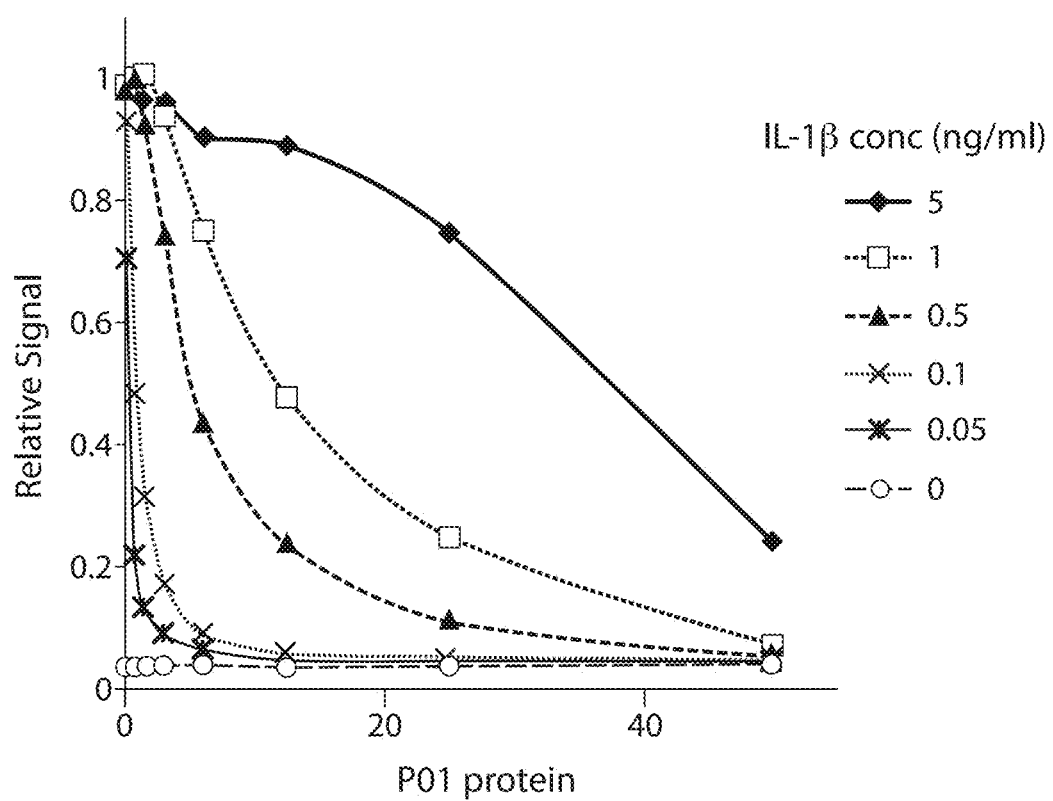
FIG. 2B is a graph depicting the results of an experiment testing the ability of P01 to antagonize IL-1β activity at various IL-1β concentrations.

As shown in FIG. 2A, in this assay, the P06 protein behaved as an IL-1RI agonist, the P07 protein behaved as a partial agonist, and the P01 protein failed to agonize. In fact, the P01 protein behaved as an antagonist when assayed in the presence of IL-1β. FIG. 2B shows antagonism of IL-1β activity by P01 at a range of IL-1β protein concentrations using the HEKBlue™ cell assay described herein. Antagonism increased with increasing amounts of P01 (x-axis reflects microliters of supernatant containing P01).

Figure 3A:
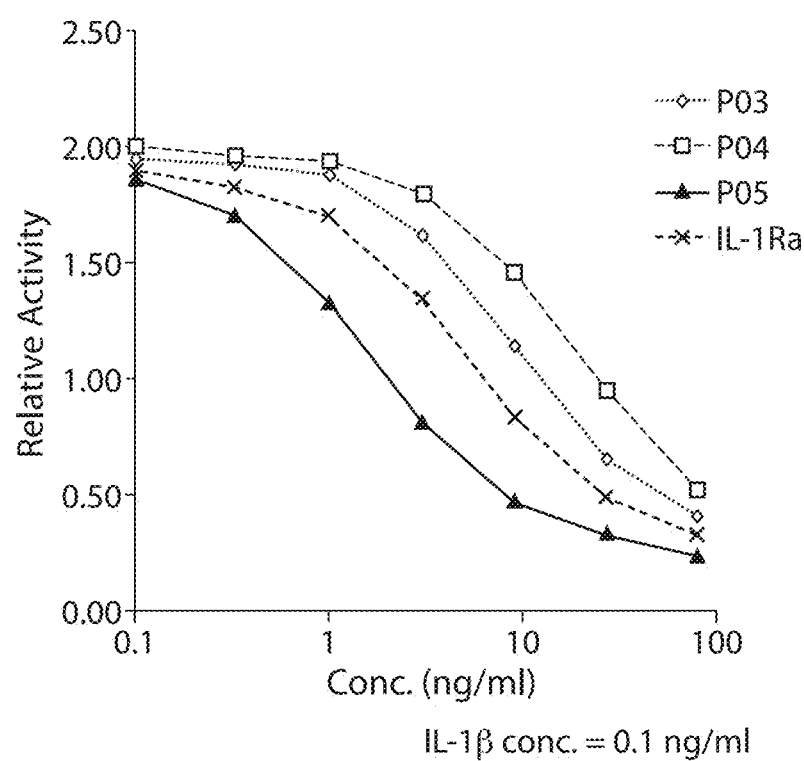
FIG. 3A is a graph depicting the results of an experiment testing antagonism of IL-1 by P03 (hexa-histidine tagged (SEQ ID NO: 23)), P04 (hexa-histidine tagged (SEQ ID NO: 23)), P05 (hexa-histidine tagged (SEQ ID NO: 23)), and IL-1Ra in the presence of 0.1 ng/ml IL-1β (human).
Figure 3B:
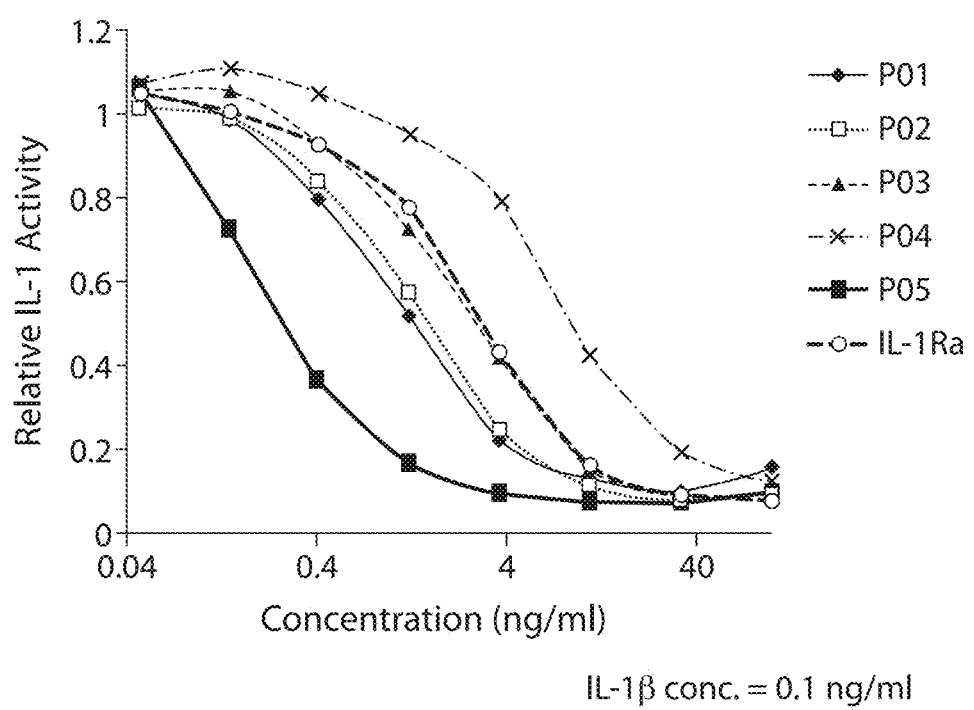
FIG. 3B is a graph depicting the results of an experiment testing antagonism of IL-1β by lysates containing untagged forms of P01, P02, P03, P04, and P05, and IL-1Ra in the presence of 0.1 ng/ml IL-1β (human) and using estimates of the concentration of protein in the respective lysates.

The proteins P01, P02, P03, P04, and P05 each antagonized IL-1β activity. See FIG. 3A and FIG. 3B, for example. The IC50 of P05 was less than about 5 ng/ml. P05 was test for ability to agonize IL-1RI in this assay and was not observed to have any detectable agonistic activity even at the highest concentrations tested, 1 mg/ml. P01, P02, P03, P04, and P05 also inhibited IL-1β induced IL-6 expression in MG-63 cells, a human osteosarcoma cell line that is responsive to IL-1β. In a murine model of dry eye disease, hexa-histidine tagged (SEQ ID NO:23) P05 was observed to have biological activity. See also Example 9 below regarding untagged P05.

Example 4: Binding Properties of Chimeric Proteins

The binding properties of proteins for soluble recombinant human IL-1RI (corresponding to the extracellular domain of IL-1RI) were evaluated using surface plasmon resonance with a Reichert SR7000DC Dual Channel SPR system. Binding was evaluated in phosphate buffered saline with 0.005% Tween 20. IL-1β was observed to have a $K_D$ of between 8-9 nM and a dissociation constant ($K_d$) of between $2\text{-}3\times10^{-3}$ s$^{-1}$, and in another experiment a $K_D$ of about 2 nM, an association constant of $1.3\text{-}1.5\times10^6$ M$^{-1}$s$^-$, and a dissociation constant ($K_d$) of about $2.9\text{-}3.0\times10^{-3}$ s$^{-1}$. The P01 protein bound with similar association kinetics as IL-1β, but did not dissociate during of the dissociation phase of the binding experiment (about 180 seconds). Thus, the P01 protein bound to IL-1RI with a greater affinity than did IL-1β under similar conditions.

Binding of IL-1Ra was observed to have a $K_D$ of about 0.33 nM, an association constant ($K_a$) of about $2\times10^5$ M$^{-1}$s$^{-1}$, and a dissociation constant ($K_d$) of about $6.6\times10^{-5}$ s$^{-1}$. Chimeric cytokine domains P01, P02, P03, P04, and P05 were observed to have $K_D$ ranging from about 12-1700 pM, an association constant ($K_a$) ranging from about $3\times10^4$ M$^{-1}$s$^{-1}$ to $3\times10^6$ M$^{-1}$s$^{-1}$, and a dissociation constant ($K_d$) ranging from about $2\times10^{-5}$ to $1\times10^{-3}$ s$^{-1}$. See Table 3 below.

TABLE 3

| Protein | $k_a$ (M$^{-1}$s$^{-1}$) | $K_d$ (s$^{-1}$) | $K_D$ (pM) |
|---|---|---|---|
| IL-1β | $1.47 \times 10^6$ M$^{-1}$s$^{-1}$ | $2.95 \times 10^{-3}$ s$^{-1}$ | 2010 |
| IL-1Ra | $2.01 \times 10^5$ M$^{-1}$s$^{-1}$ | $6.58 \times 10^{-5}$ s$^{-1}$ | 326 |
| P01 | $4.93 \times 10^4$ M$^{-1}$s$^{-1}$ | $2.32 \times 10^{-5}$ s$^{-1}$ | 470 |
| P02 | $3.39 \times 10^4$ M$^{-1}$s$^{-1}$ | $2.16 \times 10^{-5}$ s$^{-1}$ | 636 |
| P03 | $4.1 \times 10^6$ M$^{-1}$s$^{-1}$ | $1.2 \times 10^{-3}$ s$^{-1}$ | 290 |
| P04 | $3.00 \times 10^4$ M$^{-1}$s$^{-1}$ | $5.14 \times 10^{-4}$ s$^{-1}$ | 1714 |
| P05 | $3.47 \times 10^6$ M$^{-1}$s$^{-1}$ | $4.15 \times 10^{-5}$ s$^{-1}$ | 12 |
| P06 | $4.8 \times 10^6$ M$^{-1}$s$^{-1}$ | $1.7 \times 10^{-3}$ s$^{-1}$ | 410 |
| P07 | $1.58 \times 10^4$ M$^{-1}$s$^{-1}$ | $1.46 \times 10^{-3}$ s$^{-1}$ | 92553 |

Example 5: Additional Examples of Chimeric Proteins

Additional exemplary chimeric IL-1 family proteins also include the following:

P08
SEQ ID NO: 15
APVRSLAFRIWDVNQKTFYLRNNQLVAGYLQGPNVNLEEKFSMSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFYMQF

VSS

P09
SEQ ID NO: 16
APVRSQAFRIWDVNQKTFYLRNNQLVAGYLQGPNVNLEEKFSMSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFYMQF

VSS

P10
SEQ ID NO: 17
APVRSLAFRIWDVNQKTFYLRNNQLVAGYLQGPNVNLEEKIDVSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFYMQF

VSS

P11
SEQ ID NO: 18
APVRSLNCRIWDVNQKTFYLRNNQLVAGYLQGPNVNLEEKIDVSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFYMQF

VSS

P12
SEQ ID NO: 19
APVRSLNCRIWDVNQKTFYLRNNQLVAGYLQGPNVNLEEKFSMSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFTMQF

VSS

P13
SEQ ID NO: 20
APVRSLAFRIWDVNQKTFYLRNNQLVAGYLQGPNVNLEEKFSMSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFYFQE

D

P14
SEQ ID NO: 21
APVRSLNCRIWDVNQKTFYLRNNQLVAGYLQGPNVNLEEKFSMSFVQGEE

SNDKIPVALGLKEKNLYLSCVLKDDKPTLQLESVDPKNYPKKKMEKRFVF

NKIEINNKLEFESAQFPNWFLCTAMEADQPVSLTNMPDEGVMVTKFYFQE

D

The polypeptide below is a chimeric domain that includes at least two segments from IL-1α and at least two segments from IL-1Ra.

SEQ ID NO: 22
SAPFSFLSNVKYNFMRIIKYEFRIWDVNQKTFYLRNNQLVAGYLQGPNVN
LEEKFDMGAYKSSKDDAKITVILRISKTQLYVTAQDEDQPVLLKEMPEIP
KTITGSETNLLFFWETHGTKNYFTSVAHPNLFLCTAMEADQPVSLTNMPD
EGVMVTKFYILENQA

Example 6: Formulation Example

An exemplary formulation according to the present invention is described as follows:

A formulation having P05 protein present in a concentration of 25 g/l; carboxymethylcellulose is present in a concentration of 0.25% w/v; poloxamer 188 is present in a concentration of 0.1% w/v; sorbitol is present in a concentration of 5% w/v; sodium phosphate is present in a concentration of 10 mM; arginine and/or glutamic acid are present in a concentration of 100 mM. The formulation has a pH of 6.5. The formulation is tested for stability at two weeks at room temperature and up to at least twelve months storage stability at 2-8° C. as measured using one or more of reverse phase HPLC (RP-HPLC); weak cation exchange HPLC (WCEX-HPLC); spectrophotometry (A280); and visual assays.

Example 7: Formulation Example and Stability Studies

Formulations of P05 (also known as EBI-005) utilized in Phase 1 clinical studies were aqueous formulations that contained sodium carboxymethylcellulose in a concentration of 0.25% w/v; poloxamer 188 in a concentration of 0.1% w/v; sorbitol in a concentration of 5% w/v; sodium phosphate in a concentration of 10 mM, and P05 in a concentration of either 5 or 20 mg/mL. The formulation has a pH of about 6.5. These formulations were tested for stability with the following measurements: appearance, pH, osmolality, content by spectrophotometry (A280), SDS-PAGE non-reduced, SDS-PAGE reduced; size exclusion HPLC (SE HPLC); reverse phase HPLC (RP-HPLC); WCEX-HPLC; potency; and container integrity (CIT). These tests were carried out (1) at release (0 months); (2) after storage at 5±3° C. for 1 month, 2 months, 3 months, 4 months, 5 months, and 6 months; (3) after storage at 25° C. and 60% relative humidity (a room temperature experiment) for 1 month or 3 months. Specifications for these measures and results from representative batches of the 5 mg/ml and 20 mg/ml formulations are shown in Table 14A-E below. These results demonstrate that the formulations had excellent stability; the formulations continued to satisfy the specifications even after storage for 6 months at 2-8° C. and after storage at room temperature for 3 months.

TABLE 14A

EBI-005 Phase 1 GMP Drug Product (20 mg/mL, Batch X1) at 5 ± 3° C.

| Analysis | Specification | Release Data 0 Months | Stability Time Point Results | | | | | |
|---|---|---|---|---|---|---|---|---|
| | | | 1 Month | 2 Months* | 3 Months | 4 Months | 5 Months | 6 Months |
| Physio-Chemical Tests | | | | | | | | |
| Appearance | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates |
| pH | 6.2 to 6.8 | 6.5 | 6.6 | 6.6 | 6.6 | 6.6 | 6.5 | 6.3 |
| Osmolality | 270 to 370 mOsm/kg | 328 mOsm/kg | NS | NS | NS | NS | NS | NS |
| Content | | | | | | | | |
| Content by A280 | 20 ± 2.0 mg/mL | 18.3 mg/mL | 18.4 mg/mL | 18.2 mg/mL Superseded by 4 month | 18.4 mg/mL | 18.4 mg/mL | 18.7 mg/mL | 18.5 mg/mL |
| Identity | | | | | | | | |
| SDS-PAGE Non-Reduced | Main band conforms to reference standard | Main band conforms to reference standard | Main band conforms to reference standard | Main band conforms to reference standard | Main band conforms to reference standard | Main band conforms to reference standard | Main band conforms to reference standard | Main band conforms to reference standard |

TABLE 14A-continued

EBI-005 Phase 1 GMP Drug Product (20 mg/mL, Batch X1) at 5 ± 3° C.

| Analysis | Specification | Release Data 0 Months | Stability Time Point Results | | | | | |
|---|---|---|---|---|---|---|---|---|
| | | | 1 Month | 2 Months* | 3 Months | 4 Months | 5 Months | 6 Months |
| SDS-PAGE Reduced | Main band conforms to reference standard | Main band conforms to reference standard | Main band conforms to reference standard | Main band conforms to reference standard | Main band conforms to reference standard | Main band conforms to reference standard | Main band conforms to reference standard | Main band conforms to reference standard |
| | | | | Purity | | | | |
| SE-HPLC | >90% (a/a) Monomer | 99% (a/a) Monomer | 99% (a/a) Monomer | 100% (a/a) Monomer | 100% (a/a) Monomer | 100% (a/a) Monomer | 100% (a/a) Monomer | 100% (a/a) Monomer |
| RP-HPLC | ≥75% (a/a) Main Peak | 93% (a/a) Main Peak | 95% (a/a) Main Peak | 93% (a/a) Main Peak | 93% (a/a) Main Peak | 93% (a/a) Main Peak | 93% (a/a) Main Peak | 93% (a/a) Main Peak |
| WCEX-HPLC | ≥85% (a/a) Main Peak <10% (a/a) des-Ala-EBI-005 Meth Report Result Acet Report Result | 96% (a/a) Main Peak 4% (a/a) des-Ala-EBI-005 0.1% (a/a) Methionated 0.0% Acetylated | 95% (a/a) Main Peak 4% (a/a) des-Ala-EBI-005 0.1% (a/a) Methionated 0.0% Acetylated | 94% (a/a) Main Peak 5% (a/a) des-Ala-EBI-005 0.2% (a/a) Methionated 0.0% Acetylated | 94% (a/a) Main Peak 5% (a/a) des-Ala-EBI-005 0.2% (a/a) Methionated 0.0% Acetylated | 95% (a/a) Main Peak 4% (a/a) des-Ala-EBI-005 0.2% (a/a) Methionated 0.0% Acetylated | 95% (a/a) Main Peak 4% (a/a) des-Ala-EBI-005 0.2% (a/a) Methionated 0.0% Acetylated | 94% (a/a) Main Peak 4% (a/a) des-Ala-EBI-005 0.3% (a/a) Methionated 0.0% Acetylated |
| | | | | Activity | | | | |
| Potency Eleven QC-007 | $IC_{50}$ 50-200% of reference standard $IC_{50}$ | 82% | 93% | 107% | 94% | 92% | 173% (used 6 month data) | 173% |
| | | | | Sterility | | | | |
| Endotoxin | ≤5.6 EU/mL | <1 EU/mL | NS | NS | NS | NS | NS | NS |
| | | | | Integrity Testing | | | | |
| CIT | No Ingress of Dye | Pass | NS | NS | NS | NS | NS | NS |

NS = Not Sampled
*Optional time point at 12 months changed to a 2 month time point

TABLE 14B

EBI-005 Phase 1 GMP Drug Product (20 mg/mL, Batch X1) at 25° C./60% Relative Humidity

| Analysis | Specification | Stability Time Point Results | |
|---|---|---|---|
| | | 1 Month | 3 Months |
| Physio-Chemical Tests | | | |
| Appearance | Clear to slightly opalescent colorless solution essentially free from visible particulates | Clear to slightly opalescent colorless solution essentially free from visible particulates | Clear to slightly opalescent colorless solution essentially free from visible particulates |
| pH | 6.2 to 6.8 | 6.6 | 6.6 |
| Osmolality | 270 to 370 mOsm/kg | NS | NS |

TABLE 14B-continued

EBI-005 Phase 1 GMP Drug Product (20 mg/mL, Batch X1) at 25° C./60% Relative Humidity

| | | Stability Time Point Results | |
|---|---|---|---|
| Analysis | Specification | 1 Month | 3 Months |
| Content | | | |
| Content by A280 | 20 ± 2.0 mg/mL | 18.4 mg/mL | 19.5 mg/mL |
| Identity | | | |
| SDS-PAGE Non-Reduced | Main band conforms to reference standard | Main band conforms to reference standard | Main band conforms to reference standard |
| SDS-PAGE Reduced | Main band conforms to reference standard | Main band conforms to reference standard | Main band conforms to reference standard |
| Purity | | | |
| SE-HPLC | >90% (a/a) Monomer | 99% (a/a) Monomer | 99% (a/a) Monomer |
| RP-HPLC | ≥75% (a/a) Main Peak | 94% (a/a) Main Peak | 90% (a/a) Main Peak |
| WCEX-HPLC | ≥85% (a/a) Main Peak | 92% (a/a) Main Peak | 86% (a/a) Main Peak |
| | <10% (a/a) des-Ala-EBI-005 | 4% (a/a) des-Ala-EBI-005 | 4% (a/a) des-Ala-EBI-005 |
| | Meth Report Result | 0.1% (a/a) Methionated | 0.1% (a/a) Methionated |
| | Acet Report Result | 0.0% Acetylated | 0.0% Acetylated |
| Activity | | | |
| Potency Eleven QC-007 | $IC_{50}$ 50-200% of reference standard $IC_{50}$ | 100% | 94% |
| Sterility | | | |
| Endotoxin | ≤5.6 EU/mL | NS | NS |
| Integrity Testing | | | |
| CIT | No Ingress of Dye | NS | NS |

NS = Not Sampled

TABLE 14C

EBI-005 Phase 1 GMP Drug Product (20 mg/mL, Batch X2) at 5 ± 3° C.

| | | Release Data | Stability Time Point Results | | | |
|---|---|---|---|---|---|---|
| Analysis | Specification | 0 Months | 1 Month | 2 Months* | 3 Months | 4 Months |
| Appearance | Clear to slightly opalescent colorless solution essentially free from visible particulates | Clear to slightly opalescent colorless solution essentially free from visible particulates | NS | Clear to slightly opalescent colorless solution essentially free from visible particulates | NS | Clear to slightly opalescent colorless solution essentially free from visible particulates |
| pH | 6.2 to 6.8 | 6.6 | NS | 6.6 | NS | 6.4 |
| Osmolality | 270 to 370 mOsm/kg | 326 mOsm/kg | NS | NS | NS | NS |
| Content by A280 | 20 ± 2.0 mg/mL | 18.5 mg/mL | NS | 18.9 mg/mL | NS | 18.7 mg/mL |
| SDS-PAGE Non-Reduced | Main band conforms to reference standard | Main band conforms to reference standard | NS | Main band conforms to reference standard | NS | Main band conforms to reference standard |
| SDS-PAGE Reduced | Main band conforms to reference standard | Main band conforms to reference standard | NS | Main band conforms to reference standard | NS | Main band conforms to reference standard |
| SE-HPLC | >90% (a/a) Monomer | 100% (a/a) Monomer | NS | 100% (a/a) Monomer | NS | 100% (a/a) Monomer |
| RP-HPLC | ≥75% (a/a) Main Peak | 92% (a/a) Main Peak | 93% (a/a) Main Peak | 93% (a/a) Main Peak | 91% (a/a) Main Peak | 92% (a/a) Main Peak |

TABLE 14C-continued

EBI-005 Phase 1 GMP Drug Product (20 mg/mL, Batch X2) at 5 ± 3° C.

| Analysis | Specification | Release Data 0 Months | Stability Time Point Results | | | |
|---|---|---|---|---|---|---|
| | | | 1 Month | 2 Months* | 3 Months | 4 Months |
| WCEX-HPLC | ≥85% (a/a) Main Peak <10% (a/a) des-des-Ala-EBI-005 Meth Report Result Acet Report Result | 94% (a/a) Main Peak 4% (a/a) des-Ala-EBI-005 0.2% (a/a) Methionated 0.0% Acetylated | NS | 94% (a/a) Main Peak 4% (a/a) des-Ala-EBI-005 0.4% (a/a) Methionated 0.0% Acetylated | NS | 94% (a/a) Main Peak 4% (a/a) des-Ala-EBI-005 0.2% (a/a) Methionated 0.0% Acetylated |
| Potency Eleven QC-007 | IC$_{50}$ 50-200% of reference standard IC$_{50}$ | 83.0% | 100.0% (used 4 month data) | 100.0% (used 4 month data) | 100.0% (used 4 month data) | 100.0% |
| Endotoxin | ≤5.6 EU/mL | 0.3 EU/mL | NS | NS | NS | NS |
| CIT | No Ingress of Dye | Pass | NS | NS | NS | NS |

NS = Not Sampled
*Optional time point at 12 months changed to a 2 month time point

TABLE 14D

EBI-005 Phase 1 GMP Drug Product (5 mg/mL, Batch X3) at 5 ± 3° C.

| Analysis | Specification | Release Data 0 Months | Stability Time Point Results | | | | | |
|---|---|---|---|---|---|---|---|---|
| | | | 1 Month | 2 Months* | 3 Months | 4 Months | 5 Months | 6 Months |
| Physio-Chemical Tests | | | | | | | | |
| Appearance | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates | Clear to slightly opalescent colorless solution essentially free from visible particulates |
| pH | 6.2 to 6.8 | 6.5 | 6.6 | 6.5 | 6.5 | 6.6 | 6.4 | 6.3 |
| Osmolality | 270 to 370 mOsm/kg | 327 mOsm/kg | NS | NS | NS | NS | NS | NS |
| Content | | | | | | | | |
| Content by A280 | 5 ± 0.5 mg/mL | 4.7 mg/mL | 4.6 mg/mL | 4.6 mg/mL | 4.6 mg/mL Superseded by 4 month | 4.6 mg/mL | 4.7 mg/mL | 4.6 mg/mL |
| Identity | | | | | | | | |
| SDS-PAGE Non-Reduced | Main band conforms to reference standard | Main band conforms to reference standard | Main band conforms to reference standard | Main band conforms to reference standard | Main band conforms to reference standard | Main band conforms to reference standard | Main band conforms to reference standard | Main band conforms to reference standard |
| SDS-PAGE Reduced | Main band conforms to reference standard | Main band conforms to reference standard | Main band conforms to reference standard | Main band conforms to reference standard | Main band conforms to reference standard | Main band conforms to reference standard | Main band conforms to reference standard | Main band conforms to reference standard |
| Purity | | | | | | | | |
| SE-HPLC | >90% (a/a) Monomer | 99% (a/a) Monomer | 99% (a/a) Monomer | 100% (a/a) Monomer | 100% (a/a) Monomer | 100% (a/a) Monomer | 100% (a/a) Monomer | 100% (a/a) Monomer |

TABLE 14D-continued

EBI-005 Phase 1 GMP Drug Product (5 mg/mL, Batch X3) at 5 ± 3° C.

| Analysis | Specification | Release Data 0 Months | Stability Time Point Results | | | | | |
|---|---|---|---|---|---|---|---|---|
| | | | 1 Month | 2 Months* | 3 Months | 4 Months | 5 Months | 6 Months |
| RP-HPLC | ≥75% (a/a) Main Peak | 89.2% (a/a) Main Peak | 92% (a/a) Main Peak | 82% (a/a) Main Peak | 82% (a/a) Main Peak | 84% (a/a) Main Peak | 76% (a/a) Main Peak | 91% (a/a) Main Peak |
| WCEX-HPLC | ≥85% (a/a) Main Peak | 96% (a/a) Main Peak | 94% (a/a) Main Peak | 94% (a/a) Main Peak | 94% (a/a) Main Peak | 95% (a/a) Main Peak | 95% (a/a) Main Peak | 94% (a/a) Main Peak |
| | <10% (a/a) des-Ala-EBI-005 | 4% (a/a) des-Ala-EBI-005 | 5% (a/a) des-Ala-EBI-005 | 5% (a/a) des-Ala-EBI-005 | 5% (a/a) des-Ala-EBI-005 | 4% (a/a) des-Ala-EBI-005 | 4% (a/a) des-Ala-EBI-005 | 4% (a/a) des-Ala-EBI-005 |
| | Meth Report Result | 0.1% (a/a) Methionated | 0.2% (a/a) Methionated | 0.2% (a/a) Methionated | 0.2% (a/a) Methionated | 0.2% (a/a) Methionated | 0.3% (a/a) Methionated | 0.3% (a/a) Methionated |
| | Acet Report Result | 0.0% Acetylated | 0.0% Acetylated | 0.0% Acetylated | 0.0% Acetylated | 0.0% Acetylated | 0.0% Acetylated | 0.0% Acetylated |
| Activity | | | | | | | | |
| Potency | $IC_{50}$ 50-200% of reference standard $IC_{50}$ | 100% | 191% | 107% | 115% | 146% (used 6 month data) | 146% (used 6 month data) | 146% |
| Sterility | | | | | | | | |
| Endotoxin | ≤5.6 EU/mL | <1 EU/mL | NS | NS | NS | NS | NS | NS |
| Integrity Testing | | | | | | | | |
| CIT | No Ingress of Dye | Pass | NS | NS | NS | NS | NS | NS |

NS = Not Sampled
*Optional time point at 12 months changed to a 2 month time point

TABLE 14E

EBI-005 Phase 1 GMP Drug Product (5 mg/mL, X3) at 25° C./60% Relative Humidity

| | | Stability Time Point Results | |
|---|---|---|---|
| Analysis | Specification | 1 Month | 3 Months |
| Physio-Chemical Tests | | | |
| Appearance | Clear to slightly opalescent colorless solution essentially free from visible particulates | Clear to slightly opalescent colorless solution essentially free from visible particulates | Clear to slightly opalescent colorless solution essentially free from visible particulates |
| pH Fujifilm AM0001 | 6.2 to 6.8 | 6.6 | 6.5 |
| Osmolality | 270 to 370 mOsm/kg | NS | NS |
| Content | | | |
| Content by A280 | 5 ± 0.5 mg/mL | 4.6 mg/mL | 4.8 mg/mL |
| Identity | | | |
| SDS-PAGE Non-Reduced | Main band conforms to reference standard | Main band conforms to reference standard | Main band conforms to reference standard |
| SDS-PAGE Reduced | Main band conforms to reference standard | Main band conforms to reference standard | Main band conforms to reference standard |

TABLE 14E-continued

EBI-005 Phase 1 GMP Drug Product (5 mg/mL, X3) at 25° C./60% Relative Humidity

| Analysis | Specification | Stability Time Point Results | |
|---|---|---|---|
| | | 1 Month | 3 Months |
| Purity | | | |
| SE-HPLC | >90% (a/a) Monomer | 99% (a/a) Monomer | 100% (a/a) Monomer |
| RP-HPLC | ≥75% (a/a) Main Peak | 81% (a/a) Main Peak | 81% (a/a) Main Peak |
| WCEX-HPLC | ≥85% (a/a) Main Peak | 93% (a/a) Main Peak | 88% (a/a) Main Peak |
| | <10% (a/a) des-Ala-EBI-005 | 4% (a/a) des-Ala-EBI-005 | 4% (a/a) des-Ala-EBI-005 |
| | Meth Report Result | 0.2% (a/a) Methionated | 0.2% (a/a) Methionated |
| | Acet Report Result | 0.0% Acetylated | 0.0% Acetylated |
| Activity | | | |
| Potency | $IC_{50}$ 50-200% of reference standard $IC_{50}$ | 182% | 90% |
| Sterility | | | |
| Endotoxin | ≤5.6 EU/mL | NS | NS |
| Integrity Testing | | | |
| CIT | No Ingress of Dye | NS | NS |

NS = Not Sampled

Example 8: Melting Profiles

Figure 5A:
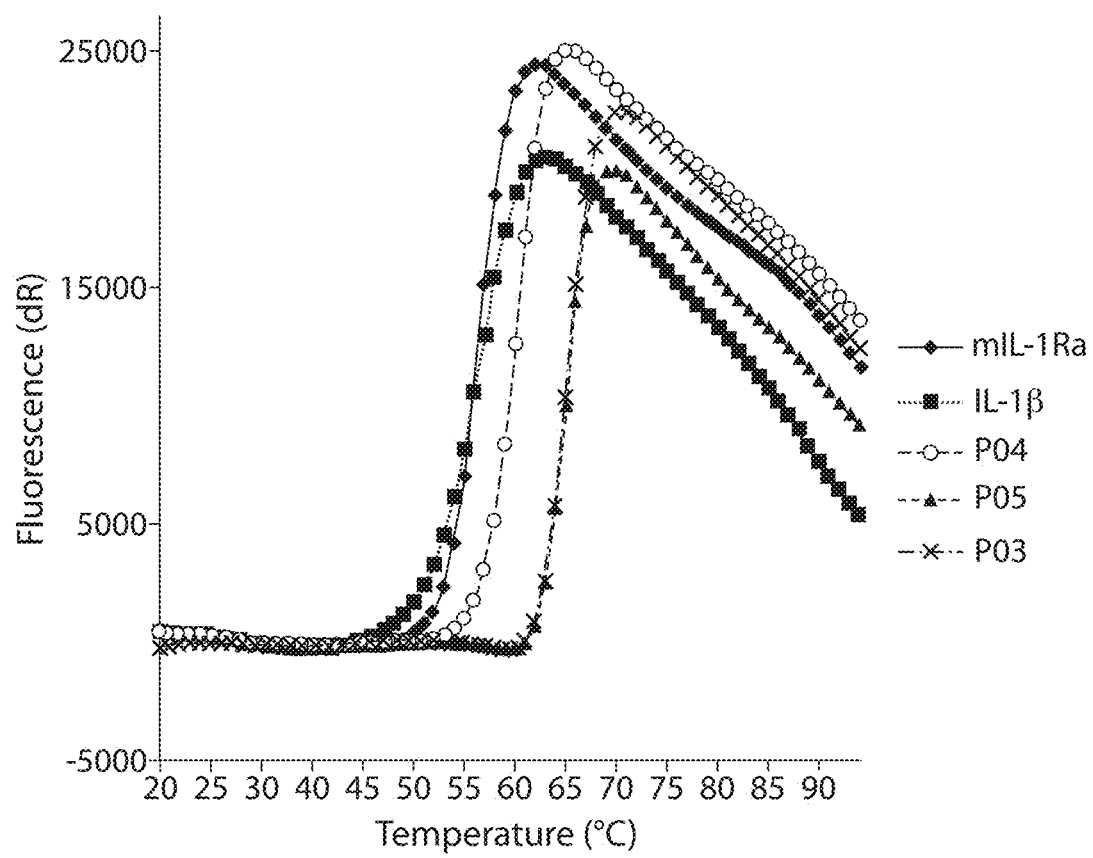
FIG. 5A is a graph depicting thermal denaturation of IL-1Ra, IL-1β, P03, P04, and P05 as described in Example 8.
Figure 5B:
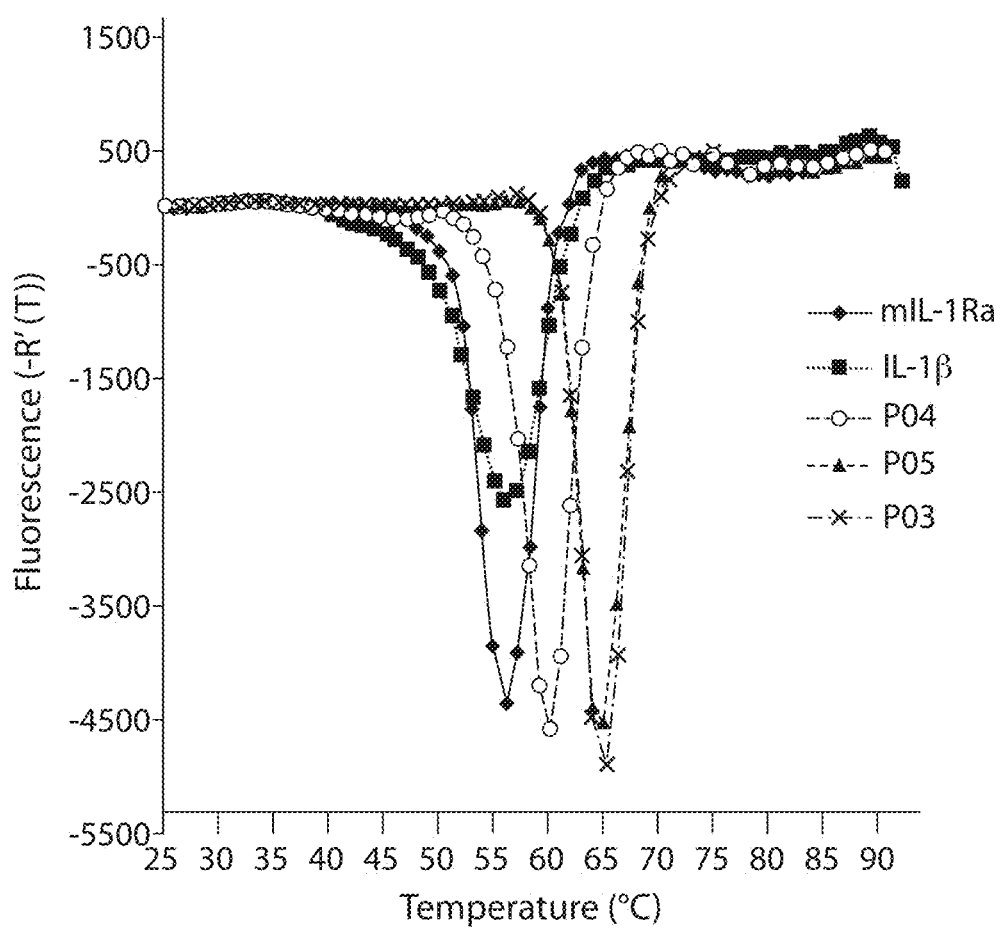
FIG. 5B is a graph depicting the negative first derivative of the graph in FIG. 5A (the negative first derivative provides improved visualization of the melting temperature).

Proteins P03, P04, P05, mIL-1Ra (methionyl IL-1Ra), and IL-1β were prepared in phosphate-buffered saline (PBS), pH 7.4, at 0.5 mg/ml. The proteins were combined with SYPRO® orange dye (Invitrogen, CA) at a 1:500 dilution of the stock concentration and subject to differential scanning fluorimetry. See, e.g., He et al. (2010) J Pharm Sciences, 99 1707-1720. Fluorescence measurements were monitored using an Agilent Mx3005 QPCR machine as the temperature was increased from 25° C. to 95° C. at a rate of 1° C. per minute. Melting temperature ($T_m$) values were derived from the maxima value of the first derivative of the fluorescence transition. The proteins P03, P04, and P05 were observed to have an onset of unfolding of greater than 50° C. and as high as 59° C., and $T_m$ of greater than 59, 60, 62, and 64° C. Results are shown in Table 4 below and FIG. 5A and FIG. 5B:

TABLE 4

| Protein | $T_m$ (° C.) | Onset of unfolding (° C.) |
|---|---|---|
| mIL-1Ra | 56 | 48 |
| IL-1β | 56 | 41 |
| P03 | 65 | 59 |
| P04 | 60 | 51 |
| P05 | 65 | 59 |

P04 has a $T_m$ that is about four degrees higher than mIL-1Ra and IL-1β and exhibits an onset of unfolding about three degrees higher than mIL-1Ra and about ten degrees higher than IL-1β. P03 and P05 have a $T_m$ that is about nine degrees higher than mIL-1Ra and IL-1β and exhibit an onset of unfolding about 11 degrees higher than mIL-1Ra and about 18 degrees higher than IL-1β. These data demonstrate methods of determining melting temperature an IL-1 inhibitor, e.g., in a formulation described herein.

Example 9: Treatment of Dry Eye in an Animal Model

Purified P05 (lacking a hexa-histidine tag (SEQ ID NO:23)) was prepared in 1.25×PBS and tested in a murine model of dry eye disease. In this model, female C57BL/6 mice 6 to 10 weeks of age from Jackson Laboratories (acclimated for 1 to 2 weeks in an animal holding room with ≥30% relative humidity, hydrogel food supplement, and Enviro-dri™ environment enrichment) were pre-screened for fluorescein staining on Day 0. For fluorescein staining, freshly made fluorescein diluted in WFI $H_2O$ at 10 mg/mL was administered at 0.4 μL to each eye. Approximately 8-13 minutes after administration, eyes were scored using an Olympus fluorescent dissecting microscope. Punctuate staining was recorded using the standardized National Eye Institute (NEI) grading system of 0-3 for each of the five areas into which the corneal surface has been divided (score range 0-15/eye). Using a teaching bridge, two masked scorers evaluated mice at the same time to give a single collective score for each eye.

Mice with scores ≤7 for each eye (out of a maximal score of 15) were placed in a dry eye chamber (20%±2% humidity and constant air flow ~21 L/min/cage) on day 1 and were maintained in this chamber during the course of the experiment (except for examination). On day 3, mice were scored again and randomized into treatment groups with 8 to 10 mice/group. Mice were randomized such that each cage of 4 to 5 mice had approximately the same mean disease score. Beginning on day 3 and after randomization, mice were topically administered P05 or vehicle (1.25×PBS) in an eye drop at 3 μL/eye BID. Mice were examined and scored on days 7, 9, and 11 for corneal fluorescein staining as described above. Scorers were blinded as to the treatment groups during the course of the experiment.

Figure 6A:
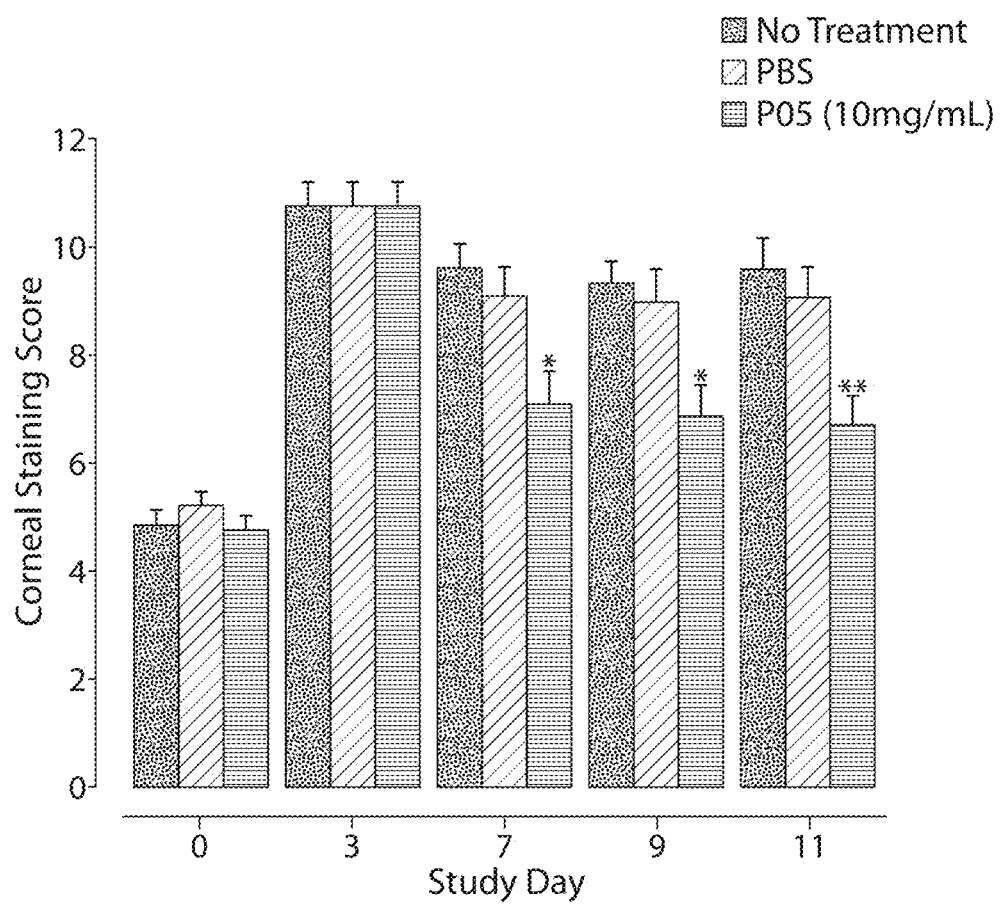
FIG. 6A is a bar graph depicting the mean corneal staining score±SEM as tested by fluorescein staining of the cornea per eye of two independent studies, on days 0, 3, 7, 9, and 11 for mice in a dry eye model. The mice received no treatment (n=18), 10 mg/ml P05 (n=19), or 1.25×PBS, the vehicle (n=20). Asterisks indicate statistical significance of P05 relative to vehicle as follows: * ($P<0.05$) and ** ($P<0.005$).

FIG. 6A is a bar graph of mean corneal staining score±SEM at day 0, 3, 7, 9, and 11 for mice from two identical experiments under the following bid treatments: no treatment, vehicle (1.25×PBS), and 10 mg/ml (1%) P05. 10 mg/ml P05 significantly reduced corneal staining on days 7, 9, and 11 of the experiment. Efficacy as evaluated by a reduction in corneal staining was also observed with doses as low as 0.1 mg/ml P05. Recombinant IL-1Ra produced in E. coli also moderately reduced corneal staining in the animal model.

Figure 6B:
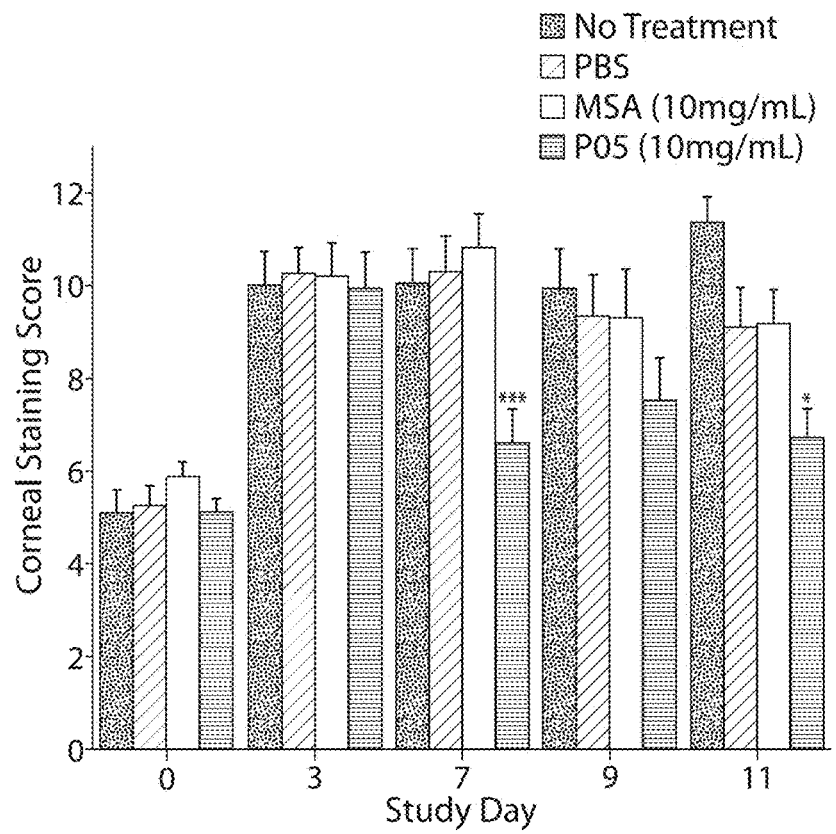
FIG. 6B is a bar graph representing data showing mean corneal staining score±SEM of the cornea per eye, on days 0, 3, 7, 9, and 11 for mice in a dry eye model. The mice received no treatment (n=8), 1.25×PBS vehicle (n=8), 10 mg/ml murine serum albumin (MSA) (n=8), or 10 mg/ml P05 (n=9). Asterisks indicate statistical significance of P05 relative to murine serum albumin as follows: * ($P<0.05$) and *** ($P<0.0005$).
Figure 6C:
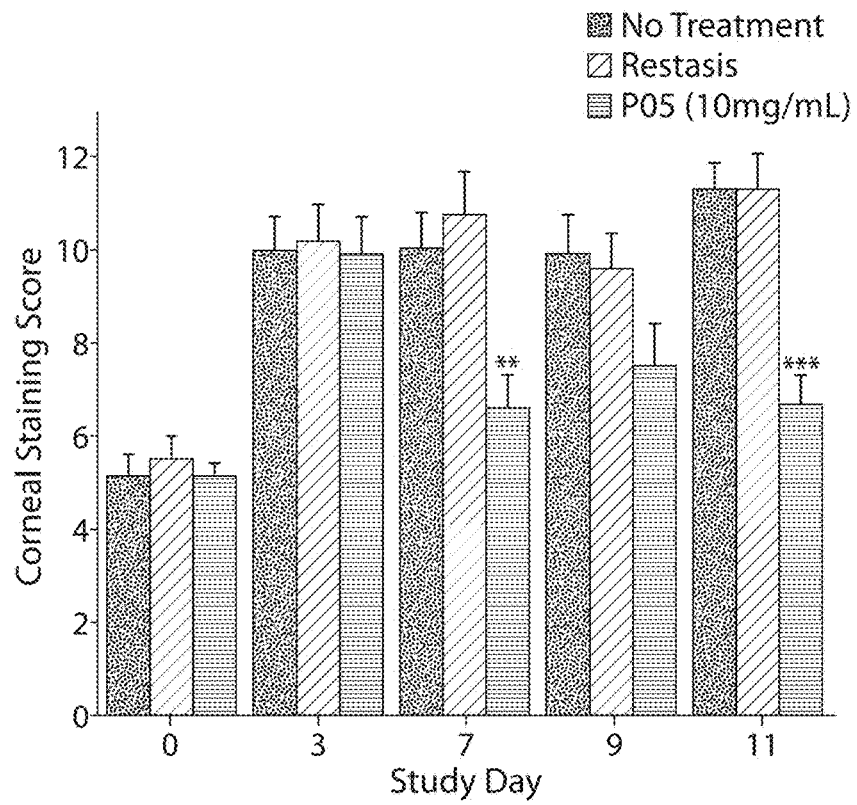
FIG. 6C is a bar graph representing data for mice that were treated with Restasis® (0.05% cyclosporine emulsion) (n=8) in the same experiment as FIG. 6B. Asterisks indicate statistical significance of P05 relative to cyclosporine (Restasis®) as follows:  ($P<0.005$) and * ($P<0.0005$).
Figure 10:
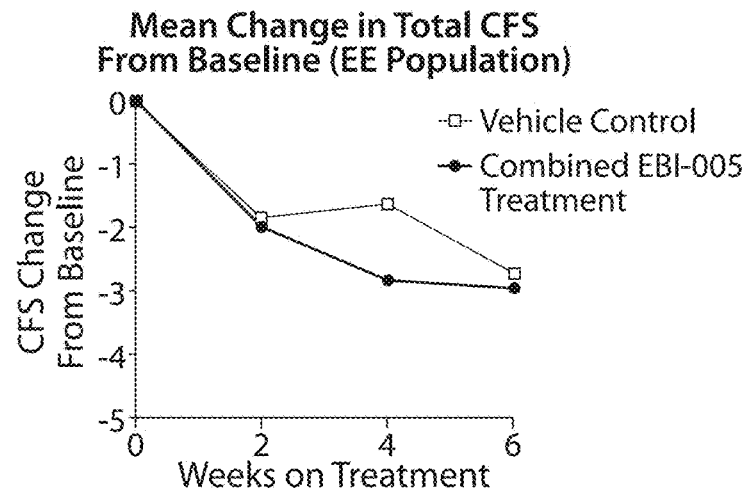
FIG. 10 is a graph showing the mean change from baseline in corneal fluorescein staining (CFS) score for the groups of subjects who received EBI-005 formulations (combined data for the groups that received 5 mg/ml and 20 mg/ml treatments) and vehicle formulation.

As shown in FIG. 6B, the effect of 10 mg/ml P05 was specific based on a comparison to 10 mg/ml murine serum albumin in the same vehicle. No effect was seen with 10 mg/ml murine serum albumin (MSA) relative to vehicle, and the effect of 10 mg/ml P05 was statistically significant relative to 10 mg/ml murine serum albumin. As shown in FIG. 6C, 10 mg/ml P05 was also compared to 0.05% cyclosporine in an ophthalmic emulsion (Restasis®). Whereas P05 reduced corneal staining, no effect was observed for the 0.05% cyclosporine ophthalmic emulsion after about 1 week of b.i.d. dosing. These experiments demonstrate methods of testing efficacy of an IL-1 inhibitor in a formulation described herein.

Example 10: Agitation Studies

To identify a surfactant suitable for use, P05 at 1 mg/ml and at 50 mg/ml was prepared in solutions of either (i) PBS, 0.5% w/v CMC, pH 7.4 or (ii) 10 mM sodium citrate, pH 6.0 containing various surfactants. Agitation was performed by vortexing the protein at room temperature for four hours. The samples were analyzed by micro-fluid imaging (MGI), SEC, $A_{280}$, and visual inspection. It was found that the use of 0.1% w/v poloxamer 188, compared with other surfactants (including, e.g., polysorbate 20, polysorbate 80, or no surfactant) protected the protein from precipitation (assessed using visual inspection) and significant subvisible particle accumulation during agitation. For example, the 0.1% w/v poloxamer reduced particle counts for particles ≥10 microns and for particles ≥25 microns.

This result demonstrates that poloxamer 188 is a suitable surfactant for formulating a polypeptide such as P05. Furthermore, it demonstrates that as little as 0.1% w/v surfactant can be effective for limiting and even decreasing the amount of precipitation. These experiments also demonstrate a method of determining the suitability of a formulation described herein.

Example 11: Preparation of a Formulation

Formulations of P05 were prepared. In brief, P05 was provided as a frozen liquid containing 52.8 mg/mL P05 in 1×PBS, pH 6.5. The polypeptide was dialyzed against a buffer containing 10 mM sodium citrate and 5% w/v sorbitol at pH 6.0 using 3500 molecular weight cutoff dialysis cassettes in an approximately 10,000-fold exchange over about 24 hours at 2-8° C. Following dialysis, the concentration was determined by measuring A280/A320.

After dialysis, formulations were prepared with various concentrations of P05 as follows, 100× poloxamer 188 surfactant was added to a 1× concentration to a stock solution of dialyzed P05. The protein concentrations were adjusted to approximately 1 mg/mL, 5 mg/mL and 20 mg/mL by adding formulation buffer (10 mM Na citrate, 5% w/v sorbitol, pH 6.0). The final concentration of the formulation components was about 10 mM sodium citrate, 5% w/v sorbitol, and 0.1% w/v poloxamer 188. Samples were then mixed and sterile filtered under aseptic conditions then were filled (at 250 μL) into 2 cc glass vials under aseptic conditions. After preparation, samples were placed in stability studies to confirm stability of the formulation prepared under the foregoing conditions.

This demonstrates a method of preparing an IL-1 inhibitor, e.g., an IL-1beta/IL-1Ra chimeric protein formulation.

Example 12: Stability of P05 in Phosphate Versus Citrate Buffer

Dynamic light scattering or DLS (also known as quasi elastic light scattering or QELS) measures the diffusion of an analyte (e.g., P05) in a well plate by focusing laser light on the sample, and monitoring the rate of fluctuation of the scattered light as measured by a fast photon counter. A mathematical technique, known as a correlation function, is used to quantify the rate of fluctuation to determine the diffusion coefficient. The diffusion coefficient is used to obtain radius of hydration (Rh) by the Stokes-Einstein equation.

The radius of P05 was measured as a function of increasing temperature in a DLS plate reader (Wyatt DynaPro™, Wyatt Technologies, Santa Barbara, Calif.). The acquisition time was 5 seconds and 5 scans were performed for each measurement. The ramp rate was 0.17° C./min. As the protein unfolded, the radius increased. The temperature at which the radius increased is referred as $T_{on}$ (temperature of onset for unfolding).

Figure 4A:
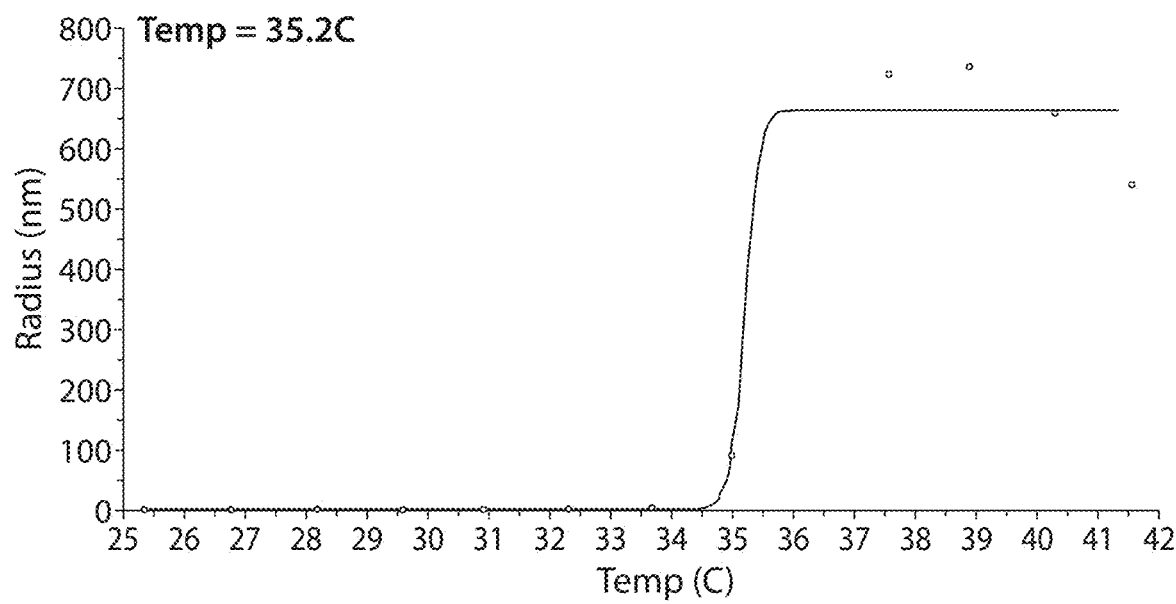
FIG. 4A is a graph showing the dynamic light scattering (DLS) results for P05 in a phosphate formulation (P05 at 20 mg/ml, 10 mM phosphate, 5% w/v sorbitol, 0.1% w/v poloxamer 188, pH 6.5).
Figure 4B:
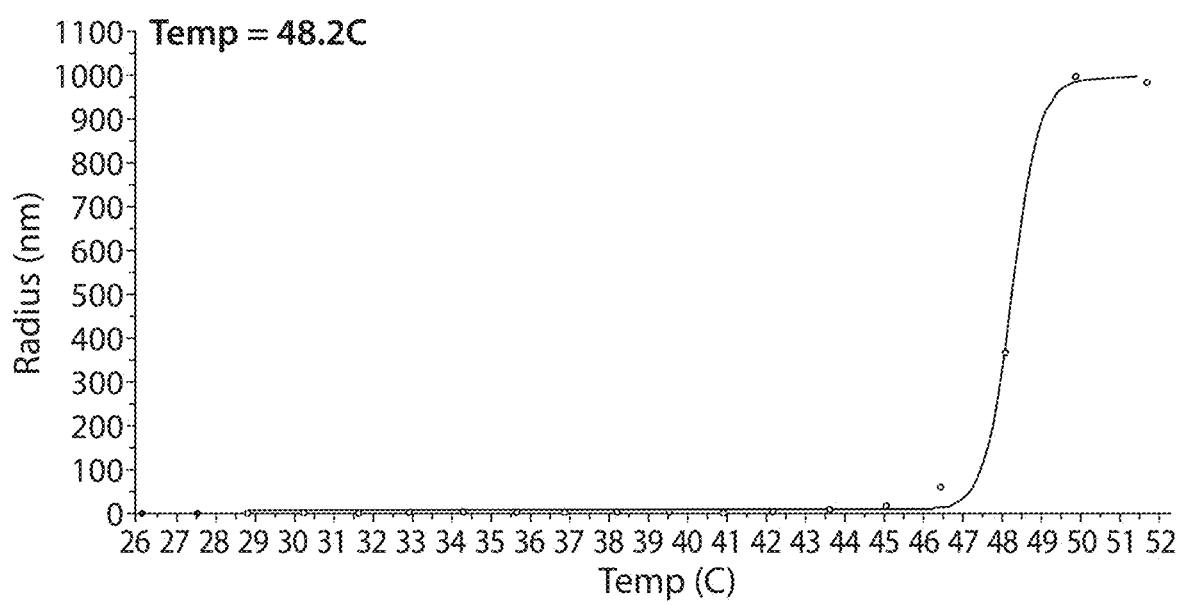
FIG. 4B is a graph showing DLS results for P05 in a citrate formulation (P05 at 20 mg/ml, 10 mM citrate, 5% w/v sorbitol, 0.1% w/v poloxamer 188, pH 6.0).

This experiment was performed for P05 at 20 mg/mL in two formulations: (i) 10 mM phosphate, 5% w/v sorbitol, 0.1% w/v poloxamer 188, pH 6.5 and (ii) 10 mM sodium citrate, 5% w/v sorbitol, 0.1% w/v poloxamer 188, pH 6.0. The results, depicted in FIG. 4A and FIG. 4B, showed that the $T_{on}$ occurred at a much higher temperature in the citrate buffer relative to phosphate buffer. The $T_{on}$ was 48.2° C. for P05 in citrate buffer, and 35.2° C. for P05 in phosphate buffer. This large difference in $T_{on}$ was surprising and indicated that P05 is much more stable in the citrate buffer compared with phosphate buffer. Accordingly, in some embodiments a formulation comprising an IL-1 inhibitor, e.g., P05, contains citrate buffer.

Example 13: Stability Studies

To test the stability of formulations described in Example 11, formulations with various concentrations of P05 were prepared (as described in Example 11, supra) and were analyzed for baseline measurements. Vials of the formulated polypeptide were incubated at 25° C. for 0 days, 3 days, 1 week, 2 weeks, and 4 weeks and at 40° C. for 3 days, 1 week, and 2 weeks. At least 2 vials were prepared per time point. Following incubation, the samples were analyzed using size exclusion HPLC (SE-HPLC), weak cation exchange HPLC (WCX-HPLC), reversed phase HPLC (RP-HPLC), concentration (A280-A320), visual appearance, formal inspection performed with photographs. The pH was analyzed at T=0 and T=4 weeks. Osmolality was analyzed only at T=0. Visual inspection and concentration were evaluated at 2 weeks and 4 weeks at both 25° C. and 40° C. All formulations were clear and colorless without visible particles after 2 weeks. The 25° C. samples were clear and colorless after 4 weeks. The results for these concentration studies are illustrated in Table 5.

TABLE 5

| Sample | Initial concentration (T = 0) mg/ml | Osmolality at T = 0 | Concentration @ T = 25° C. | | Concentration @ T = 40° C. | |
|---|---|---|---|---|---|---|
| | | | 2 weeks | 4 weeks | 2 weeks | 4 weeks |
| C1 | 1.08 | 306 mOsm/kg | 1.04 | 1.04 | 1.04 | NA |
| C2 | 5.27 | 305 mOsm/kg | 5.25 | 5.23 | 5.20 | NA |
| C3 | 21.0 | 315 mOsm/kg | 21.2 | 21.0 | 21.2 | NA |

The pH of the 25° C. samples was determined at 4 weeks. In all cases, the pH at T=0 was 6.00-6.01 and the pH at 4 weeks was 6.03-6.07. These data demonstrate stability of the formulations across a range of concentrations in the formulations at 25° C. for at least 4 weeks and at 40° C. for at least 2 weeks.

SEC-HPLC

Purity was assessed using a size exclusion HPLC method using absorbance and fluorescence detection. Briefly, Sepax Zenix® SEC-150 7.8 mm×20 cm (PN 213150-7820) columns were used. The mobile phase was ix PBS. Evaluations were performed using an Agilent 1100 HPLC system in isocratic mode with a flow rate of 1 mL/minute, a total run time of 18 minutes, at ambient temperature. Absorbance detection was at 280 nm with fluorescence detection at an excitation wavelength of 280 nm and emission detection wavelength of 350 nm. For experiments employing fluorescence detection of 1 and 5 mg/ml samples, 10 µg of polypeptide formulation was loaded and for absorbance detection of 20 mg/ml samples, 50 µg of polypeptide formulation was loaded.

After 2 weeks of storage, the reference standard for the 1 mg/ml and 5 mg/ml P05 formulations had an assayed purity of 99.1% and the purity of 1 mg/ml and 5 mg/ml samples of the P05 formulation were 99.1%-99.2%, respectively, regardless of whether they were stored at 25° C. or 40° C. For the 20 mg/ml sample, the reference had a purity of 99.2%. After two weeks of storage, the 20 mg/ml samples had a purity of 99.2%, regardless of whether they were stored at 25° C. or 40° C. After 4 weeks of storage at 25° C., the 20 mg/ml P05 formulation had a purity of 99.2%.

wCEX-HPLC

In additional studies, a weak cation exchange HPLC method was used to assess the formulations. In this method, a Dionex ProPac® WCX-10, 4×250 mm (PN 054993) column was used. Mobile phase A was 10 mM Na acetate, pH 5.5 and mobile phase B was mobile A+0.25 M NaCl. The assay was performed using an Agilent 1100 HPLC system with a flow rate of 1.2 mL/minute and a total run time of 35 minutes at ambient temperature. Detection was performed by assaying at 214 nm and 280 nm. Sample size was 25 µg/injection. A summary of the results after storage for 2 weeks at 25° C. is shown in Table 6, after storage for 2 weeks at 40° C. in Table 7, and after storage for 4 weeks at 25° C. in Table 8.

The weak cation exchange assay is another method of assessing purity by monitoring charge heterogeneity. Analysis of P05 formulation samples resolves the main product peak from several product related impurities based on charge. A typical preparation of P05 consists of approximately >85% main peak and several pre- and post-peaks. Pre-peak 1 is unknown, Pre-peak 2 is a form of deamidated P05, Pre-peak 3 is a form of P05 with an N-terminal methionine. Post-peak 1 is a form of P05 missing the N-terminal alanine, Post-peak-2 is a form of P05 missing both the N-terminal alanine and proline, Post-peak 3 is unknown.

TABLE 6

25° C. Storage/2 weeks

| Form # | Formulation | % Pre-Peak 1 | % Pre-Peak 2 | % Pre-Peak 3 | % Main Peak | % Post-Peak 1 | % Post-Peak 2 | % Post-Peak 3 | Total Area |
|---|---|---|---|---|---|---|---|---|---|
| — | Ref. Std. | 0.0 | 1.0 | 1.3 | 91.5 | 5.5 | 0.3 | 0.3 | 1200 |
| C1 | 01C6.0SP | 0.0 | 1.4 | 1.3 | 90.3 | 6.1 | 0.4 | 0.4 | 1166 |
| C2 | 05C6.0SP | 0.0 | 1.1 | 1.1 | 91.5 | 5.6 | 0.4 | 0.4 | 1176 |
| C3 | 20C6.0SP | 0.0 | 1.5 | 1.3 | 90.8 | 5.4 | 0.5 | 0.5 | 1255 |

TABLE 7

40° C. Storage/2 weeks

| Form # | Formulation | % Pre-Peak 1 | % Pre-Peak 2 | % Pre-Peak 3 | % Main Peak | % Post-Peak 1 | % Post-Peak 2 | % Post-Peak 3 | Total Area |
|---|---|---|---|---|---|---|---|---|---|
| — | Ref. Std. | 0.0 | 1.1 | 1.4 | 91.4 | 5.5 | 0.4 | 0.2 | 1220 |
| C1 | 01C6.0SP | 0.0 | 1.9 | 1.3 | 89.4 | 6.5 | 0.6 | 0.3 | 1151 |
| C2 | 05C6.0SP | 0.0 | 1.8 | 1.4 | 89.3 | 6.5 | 0.7 | 0.3 | 1181 |
| C3 | 20C6.0SP | 0.0 | 2.0 | 1.4 | 89.5 | 6.1 | 0.7 | 0.3 | 1223 |

TABLE 8

25° C. Storage/4 weeks

| Form # | Formulation | % Pre-Peak 1 | % Pre-Peak 2 | % Pre-Peak 3 | % Main Peak | % Post-Peak 1 | % Post-Peak 2 | % Post-Peak 3 | Total Area |
|---|---|---|---|---|---|---|---|---|---|
| — | Ref. Std. | 0.0 | 1.1 | 1.4 | 91.4 | 5.5 | 0.4 | 0.2 | 1220 |
| C1 | 01C6.0SP | 0.0 | 1.9 | 1.3 | 89.4 | 6.5 | 0.6 | 0.3 | 1151 |
| C2 | 05C6.0SP | 0.0 | 1.8 | 1.4 | 89.3 | 6.5 | 0.7 | 0.3 | 1181 |
| C3 | 20C6.0SP | 0.0 | 2.0 | 1.4 | 89.5 | 6.1 | 0.7 | 0.3 | 1223 |

After 2 weeks of storage at 25° C., the percent main peak remained similar to the reference for the 5 mg/ml formulation (C2), about 91% purity, whereas there was a slight decrease in purity for C3 (20 mg/ml) and C1 (1 mg/ml) as determined using this method. Decreases in the main peak and increases in pre-peak 2, post-peak 1, and post-peak 2 were observed for all samples following storage at 40° C. After storage for four weeks, decreases were observed in the main peak purity and there was an increase in pre-peak 2 and post-peak 1.

Reversed Phase HPLC (RP-HPLC)

Formulations were also assessed using RP-HPLC. The RP-HPLC assay is another method of assessing purity by monitoring product heterogeneity based on hydrophobicity. The method is capable of separating the native molecule from product related impurities that contain oxidized methionines. Pre-peaks 2 and 3 are oxidized forms of the P05, and post-peaks 1 and 2 are acetylated forms of the molecule.

In this method, a Waters Symmetry® C4 (4.6×150 mm; 3.5 μm; PN 186000283) was used with a mobile phase A of 0.05% trifluoroacetic acid (TFA) in water and mobile phase B was 0.05% TFA in 95% acetonitrile (ACN). Assays were run using an Agilent 1200 HPLC system with a flow rate of 1 mL/minute for a total run time of 35 minutes and a column temperature of 55° C. Detection was performed at 280 nm. The amount of sample loaded for 1 mg/ml and 5 mg/ml samples was 25 μg and the amount of sample loaded was 50 μg. A summary of the results after storage for 2 weeks at 25° C. is shown in Table 9, after storage for 2 weeks at 40° C. in Table 10, and after storage at 4 weeks at 25° C. in Table 11 for the 1 mg/ml and 5 mg/ml formulations. Data for the 20 mg/ml formulation after two weeks of storage and 25° C. and 40° C. are shown in Tables 12 and 13, respectively.

TABLE 9

25° C. Storage for 2 Weeks

| Form. # | Formulation | % Pre-Peak 1 | % Pre-Peak 2 | % Pre-Peak 3 | % Pre-Peak 4 | % Main Peak | % Post-Peak 1 | % Post-Peak 2 | Total Area |
|---|---|---|---|---|---|---|---|---|---|
| t = 2 week Ref. Std. | | 0.0 | 0.2 | 1.3 | 0.2 | 96.8 | 1.1 | 0.4 | 1650 |
| C1 | 01C6.0SP | 0.0 | 0.3 | 4.5 | 0.4 | 93.1 | 1.3 | 0.5 | 1602 |
| C2 | 05C6.0SP | 0.0 | 0.2 | 2.6 | 0.3 | 95.1 | 1.3 | 0.4 | 1602 |

TABLE 10

40° C. Storage for 2 Weeks, 1 mg/ml and 5 mg/ml Formulations

| Form. # | Formulation | % Pre-Peak 1 | % Pre-Peak 2 | % Pre-Peak 3 | % Pre-Peak 4 | % Main Peak | % Post-Peak 1 | % Post-Peak 2 | Total Area |
|---|---|---|---|---|---|---|---|---|---|
| t = 2 week Ref. Std. | | 0.0 | 0.2 | 1.3 | 0.2 | 96.8 | 1.1 | 0.4 | 1650 |
| C1 | 01C6.0SP | 0.0 | 0.3 | 8.2 | 1.3 | 87.9 | 1.9 | 0.4 | 1571 |
| C2 | 05C6.0SP | 0.0 | 0.2 | 4.1 | 1.2 | 92.3 | 1.8 | 0.4 | 1591 |

TABLE 11

25° C. Storage for 4 Weeks, 1 mg/ml and 5 mg/ml Formulations

| Form. # | Formulation | % Pre-Peak 1 | % Pre-Peak 2 | % Pre-Peak 3 | % Pre-Peak 4 | % Main Peak | % Post-Peak 1 | % Post-Peak 2 | Total Area |
|---|---|---|---|---|---|---|---|---|---|
| t = 4 weeks Ref. Std. | | 0.0 | 0.2 | 1.3 | 0.3 | 96.8 | 1.0 | 0.4 | 1648 |
| C1 | 01C6.0SP | 0.0 | 0.3 | 5.5 | 0.6 | 91.9 | 1.4 | 0.4 | 1583 |
| C2 | 05C6.0SP | 0.0 | 0.2 | 3.0 | 0.6 | 94.5 | 1.4 | 0.3 | 1598 |

TABLE 12

25° C. Storage for 2 Weeks, 20 mg/ml Formulation

| Form. # | Formulation | % Pre-Peak 1 | % Pre-Peak 2 | % Pre-Peak 3 | % Pre-Peak 4 | % Main Peak | % Post-Peak 1 | % Post-Peak 2 | Total Area |
|---|---|---|---|---|---|---|---|---|---|
| t = 2 week Ref. Std. | | 0.0 | 0.2 | 1.3 | 0.2 | 96.8 | 1.1 | 0.4 | 3297 |
| C3 | 20C6.0SP | 0.0 | 0.2 | 2.0 | 0.3 | 96.1 | 1.1 | 0.4 | 3340 |

TABLE 13

40° Storage for 2 Weeks, 20 mg/ml Formulation

| Form. # | Formulation | % Pre-Peak 1 | % Pre-Peak 2 | % Pre-Peak 3 | % Pre-Peak 4 | % Main Peak | % Post-Peak 1 | % Post-Peak 2 | Total Area |
|---|---|---|---|---|---|---|---|---|---|
| t = 2 week | Ref. Std. | 0.0 | 0.2 | 1.3 | 0.2 | 96.8 | 1.1 | 0.4 | 3297 |
| C3 | 20C6.0SP | 0.0 | 0.2 | 3.3 | 0.7 | 94.1 | 1.4 | 0.4 | 3270 |

After two weeks of storage at 25° C. or 40° C., a decrease in the main peak purity was observed and an increase in pre-peak 3 (oxidized P05) was observed for the 1 mg/ml and 5 mg/ml formulations. This effect was most prominent for the 1 mg/ml sample (C1) at high temperature. After four weeks of storage at 25° C., a decrease in main peak purity and an increase in pre-peak 3 (oxidized P05) was observed for these formulations and this effect was most prominent for the 1 mg/ml sample. Interestingly, after two weeks of storage at 25° C., the 20 mg/ml formulation had a main peak percentage similar to T=0 (96.1% purity). A decrease in the percent main peak and increase in pre-peak 3 (oxidized P05) was observed for this sample after two weeks of storage at 40° C. After four weeks of storage at 25° C., the 20 mg/ml formulation showed a slight decrease in main peak purity and an increase in pre-peak 3 (oxidized P05).

These analytical data demonstrate methods of analyzing the stability of a chimeric cytokine formulation and in particular demonstrate the surprising stability of a chimeric cytokine preparation comprising the P05 polypeptide. Accordingly, in some embodiments, the invention relates to a formulation stored for at least 2 weeks, e.g., at least 4 weeks at 25° C., e.g., 40° C. at a concentration of at least 1 mg/ml, at least 5 mg/ml, or at least 20 mg/ml and has a purity of at least 92%, e.g., at least 94%, or at least 96%.

Example 14: Stability of Formulations in Blow Fill Seal Containers

The process of packaging formulations into blow fill seal (BFS) containers involves plastic extrusion, molding, aseptic filling, and sealing in sequence. See, e.g., Liu, W. et al. 2011 Biopharm International, 24(7): 22-29. In the extrusion step, plastic granules are melted at temperatures above 160° C. Subsequently, the plastic is molded into the desired container shape, filled with formulation solution, and hermetically sealed.

Because the plastic materials used to form the containers are gas permeable to some degree, the stability of the formulation may suffer during long term storage (e.g., due to evaporation of water from the container and/or protein oxidation). Sealing such containers in an aluminum foil pouch or other suitable package may protect the formulation from light-induced degradation. Sealing the containers in such aluminum foil pouches with an inert gas, e.g., nitrogen or argon can protect against oxidation. Accordingly, experiments were conducted to investigate the effects of packaging and subsequent storage of P05 in blow fill seal (BFS) containers, with or without aluminum foil pouches with an inert gas overlay.

Testing was performed for formulations containing active pharmaceutical, P05. Bulk drug substance was formulated into an aqueous solution containing 10 mM sodium citrate, 5% w/v sorbitol, 0.1% w/v poloxamer 188, at pH 6.0 for blow fill processing. The target concentration for P05 was 5.0 mg/mL.

The formulation was cooled to about 2° C.-8° C. and filled into containers. Approximately 1000 containers were filled and the target fill volume of the containers was 0.32 mL. A portion of the containers were pouched in foil packages with a nitrogen overlay. An initial characterization was performed following the packaging into BFS containers and further stability evaluations were conducted following storage at two temperatures (2° C. to 8° C. and 25° C.), with or without pouching.

The initial characterization analysis included: concentration by $A_{280}$, SDS-PAGE, SEC-HPLC, wCEX-HPLC, RP-HPLC, osmolality and particle analysis by light obscuration. The stability of P05 was monitored monthly by SEC-HPLC, wCEX-HPLC and RP-HPLC, with $A_{280}$ evaluation performed at months 4 and 5, and pH and osmolality at month 5.

Initial Characterization of P05 Formulation Following Blow Fill Processing Showed Retention of Stability Initial analyses of P05 following blow fill processing demonstrated that the protein retained its chemical and physical stability despite the blow fill processing. The results from a P05 formulation not exposed to the BFS process (aqueous formulation containing P05 at a concentration of 50 mg/mL, 0.01% w/v poloxamer 188, 5% w/v sorbitol, 10 mM sodium phosphate, at pH 6.5) were compared with a P05 formulation that was subjected to the blow fill process (aqueous formulation containing P05 at a concentration of 5 mg/mL, 0.1% w/v poloxamer 188; 5% w/v sorbitol; 10 mM sodium citrate, at pH 6.0). These formulations were made with P05 from the same production batch.

The results show that at time zero following the blow fill packaging, the blow filled formulation retained excellent stability even after exposure to the potentially detrimental blow fill process, as indicated by analyses using size exclusion chromatography, RP-HPLC, wCEX, and SDS-PAGE (see Table 15).

TABLE 15

Comparison of Stabilities

| Analysis | P05 formulation not exposed to BFS process | P05 formulation after packaging in BFS container |
|---|---|---|
| Size Exclusion | 99% main peak | 100% main peak |
| RP-HPLC | 97% main peak | 97.6% main peak |
| wCEX | 94% main peak | 95.3% main peak |
| | 5% des-ala | 4.2% des-ala + methionine species unresolved from main peak |
| | 0.2% + methionine species | |
| SDS-PAGE | Conforms to reference | Conforms to reference |

*Measurements were averaged from three vials (pulled randomly) from the latter half of the fill/finish In addition to the above assays, particle analysis was performed on the formulation packaged in BFS containers, using light obscuration according to method USP <789>. The subvisible particle counts were within the USP specifications for topical ophthalmics (having less than or equal to 50 particles per ml for particles ≥10 μm and less than or equal to 5 particles per ml for particles ≥25 μm), consistent with the lack of visible precipitation in the BFS containers (data not shown).

These data demonstrate that P05 was both physically stable (according to measurements from SEC-HPLC, light obscuration, and visible observation) and chemically stable (according to measurements from wCEX-HPLC, RP-HPLC, SDS-PAGE) immediately following blow fill processing.

As part of the initial characterization, osmolality and concentration by $A_{280}$ were measured. The average osmolality measurement was 317 mOsm, and the average concentration by $A_{280}$ was 5.0 mg/mL.

P05 Formulation Stored in Blow Fill Containers Retained Stability

The P05 formulation in BFS containers was stored in an incubator at 25° C. with 60% relative humidity or at 2 to 8° C. At monthly intervals, samples were analyzed by SEC, RP-HPLC, and wCEX-HPLC. At months 4 and 5, concentration was measured by $A_{280}$. At month 5, osmolality (to assess evaporation), pH and concentration by $A_{280}$ were also measured.

TABLE 16

SEC-HPLC Stability Results (% Main Peak) for
P05 formulation Stored in BFS containers

| Month | 25° C./60% RH | | 2 to 8° C. | |
|---|---|---|---|---|
| | Pouched | Not Pouched | Pouched | Not Pouched |
| 0 | 100 | 100 | 100 | 100 |
| 2 | 99.0 | 99.0 | 99.2 | 99.3 |
| 3 | 99.7 | 99.8 | 99.8 | 99.8 |
| 4 | 99.3 | 99.4 | 99.5 | 99.5 |
| 5 | 99.6 | 99.7 | 99.8 | 99.9 |

The SEC-HPLC results (see Table 16) indicate that the P05 formulation stored in BFS containers did not form aggregates at room temperature or 2 to 8° C. for at least five months. Pouching of the vials after nitrogen flushing did not affect the physical stability of the product at either temperature.

The wCEX-HPLC stability results for the P05 formulation are shown in Table 17 and Table 18 (% main peak and % deamidated peaks, respectively).

TABLE 17 wCEX-HPLC Stability Results (% Main Peak) for
P05 formulation Stored in BFS containers

| Month | 25° C./60% RH | | 2 to 8° C. | |
|---|---|---|---|---|
| | Pouched | Not Pouched | Pouched | Not Pouched |
| 0 | 95.3 | 95.3 | 95.3 | 95.3 |
| 1 | 94.1 | 93.9 | 95.0 | 95.0 |
| 2 | 92.7 | 92.7 | 95.8 | 95.8 |
| 3 | 90.0 | 90.0 | 95.5 | 95.5 |
| 4 | 87.4 | 88.3 | 95.4 | 95.5 |
| 5 | 85.8 | 86.1 | 95.7 | 95.7 |

TABLE 18 wCEX-HPLC Stability Results (% Deamidated Peaks)
for P05 formulation Stored in BFS containers

| Month | 25° C./60% RH | | 2 to 8° C. | |
|---|---|---|---|---|
| | Pouched | Not Pouched | Pouched | Not Pouched |
| 0 | 0.8 | 0.8 | 0.8 | 0.8 |
| 1 | 1.6 | 1.8 | 1.2 | 1.2 |
| 2 | 2.7 | 2.7 | 0.12 | 0.50 |
| 3 | 4.7 | 4.8 | 0.42 | 0.41 |
| 4 | 6.7 | 7.0 | 0.60 | 0.51 |
| 5 | 9.5 | 8.5 | 0.34 | 0.33 |

The wCEX-HPLC results indicate that the P05 formulation in blow-fill seal containers remained stable at room temperature for up to five months. P05 also retained stability for at least 5 months at 2 to 8° C. Pouching of the containers after nitrogen flushing did not affect the stability of the product at either temperature.

The RP-HPLC stability results for the P05 engineering run drug product are shown in Table 19 and Table 20 (% main peak and % oxidized protein peaks, respectively).

TABLE 19

RP-HPLC Stability Results (% Main Peak) for
P05 formulation Stored in BFS containers

| Month | 25° C./60% RH | | 2 to 8° C. | |
|---|---|---|---|---|
| | Pouched | Not Pouched | Pouched | Not Pouched |
| 0 | 97.6 | 97.6 | 97.6 | 97.6 |
| 1 | 96.2 | 96.3 | 97.3 | 97.1 |
| 2 | 96.0 | 96.0 | 97.3 | 97.1 |
| 3 | 94.9 | 93.5 | 97.2 | 97.0 |
| 4 | 94.1 | 92.6 | 96.7 | 96.5 |
| 5 | 91.6 | 91.3 | 96.2 | 96.0 |

TABLE 20

RP-HPLC Stability Results (% Oxidized Peak)
for P05 formulation Stored in BFS containers

| Month | 25° C./60% RH | | 2 to 8° C. | |
|---|---|---|---|---|
| | Pouched | Not Pouched | Pouched | Not Pouched |
| 0 | 2.2 | 2.2 | 2.2 | 2.2 |
| 1 | 3.3 | 3.7 | 2.4 | 2.5 |
| 2 | 3.6 | 4.1 | 2.4 | 2.6 |
| 3 | 4.6 | 5.1 | 2.5 | 2.7 |
| 4 | 5.4 | 6.4 | 2.9 | 3.1 |
| 5 | 8.4 | 7.4 | 3.6 | 3.5 |

The RP-HPLC results indicate that the P05 formulation stored in BFS containers was stable at room temperature and 2 to 8° C. for at least five months.

Additionally, osmolality and pH measurements indicated that no significant change in osmolality or pH occurred over time, for samples at 25° C. (see Table). This demonstrates that little to no evaporation occurred, and that the pH of the solution remained stable. The protein concentration as assessed using $A_{280}$ was also consistent with previous measurements (see Table 21). Overall, EBI-005 exhibited excellent physical stability after prolonged storage in blow fill seal vials at at 2 to 8° C. and at ambient temperature (RT).

TABLE 21

Osmolality, pH, and Concentration for the P05 formulation after Five Months of Storage in BFS Containers

| Description | Temperature | Packaging | Osmolality | pH | $A_{280}$ |
|---|---|---|---|---|---|
| Active Pharmaceutical 5 mg/mL | 25° C. | Pouched | 318 | 6.06 | 4.89 |
| Active Pharmaceutical 5 mg/mL | 25° C. | Not pouched | 325 | 6.05 | 4.94 |
| Active Pharmaceutical 5 mg/mL | 4° C. | Pouched | 320 | 6.11 | 4.87 |
| Active Pharmaceutical 5 mg/mL | 4° C. | Not pouched | 319 | 6.07 | 4.87 |
| vehicle | 25° C. | Not pouched | 328 | 6.02 | 0.00* |
| vehicle | 4° C. | Not pouched | 322 | 6.06 | −0.02* |

*Blanked with Milli-Q ™ water

Example 15: Methionine Containing Formulations

In some embodiments, the invention relates to a formulation as described herein containing methionine.

The use of antioxidant for P05 formulated in 10 mM sodium citrate, 5% w/v sorbitol, 0.1% w/v poloxamer 188, pH 6.0 was studied using two different stress conditions: temperature (storage at 40° C.) and forced oxidation using hydrogen peroxide. Hydrogen peroxide is a stressor that causes oxidation by free radicals and thus was used to emulate the oxidation effect that may occur after storage in multidose containers that have been gamma irradiated (see below). P05 exhibits increases in oxidation levels when stored at high temperatures for prolonged periods. The use of either 10 mM methionine or 7 mM bisulfate added to the formulation was tested for the P05 formulation stored 3 weeks at 40° C. Additionally, the same formulation was tested using forced oxidation, where 10% v/v of 0.02% hydrogen peroxide was added to the samples. The samples were tested by RP-HPLC to assess the levels of oxidation. Table 22 provides a data summary.

TABLE 22

RP-HPLC analysis of stressed samples with and without anti-oxidant

| concentration | Variable | condition tested | % main peak | % oxidized |
|---|---|---|---|---|
| 1 mg/mL | NA | control (not stressed) | 99 | 1 |
| 1 mg/mL | no additive | 3 weeks at 40° C. | 90 | 10 |
| 1 mg/mL | +10 mM Methionine | 3 weeks at 40° C. | 98 | 2 |
| 1 mg/mL | +7 mM Bisulfate | 3 weeks at 40° C. | 88 | 12 |
| 20 mg/mL | no additive | 3 weeks at 40° C. | 97 | 3 |
| 20 mg/mL | +10 mM Methionine | 3 weeks at 40° C. | 98 | 2 |
| 20 mg/mL | +7 mM Bisulfate | 3 weeks at 40° C. | 96 | 4 |
| 1 mg/mL | no additive | peroxide added to 0.002% | 38 | 62 |
| 1 mg/mL | +10 mM Methionine | peroxide added to 0.002% | 73 | 27 |
| 1 mg/mL | +7 mM Bisulfate | peroxide added to 0.002% | 38 | 62 |

These data demonstrate that methionine, but not bisulfate, reduces the level of oxidized protein, particularly at low concentrations for protein stored at high temperature or with peroxide addition.

The effect of both container closure systems (blow fill and multi-dose), and the use of anti-oxidant in the formulation for multidose vials, were studied for their effect on oxidation levels of P05. Multi-dose containers (vials) were sterilized by gamma irradiation. Gamma irradiation can result in the generation of free radicals in the container that can be detrimental to the chemical stability of the protein, specifically by oxidizing methionine residues on the molecule. Accordingly, the present experiment investigated whether the addition of methionine to P05 formulated in 10 mM sodium citrate, 5% w/v sorbitol, 0.1% w/v poloxamer 188, pH 6.0 would ameliorate the oxidation of P05. 10 mM methionine was used for P05 at 1 mg/mL in multi-dose or blow fill vials. The protein was stored at either 2-8° C. or ambient temperature for up to 4 weeks. The protein was analyzed by RP-HPLC to determine levels of oxidized P05. Table 23 shows a summary of results.

TABLE 23

RP-HPLC analysis of P05 stored in either blow filled or multi-dose containers ± methionine

| Container | Additive | Temperature | Time (weeks) | % Main Peak | % Oxidized Peak |
|---|---|---|---|---|---|
| blow fill | none | 2 to 8° C. | 0 | 98.6 | 1.4 |
| | | | 1 | 98 | 2 |
| | | | 2 | 97.9 | 2.1 |
| | | | 3 | 97.6 | 2.4 |
| | | | 4 | 97.6 | 2.4 |
| multidose | none | 2 to 8° C. | 0 | 98.2 | 1.7 |
| | | | 1 | 98.2 | 1.8 |
| | | | 2 | 97.9 | 2.1 |
| | | | 3 | 97.3 | 2.7 |
| | | | 4 | 97.3 | 2.7 |
| multidose | 10 mM methionine | 2 to 8° C. | 0 | 98.2 | 1.7 |
| | | | 1 | 98.2 | 1.8 |
| | | | 2 | 98.1 | 1.9 |
| | | | 3 | 97.7 | 2.3 |
| | | | 4 | 97.6 | 2.4 |
| blow fill | none | ambient | 0 | 98.6 | 1.4 |
| | | | 1 | 97.3 | 2.7 |
| | | | 2 | 96.6 | 3.4 |
| | | | 3 | 96.5 | 3.5 |
| | | | 4 | ND* | ND* |

TABLE 23-continued

RP-HPLC analysis of P05 stored in either blow filled or multi-dose containers ± methionine

| Container | Additive | Temperature | Time (weeks) | % Main Peak | % Oxidized Peak |
|---|---|---|---|---|---|
| multidose | none | ambient | 0 | 98.2 | 1.7 |
| | | | 1 | 96.4 | 3.6 |
| | | | 2 | 95.2 | 4.8 |
| | | | 3 | 93.8 | 6.2 |
| | | | 4 | 92.5 | 7.5 |
| multidose | 10 mM methionine | ambient | 0 | 98.2 | 1.7 |
| | | | 1 | 96.9 | 3.1 |
| | | | 2 | 96.2 | 3.8 |
| | | | 3 | 95.3 | 4.7 |
| | | | 4 | 95.3 | 4.7 |

*ND: not determined due to sample contamination

Addition of methionine to the formulation reduced oxidation in the multidose container. For example, after 4 weeks of storage in multidose containers at ambient temperature, the % oxidized peak in the formulation without methionine was 7.5% and the % oxidized peak in the formulation with methionine was only 4.7%.

Example 16: Therapeutic Effects of EBI-005 Formulation and Vehicle Formulation

A multicenter, double masked, randomized, placebo controlled clinical trial was completed to evaluate the safety and biological activity of an aqueous formulation of EBI-005 in patients with moderate to severe dry eye disease. The formulation employed in this study contained EBI-005 (also referred to herein as P05) at a concentration of either 20 mg/ml or 5 mg/ml (see below), sodium carboxymethyl cellulose in a concentration of 0.25% w/v; poloxamer 188 in a concentration of 0.1% w/v; sorbitol in a concentration of 5% w/v; and sodium phosphate in a concentration of 10 mM. The trial was conducted in 74 patients at eight centers in the United States. The trial was conducted in a natural environment (a controlled adverse environment chamber was not used).

Patients were screened against eligibility criteria at a first visit. Patients who qualified for enrollment received topical administration of vehicle in each eye three times per day for one week. At the conclusion of the one-week run-in period, patients were again reassessed against eligibility criteria. Those patients who qualified under these additional criteria were randomized to one of three treatment groups. The Corneal Fluorescein Staining (CFS) score, Ocular Surface Disease Index (OSDI) score and other measures taken at randomization are referred to herein as baseline measures.

Eligible subjects were at least 18 years of age, with moderate to severe dry eye disease. Additional eligibility criteria included the following: (i) OSDI score greater than or equal to 23 and less than 90 at the time of screening; (ii) OSDI score greater than or equal to 19 at randomization; (iii) CFS score greater than or equal to six and less than 15 on the NEI scale at the time of screening; and (iv) CFS score greater than or equal to five at randomization.

Patients who were randomized to a treatment group were treated in both eyes three times per day for six weeks beginning at randomization. Treatments for the three groups in this trial were as follows: (i) in the first group, 22 patients received topical administration in each eye three times per day of EBI-005 formulation containing EBI-005 at a concentration of 20 mg/ml, (ii) in the second group, 22 patients received topical administration in each eye three times per day of EBI-005 formulation, containing EBI-005 at a concentration of 5 mg/ml, (iii) in the third group, 30 patients received topical administration in each eye three times per day of vehicle formulation (vehicle formulation was an aqueous formulation containing the same components as the EBI-005 formulation, except that EBI-005 was not in the vehicle formulation).

Figure 7:
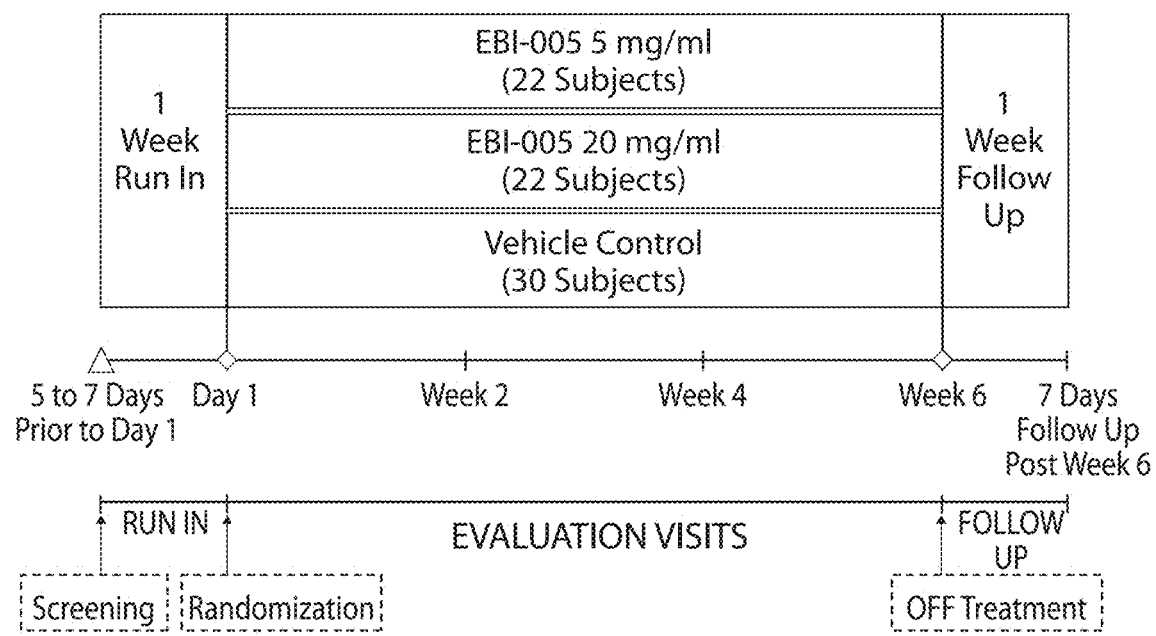
FIG. 7 depicts the design of the clinical trial described in Example 16.

Patients were assessed at screening; at randomization; at evaluation visits on weeks two, four and six following randomization; and at a follow up visit one week after the completion of treatment. The timeline for this clinical trial and number of patients randomized into the EBI-005 treatment and vehicle control groups are depicted in FIG. 7. Pain was assessed based on analysis of a single question from the 12 questions of the OSDI that asked patients about painful or sore eyes.

Figure 8:
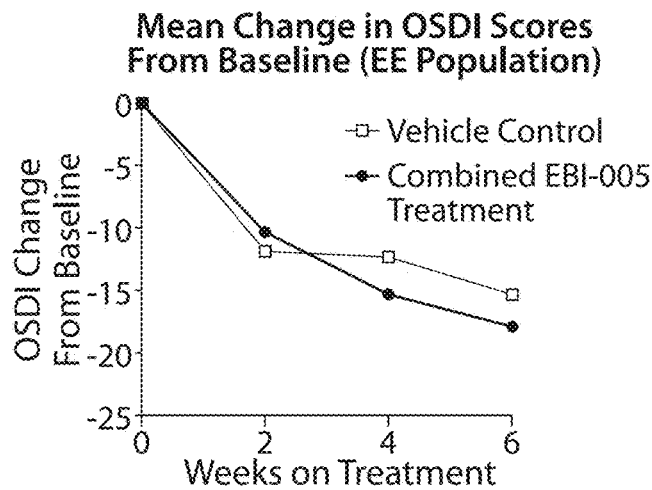
FIG. 8 is a graph showing the mean change from baseline in the OSDI score for the groups of subjects who received EBI-005 formulations (combined data for the groups that received 5 mg/ml and 20 mg/ml treatments) and vehicle formulation.
Figure 9:
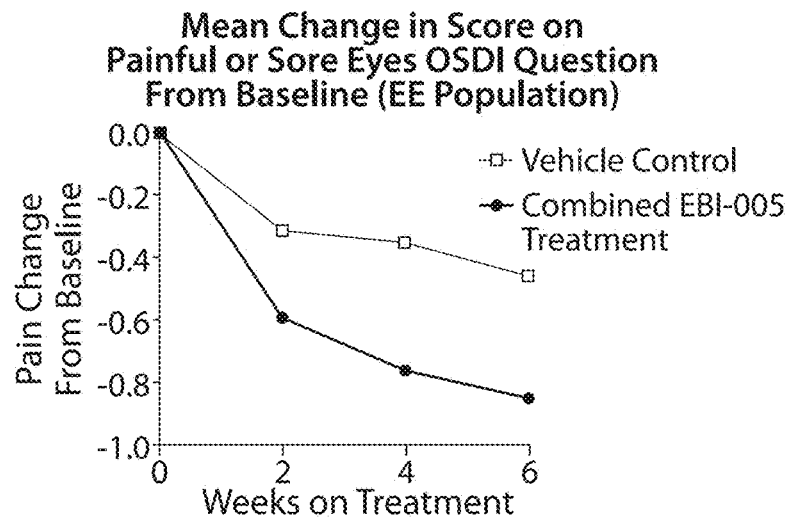
FIG. 9 is a graph showing the mean change from baseline in pain for the groups of subjects who received EBI-005 formulations (combined data for the groups that received 5 mg/ml and 20 mg/ml treatments) and vehicle formulation.

Results are shown in FIG. 8 to 10. These results show that signs and symptoms of dry eye disease, as assessed using OSDI score (FIG. 8), pain (FIG. 9), and corneal fluorescein staining (CFS) score (FIG. 10), improved during the course of treatment with the EBI-005 formulations. Surprisingly, treatment with the vehicle only formulation also resulted in notable improvements in OSDI score, pain, and CFS score.

Example 17: A Double-Masked, Randomized, Controlled Study of EBI-005 (5 mg/ml) Topical Ophthalmic Solution and Vehicle in Subjects with Moderate to Severe Dry Eye Disease (DED)

A study is conducted determining the efficacy of a vehicle formulation (10 mM sodium citrate, pH 6.0, 5% sorbitol (w/v), and 0.1% poloxamer 188 (w/v)) and a therapeutic formulation (10 mM sodium citrate, pH 6.0, 5% sorbitol (w/v), and 0.1% poloxamer 188 (w/v) containing 5 mg/ml P05) given as a topical ophthalmic solution in each eye to subjects with moderate to severe dry eye disease (DED) three times daily for 12 weeks.

Subjects are assessed for DED and inclusion criteria include having a history of dry eye disease (DED) in both eyes supported by a previous clinical diagnosis or have a self-reported history of subjective complaints for at least 6 months prior to screening (Visit 1), have ongoing DED, in the same eye or both eyes, as defined by the following criteria at Visit 1: an OSDI score of ≥23 and ≤75 and have scored the painful or sore eye question of the OSDI and a Total Corneal Fluorescein Staining Score of ≥6 (NEI scale) and <15. Screened subjects then undergo a five to eight day treatment with masked vehicle formulation, and are then rescreened (Visit 2) to confirm they meet the randomization criteria at this visit. The randomization criteria include having a total OSDI score of ≥19 and <50, having a total corneal fluorescein staining score of ≥5 (NEI scale) in the same qualifying eye as in Visit 1 and CFS <15 in at least one eye, and having complied with the five to eight day masked vehicle formulation period. Compliance is defined as administering at least 80% of the doses.

Subjects are then randomized to treatment with vehicle formulation or therapeutic formulation and are provided with enough vehicle formulation or therapeutic formulation to administer one drop in each eye 3 times daily through visit 4 (week 3/note that the week numbering starts after subjects are randomized and assigned to receive vehicle or therapeutic formulation). Additional drug is dispensed at each subsequent visit through Visit 6 (week 9). Subjects are evaluated at Visit 3 (week 1), Visit 4 (week 3), Visit 5 (week 6), Visit 6 (week 9), Visit 7 (week 12) and Visit 8 (week 15).

The last dose of study drug and final treatment visit are completed at Visit 7 (Week 12). The final evaluation is three weeks later at Visit 8 (follow-up, Week 15).

Formulations are provided as a 2 to 8° C. solution in a low-density polyethylene (LDPE) blow fill unit. Subjects are provided with ReFresh Plus® tears to be used if required, over the 21 day period preceding the final evaluation. Subjects do not use any such artificial tears during other parts of the study. Additional study information is available at clinicaltrials.gov, trial no. NCT01998802.

Evaluation of subjects during the study includes Total Corneal Fluorescein Staining (a sign), painful or sore eye question of the OSDI questionnaire (a symptom), total OSDI and individual questions and domains of the OSDI, inferior and central region CFS, global assessment (investigator and subject), subject-rated severity of individual symptoms of dry eye, and Schirmer test without anesthesia. Improvements in at least one of these criteria at the end of the first week (i.e., after the three to eight day masked vehicle run-in) and/or during subsequent study visits for those subjects assigned to the vehicle formulation group compared to their initial evaluation, further demonstrate the efficacy of a vehicle formulation. Improvements in at least one of these criteria during subsequent study visits for those subjects assigned to the therapeutic formulation group compared to their initial evaluation or their evaluation after the three to eight day masked vehicle run-in, further demonstrate the efficacy of a therapeutic formulation, e.g., a formulation comprising P05.

Other embodiments are within the scope of the following claims.

What is claimed is:

1. An aqueous formulation comprising
1-50 mg/ml of an IL-1β/IL-1Ra chimeric cytokine protein comprising an amino acid sequence selected from any one of SEQ ID NOs: 1-7;
a buffering agent selected from sodium citrate and sodium phosphate;
sorbitol at a concentration of 3.5-6.5% (w/v); and poloxamer 188 at a concentration of 0.07-0.13% (w/v);

wherein the formulation has a pH of 5.5 to 7.5.

2. The formulation of claim 1, wherein the chimeric cytokine protein comprises the amino acid sequence of SEQ ID NO: 5.

3. The formulation of claim 1, wherein the formulation further comprises an amino acid selected from arginine, glutamic acid, histidine, methionine, or a combination thereof.

4. The formulation of claim 3, wherein methionine is present in the formulation.

5. The formulation of claim 2, wherein the formulation further comprises methionine and has reduced oxidation, compared to a corresponding formulation that does not comprise methionine, when the formulation is subjected to storage for at least 4 weeks at 25° C.

6. The formulation of claim 5, wherein the formulation has reduced oxidation, compared to a corresponding formulation that does not comprise methionine, when the formulation is subjected to storage in a multidose container.

7. The formulation of claim 2, wherein the formulation has reduced particle counts for particles ≥2 μm compared to a formulation comprising polysorbate 20, polysorbate 80, or no surfactant, as assessed using microfluidic imaging, SEC, $A_{280}$, and/or visual inspection.

8. The formulation of claim 2, wherein the formulation is stable after storage for: (a) at least 5 months at 2-8° C.; or (b) at least 5 months under ambient conditions.

9. The formulation of claim 1, further comprising carboxymethyl cellulose.

10. An aqueous formulation comprising:

1-50 mg/ml of an IL-1β/IL-1Ra chimeric cytokine protein comprising an amino acid sequence selected from any one of SEQ ID NOs: 1-7;

a buffering agent selected from sodium citrate and sodium phosphate;
sorbitol at a concentration of 3.5-6.5% (w/v); and
poloxamer 188 at a concentration of 0.05-0.15% (w/v);
wherein the formulation has a pH of 5.5 to 7.5.

11. An aqueous formulation comprising:
1-100 mg/ml of an IL-1β/IL-1Ra chimeric cytokine protein comprising an amino acid sequence selected from any one of SEQ ID NOs: 1-7;
a buffering agent selected from sodium citrate and sodium phosphate;
sorbitol at a concentration of 3.5-6.5% (w/v); and
poloxamer 188 at a concentration of 0.05-0.15% (w/v);
wherein the formulation has a pH of 5.5 to 7.5.

* * * * *